(12) United States Patent
Dietz et al.

(10) Patent No.: US 9,737,735 B2
(45) Date of Patent: *Aug. 22, 2017

(54) ULTRASONIC SURGICAL APPARATUS WITH SILICON WAVEGUIDE

(71) Applicant: Ethicon Endo-Surgery, Inc., Cincinnati, OH (US)

(72) Inventors: Timothy G. Dietz, Terrace Park, OH (US); Foster B. Stulen, Mason, OH (US); William A. Olson, Cincinnati, OH (US); William Dannaher, Cincinnati, OH (US); John Willis, Cincinnati, OH (US); Sora Rhee, Cincinnati, OH (US); Juergen Burger, Ipsach (CH); Philippe Margairaz, La Chaux-de-Fonds (CH); Robert Lockhart, Lausanne (CH); Franz Friedrich, The Hague (NL); Danik Brand, Savagnier (CH); Herbert Keppner, Colombier (CH); Jean-Paul Sandoz, Cormondreche (CH)

(73) Assignee: ETHICON LLC, Guaynabo, PR (US)

( * ) Notice: Subject to any disclaimer, the term of this patent is extended or adjusted under 35 U.S.C. 154(b) by 481 days.

This patent is subject to a terminal disclaimer.

(21) Appl. No.: 13/745,385

(22) Filed: Jan. 18, 2013

(65) Prior Publication Data

US 2013/0197550 A1 Aug. 1, 2013

Related U.S. Application Data

(63) Continuation of application No. 12/857,399, filed on Aug. 16, 2010, now Pat. No. 8,882,792.

(Continued)

(51) Int. Cl.
*A61B 17/32* (2006.01)
*A61N 7/00* (2006.01)
(Continued)

(52) U.S. Cl.
CPC .............. *A61N 7/00* (2013.01); *A61B 8/4272* (2013.01); *A61B 17/320068* (2013.01);
(Continued)

(58) Field of Classification Search
CPC .... A61B 17/320068; A61B 2017/2253; A61B 2017/306; A61B 2017/00473;
(Continued)

(56) References Cited

U.S. PATENT DOCUMENTS

| 3,526,219 A | 9/1970 | Balamuth |
| 3,589,363 A | 6/1971 | Banko et al. |

(Continued)

FOREIGN PATENT DOCUMENTS

| EP | 0144741 | 6/1985 |
| FR | 2926731 | 7/2009 |

(Continued)

OTHER PUBLICATIONS

Office Action, U.S. Appl. No. 12/857,399 (Nov. 4, 2013).
(Continued)

*Primary Examiner* — Julian W Woo
(74) *Attorney, Agent, or Firm* — Thompson Hine LLP

(57) ABSTRACT

Ultrasound surgical apparatus are disclosed, including: medical ultrasound handpieces with proximally mounted ultrasound radiators configured to create a distally-focused beam of ultrasound energy, in combination with distal guide members for control of focal point depth; medical ultrasound handpieces with proximally mounted ultrasound radiators configured to create a distally-focused beam of ultrasound energy, in combination with distal rolling members for manipulability and control of focal point depth; medical ultrasound handpiece assemblies with coupled end effectors providing a probe with a probe dilation region configured to have an average outside diameter that is equal (Continued)

to or greater than the average outside diameter of a probe tip and neck; as well as junctions to an ultrasonically inactive probe sheath; medical ultrasound handpiece assemblies with coupled end effectors having positionable, ultrasonically inactive probe sheath ends slidably operable to both cover and expose at least a probe tip; and ultrasound transducer cores including a transducer structure affixed to a longitudinally elongated, generally planar, single crystal or polycrystalline material waveguide.

40 Claims, 54 Drawing Sheets

Related U.S. Application Data

(60) Provisional application No. 61/233,945, filed on Aug. 14, 2009.

(51) Int. Cl.
| | | |
|---|---|---|
| *A61B 17/225* | (2006.01) | |
| *A61B 17/30* | (2006.01) | |
| *B06B 3/00* | (2006.01) | |
| *G10K 11/24* | (2006.01) | |
| *A61B 8/00* | (2006.01) | |
| *A61B 17/00* | (2006.01) | |

(52) U.S. Cl.
CPC ............ *B06B 3/00* (2013.01); *G10K 11/24* (2013.01); *A61B 2017/00473* (2013.01); *A61B 2017/00964* (2013.01); *A61B 2017/2253* (2013.01); *A61B 2017/306* (2013.01); *A61B 2017/320072* (2013.01); *A61B 2017/320084* (2013.01); *A61B 2017/320088* (2013.01); *A61B 2017/320096* (2013.01); *A61B 2217/005* (2013.01); *A61B 2217/007* (2013.01); *A61N 2007/0034* (2013.01); *A61N 2007/0078* (2013.01); *A61N 2007/0082* (2013.01); *Y10T 156/10* (2015.01); *Y10T 156/1062* (2015.01)

(58) Field of Classification Search
CPC ......... A61B 2017/00964; A61B 2017/320072; A61B 2017/320084; A61B 2017/320088; A61B 2017/320096; A61B 2217/005; A61B 2217/007; A61N 2007/0034; A61N 2007/0078; A61N 2007/00
See application file for complete search history.

(56) References Cited

U.S. PATENT DOCUMENTS

| | | | |
|---|---|---|---|
| 3,990,452 | A | 11/1976 | Murry et al. |
| 4,210,704 | A | 7/1980 | Chandross et al. |
| 4,428,748 | A | 1/1984 | Peyman et al. |
| 4,750,902 | A | 6/1988 | Wuchinich et al. |
| 5,069,664 | A | 12/1991 | Guess et al. |
| 5,084,012 | A | 1/1992 | Kelman |
| 5,322,055 | A | 6/1994 | Davison et al. |
| 5,493,372 | A * | 2/1996 | Mashtare et al. ............ 399/313 |
| 5,569,968 | A | 10/1996 | Lal et al. |
| 5,595,328 | A | 1/1997 | Safabakhsh et al. |
| 5,683,592 | A | 11/1997 | Bartholomew et al. |
| 5,728,089 | A | 3/1998 | Lal et al. |
| 5,911,699 | A | 6/1999 | Anis et al. |
| 5,954,736 | A | 9/1999 | Bishop et al. |
| 5,984,904 | A | 11/1999 | Steen et al. |
| 6,036,661 | A | 3/2000 | Schwarze et al. |
| 6,082,180 | A | 7/2000 | Greenwood |
| 6,278,218 | B1 | 8/2001 | Madan et al. |
| 6,283,981 | B1 | 9/2001 | Beaupre |
| 6,309,400 | B2 | 10/2001 | Beaupre |
| 6,325,811 | B1 | 12/2001 | Messerly |
| 6,385,429 | B1 * | 5/2002 | Weber et al. ............... 399/319 |
| 6,423,082 | B1 | 7/2002 | Houser et al. |
| 6,440,121 | B1 | 8/2002 | Weber et al. |
| 6,582,381 | B1 | 6/2003 | Yehezkeil et al. |
| 6,638,249 | B1 | 10/2003 | Lal et al. |
| 6,666,825 | B2 | 12/2003 | Smith et al. |
| 6,699,237 | B2 | 3/2004 | Weber et al. |
| 6,736,835 | B2 * | 5/2004 | Pellegrino et al. ............ 607/96 |
| 6,740,058 | B2 | 5/2004 | Lal et al. |
| 6,869,420 | B2 | 3/2005 | Lal et al. |
| 6,923,790 | B2 | 8/2005 | Lal et al. |
| 6,939,317 | B2 | 9/2005 | Zacharias |
| 7,105,103 | B2 | 9/2006 | Keenan et al. |
| 7,285,096 | B2 | 10/2007 | Burba et al. |
| 7,387,742 | B2 | 6/2008 | Daskal et al. |
| 7,396,484 | B2 | 7/2008 | Daskal et al. |
| 7,530,986 | B2 | 5/2009 | Beaupre et al. |
| 8,137,371 | B2 * | 3/2012 | Cuny ............... A61B 17/32006 606/169 |
| 8,334,635 | B2 | 12/2012 | Voegele et al. |
| 8,348,967 | B2 | 1/2013 | Stulen |
| 8,372,102 | B2 | 2/2013 | Stulen et al. |
| 8,394,115 | B2 | 3/2013 | Houser et al. |
| 8,430,898 | B2 | 4/2013 | Wiener et al. |
| 8,882,792 | B2 * | 11/2014 | Dietz et al. .................... 606/169 |
| 2001/0016804 | A1 | 8/2001 | Cunningham et al. |
| 2001/0025190 | A1 | 9/2001 | Weber et al. |
| 2002/0077550 | A1 | 6/2002 | Rabiner et al. |
| 2002/0091404 | A1 | 7/2002 | Beaupre et al. |
| 2002/0179162 | A1 | 12/2002 | Lal et al. |
| 2002/0193817 | A1 | 12/2002 | Lal et al. |
| 2003/0195468 | A1 | 10/2003 | Lal et al. |
| 2003/0199165 | A1 | 10/2003 | Keenan et al. |
| 2004/0054364 | A1 | 3/2004 | Aranyi et al. |
| 2005/0101869 | A1 | 5/2005 | Burba et al. |
| 2005/0188548 | A1 | 9/2005 | Daskal et al. |
| 2005/0266680 | A1 | 12/2005 | Daskal et al. |
| 2006/0015130 | A1 | 1/2006 | Voorhees et al. |
| 2006/0090956 | A1 | 5/2006 | Peshkovskiy et al. |
| 2006/0235306 | A1 | 10/2006 | Cotter et al. |
| 2007/0016040 | A1 | 1/2007 | Nita |
| 2007/0118170 | A1 | 5/2007 | Kieturakis et al. |
| 2007/0239028 | A1 | 10/2007 | Houser et al. |
| 2007/0260172 | A1 | 11/2007 | Nita |
| 2008/0027328 | A1 | 1/2008 | Klopotek et al. |
| 2008/0194999 | A1 | 8/2008 | Yamaha et al. |
| 2008/0202550 | A1 | 8/2008 | McDermott et al. |
| 2008/0214967 | A1 | 9/2008 | Aranyi et al. |
| 2008/0234710 | A1 | 9/2008 | Neurohr et al. |
| 2008/0234711 | A1 | 9/2008 | Houser et al. |
| 2008/0243162 | A1 | 10/2008 | Shibata et al. |
| 2008/0246559 | A1 | 10/2008 | Ayazi et al. |
| 2008/0300611 | A1 | 12/2008 | Houser et al. |
| 2009/0018471 | A1 | 1/2009 | Dorawa et al. |
| 2009/0030311 | A1 | 1/2009 | Stulen et al. |
| 2009/0030438 | A1 | 1/2009 | Stulen |
| 2009/0036914 | A1 | 2/2009 | Houser |
| 2009/0069830 | A1 | 3/2009 | Mulvihill et al. |
| 2009/0143795 | A1 | 6/2009 | Robertson |
| 2011/0040213 | A1 | 2/2011 | Dietz et al. |
| 2011/0082486 | A1 | 4/2011 | Messerly et al. |
| 2011/0087213 | A1 | 4/2011 | Messerly et al. |
| 2011/0087216 | A1 | 4/2011 | Aldridge et al. |
| 2011/0087256 | A1 | 4/2011 | Wiener et al. |
| 2011/0196404 | A1 | 8/2011 | Dietz et al. |
| 2012/0022525 | A1 | 1/2012 | Dietz et al. |
| 2012/0022526 | A1 | 1/2012 | Aldridge et al. |
| 2012/0078244 | A1 | 3/2012 | Worrell et al. |
| 2012/0116261 | A1 | 5/2012 | Mumaw et al. |
| 2012/0116263 | A1 | 5/2012 | Houser et al. |
| 2012/0116364 | A1 | 5/2012 | Houser et al. |
| 2012/0116366 | A1 | 5/2012 | Houser et al. |
| 2012/0116367 | A1 | 5/2012 | Houser et al. |
| 2012/0116379 | A1 | 5/2012 | Yates et al. |
| 2012/0116391 | A1 | 5/2012 | Houser et al. |
| 2012/0269676 | A1 | 10/2012 | Houser et al. |
| 2012/0289984 | A1 | 11/2012 | Houser et al. |
| 2012/0310262 | A1 | 12/2012 | Messerly et al. |

(56) References Cited

U.S. PATENT DOCUMENTS

| | | |
|---|---|---|
| 2012/0310263 A1 | 12/2012 | Messerly et al. |
| 2012/0310264 A1 | 12/2012 | Messerly et al. |
| 2013/0023875 A1 | 1/2013 | Harris et al. |
| 2013/0053831 A1 | 2/2013 | Johnson et al. |
| 2013/0090576 A1 | 4/2013 | Stulen et al. |

FOREIGN PATENT DOCUMENTS

| | | |
|---|---|---|
| JP | S61-272045 A | 12/1986 |
| JP | 07-024311 U | 5/1995 |
| JP | 2006-034651 A | 2/2006 |
| JP | 2007-175509 | 7/2007 |
| JP | 08-084740 | 4/2008 |
| JP | 2009-266916 A | 11/2009 |
| WO | WO 98/38927 A1 | 9/1998 |
| WO | 02/081025 | 10/2002 |
| WO | 03/030754 A1 | 4/2003 |
| WO | 2006/082573 | 8/2006 |
| WO | 2007/140331 | 12/2007 |

OTHER PUBLICATIONS

Office Action, U.S. Appl. No. 12/857,399 (Mar. 17, 2014).
PCT, Invitation to Pay Additional Fees and Partial International Search Report, International Application No. PCT/US2010/045622 (Oct. 22, 2010).
PCT, International Search Report, International Application No. PCT/US2010/045622 (Jan. 31, 2011).
Lal, A., Micromachined Silicon Ultrasonic Longitudinal Mode Actuators: Theory and Applications to Surgery, Pumping, and Atomization (254 pages) (1996).
Brünahl, J., "Physics of Piezoelectric Shear Mode Inkjet Actuators" (109 pages) (2003).
Lee, J.E-Y. et al., "A Single-Crystal-Silicon Bulk-Acoustic-Mode Microresonator Oscillator," IEEE Electron Device Letters, vol. 29, No. 7, pp. 701-703 (Jul. 2008).
Product information entitled, "Designing with Piezoelectric Transducers: Nanopositioning Fundamentals," by Physik Instrumente (PI) GmbH & Co. (49 pages) (Sep. 2005).
Uchino, K., "Introduction to Micromechatronics," Report prepared on behalf of the International Center for Actuators and Transducers (122 pages) (Jun. 2003).
Zakel, E. et al., Process Makes Electroless Nickel/Gold Wafer Bumping Economical for Flip-Chip Packaging (6 pages) (2003).
Technical literature entitled "Shear Mode Actuators—Additional characterization," by Noliac A/S (2 pages), No date.
Chidambaram, P.R. et al., "Fundamentals of Silicon Material Properties for Successful Exploitation of Strain Engineering in Modern CMOS Manufacturing," IEEE Transactions on Electron Devices, vol. 53, No. 5, pp. 944-964 (May 2006).
Weichel, S. et al., "Silicon-to-silicon wafer bonding using evaporated glass," Sensors and Actuators, A 70, pp. 179-184 (1998).
Sergent, J.E., "Chapter 8: Materials and Processes for Hybrid Microelectronics and Multichip Modules," Electronic Materials and Processing Handbook, Third Edition, pp. 8.1-8.103 (2004).
Hwang, J.S., "Chapter 5: Solder Technologies for Electronic Packaging and Assembly," Electronic Materials and Processing Handbook, Third Edition, pp. 5.1-5.109 (2004).
Lassner, E. et al., "Chapter 6: Tungsten Alloys," Tungsten Properties, Chemistry, Technology of the Element, Alloys and Chemical Compounds, pp. 255-282 (1999).
European Search Report dated Sep. 22, 2014, Application No. EP 14 16 6440.
International Search Report dated Oct. 9, 2014, International Application No. PCT/US2014/010899.
European Patent Office, Communication pursuant to Article 94(3) EPC in Application No. EP 14166440.9, dated Mar. 11, 2016, pp. 1-4.
AU, Patent Examination Report No. 1, Australian Application No. 2010282256, 4 pages, dated Feb. 9, 2015.
CA, Examination Report, Canadian Application No. 2,770,743, 5 pages, dated Jun. 9, 2016.
CN, Notification of First Office Action (English Translation), Chinese Application No. 201080046527.8, 10 pages, dated Aug. 30, 2013.
EP, Communication Pursuant to Article 94(3) EPC, European Application No. 10747998.2, 4 pages, dated Mar. 1, 2013.
JP, Notification of Reasons for Refusal (English translation), Japanese Application No. 2012-524932, 4 pages, dated Apr. 15, 2014.
PCT, International Preliminary Report on Patentability, International Application No. PCT/US2010/045622, 8 pages, dated Jan. 20, 2012.
PCT, International Preliminary Report on Patentability, International Application No. PCT/US2014/010899, 13 pages, dated Jul. 21, 2015.

\* cited by examiner

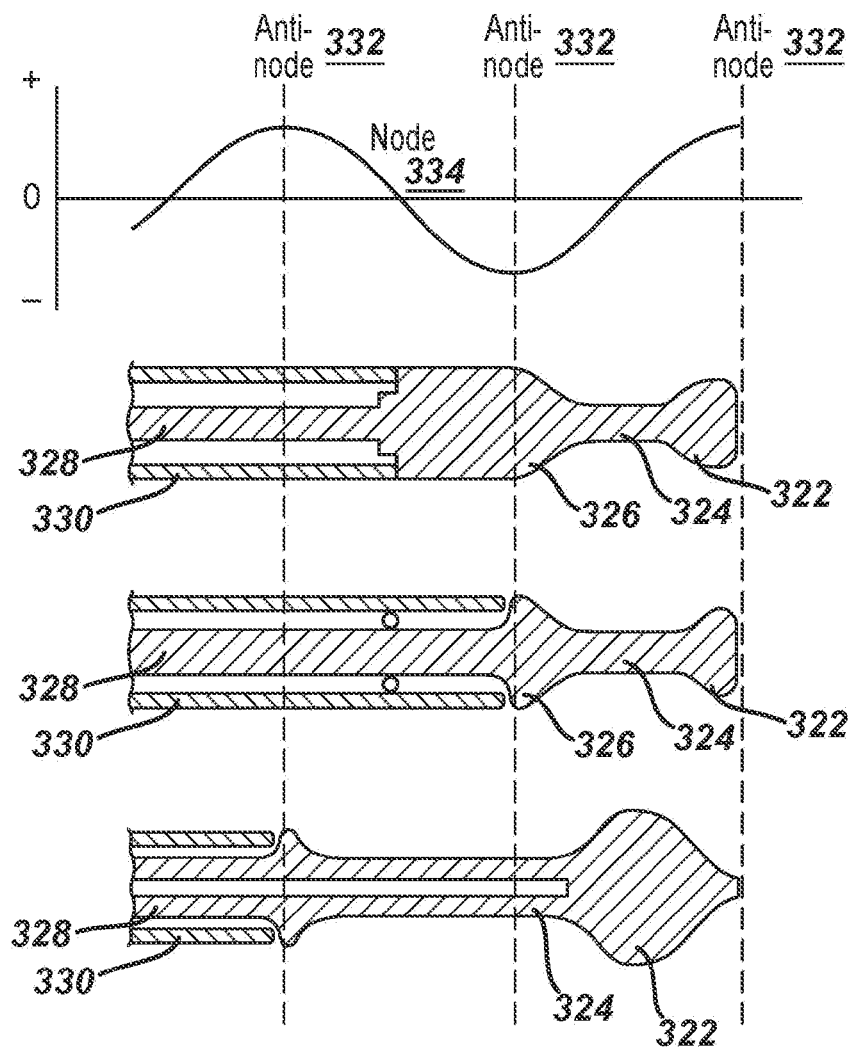
FIG. 14
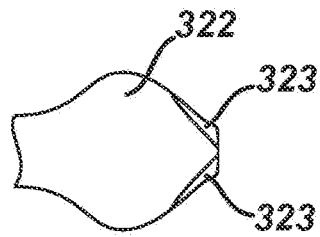 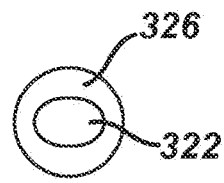 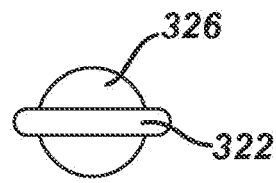
FIG. 15   FIG. 16   FIG. 17

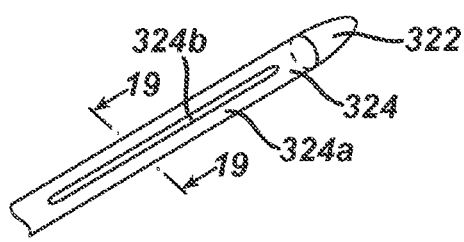
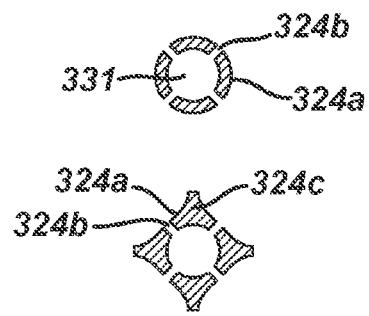
FIG. 18    FIG. 19
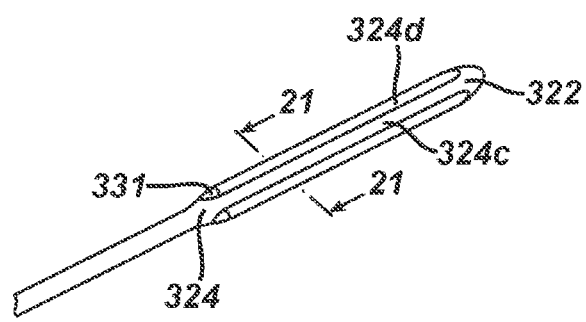
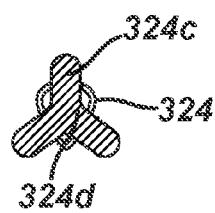
FIG. 20    FIG. 21

ULTRASONIC SURGICAL APPARATUS WITH SILICON WAVEGUIDE

CROSS-REFERENCE TO RELATED APPLICATIONS

This application claims the benefit of U.S. Provisional Application No. 61/233,945, filed on Aug. 14, 2009, and U.S. Nonprovisional application Ser. No. 12/857,399, filed on Aug. 16, 2010, the entire contents of which are incorporated herein by reference.

FIELD

The various embodiments relate to an ultrasonic surgical apparatus and, more particularly, to ultrasonic surgical instruments having a generally planar, monolithic or composite silicon waveguide.

BACKGROUND

Human skin is composed of two major layers, the epidermis and the dermis. Below these layers lies the hypodermis, which is not usually classified as a layer of skin. The thinner outer layer of the skin, the epidermis, provides a barrier to the external environment. The epidermis is typically about 0.05 to 1.5 mm thick (varying from its minimum at the eyelids to its maximum over the palms and soles of the feet). It is composed of many different cell types including keratinocytes, melanocytes, and Langerhan cells. Keratinocytes are the major cell type (being about 75 to 80% of the total number of cells), and are responsible for keeping water in the body and keeping other harmful chemicals and pathogens out. The epidermis is made up of a stratified squamous epithelium with an underlying basement membrane. It contains no blood vessels, and is nourished by diffusion from the dermis.

The thicker inner layer of the skin, the dermis, is the major component of human skin. The dermis, or corium, is typically about 0.3 to 5 mm thick (varying from its minimum at the eyelids to its maximum over the back). It is composed of a network of connective tissue, which provides strength, elasticity, and thickness to the skin, and contains other structures including capillaries, nerve endings, hair follicles, smooth muscle, glands, and lymphatic tissue. The main cell type of the dermis is the fibroblast, which is responsible for the synthesis and secretion of dermal matrix components such as collagen, elastin, and glycosaminoglycans. Collagen provides the strength, elastin the elasticity, and glycosaminoglycans the moistness and plumpness of the skin. With ageing, the thickness of the dermal layer is reduced, and this is believed to be partially responsible for the formation of wrinkles in ageing skin.

The hypodermis, also commonly referred to as the subcutaneous fat layer or subcutaneous tissue, lies below the dermis. Its purpose is to attach the skin to underlying bone and muscle as well as to supply the dermis with blood vessels and nerves. It is made up of loose connective tissue and elastin. The main cell types are fibroblasts, macrophages, and adipocytes. The hypodermis contains about 50% of total body fat, the fat serving as padding, insulation, and an energy reserve for the body.

Facial aging occurs as the result of several factors: inherent changes within the skin, the effects of gravity, the effects of facial muscles acting on the skin (dynamic lines), soft tissue loss or shift, bone loss, and a gradual loss of tissue elasticity. The epidermis begins to thin, causing the junction with the dermis to flatten. Collagen also decreases, and bundles of collagen, which give the skin turgor, become looser and lose strength. When the skin loses elasticity it is less able to resist stretching. The skin begins to wrinkle as a result of gravity, muscle pull, and tissue changes. Water loss and a breakdown of the connective bonds between cells also weakens the barrier function of the skin, which can cause the skin's pore size to increase.

As a person ages, the face loses volume, soft tissue, and fat. The appearance of jowls and folds is usually caused by the drooping of facial tissues and the folding of skin over areas where it is attached to and supported by the muscles below. Due to the reduction in soft tissue, the face appears more hollow. In various facial areas such as the forehead, eyes, nose, midface, and lower face, changes relating to aging have been well documented. For example, in the forehead area, the forehead and brow droop over time, which lowers the eyebrows and causes the upper eyelid skin to bunch. Forehead lines appear when one tries to hold the brows and eyelids up to counteract these changes. It is well known that the eye area is often the first facial feature to show signs of aging. Skin changes around the eyes occur earlier than in the rest of the face since the skin is thinnest here. The skin in this area also contains fewer glands and is subjected to constant blinking, squinting, rubbing, and pulling.

The midface area ages when the cheeks begin to droop, causing nasolabial folds, which are the lines that run from the sides of the nose to the corners of the mouth. It is known to treat these folds with facial fillers. In the nose area, the nose appears to elongate. Common causes of elongation are thinning of the soft tissue and loss of elasticity, which causes "drooping of the tip" and unmasking of the bone, creating a new hump.

In the lower face area, facial tissues descend, causing so-called "laugh lines." It is known to treat these folds and lines with facial fillers. Further down on the lower face, the corners of the mouth may droop, and a descent of the jowls can create folds often referred to as "marionette lines." Furthermore, jowls form when the cheeks sag around a fixed point along the jaw where the facial muscles attach to the jawbone.

Various injectables have been used for restoring tissue loss in the face. Since the 1980s, injectable collagen has been used as a soft-tissue filler to fill wrinkles, lines, and scars on the face. Collagen is a naturally occurring protein that supports various parts of the body including skin, tendons, and ligaments. Fat injections have also been used to add volume, fill wrinkles and lines, and enhance the lips. Fat injections involve taking fat from one part of a patient's body (typically the abdomen, thighs, or buttocks) and reinjecting it beneath the facial skin. Botulinum toxins, which were first approved for the treatment of neck spasms, cranial nerve disorders, and eye spasms, have also been used "off-label" for cosmetic purposes. With the recent FDA approval of Botox for cosmetic use in the glabellar region, the drug is becoming widely used for the temporary treatment of dynamic lines. In contrast to fillers, the botulinum toxin is injected into facial muscles, temporarily blocking nerve impulses and relaxing the muscles to smooth so-called "worry lines."

Hyaluronic acid is one of most commonly used cosmetic dermal fillers. Hyaluronic acid is a linear polysaccharide that exists naturally in all living organisms, and is a universal component of the extra-cellular spaces of body tissues. The identical structure of hyaluronic acid in all species and tissues makes this polysaccharide an ideal substance for use as a bio-material in health and medicine. Hyaluronic acid is present in many places in the human body. It gives volume to the skin, shape to the eyes, and elasticity to the joints. The highest concentrations of hyaluronic acid are found in connective tissues, and most of the hyaluronic acid produced by the human body (about 56%) is found in the skin.

Various forms of hyaluronic acid are provided commercially by a number of manufacturers. The most commonly used hyaluronic acid is a non-animal stabilized hyaluronic acid (NASHA), distributed in a clear gel form and produced by bacterial fermentation using streptococci bacteria. Different from animal-derived hyaluronic acid, the non-animal-derived hyaluronic acid is free from animal proteins. This limits the risk of animal-based disease transmission or the development of an allergic response. The most known non-animal stabilized hyaluronic acid is manufactured by Q-med AB of Seminariegatan, Uppsala, Sweden and commercially available under the tradename Restylane®. Since its commercialization in 1996, it is estimated that over 2,500,000 treatments have been carried out worldwide. Other non-animal stabilized hyaluronic acid products include Perlane® from Q-med, which has larger particles than Restylane®, and Captique™ from Genzyme Corporation. Another commonly used filler is a hyaluronic acid derivative manufactured by Genzyme Corporation and commercially available under the tradename Hylaform Plus. Hylaform Plus is a sterile, nonpyrogenic, viscoelastic, clear, colorless, transparent gel implant composed of cross-linked molecules of hyaluronan. Although hyaluronic acid and its derivatives are the most commonly used dermal fillers, they have limited long-term viability. The material must be reinjected periodically, typically every 4 to 12 months, due to hyaluronan metabolism in the body.

To increase the longevity of dermal fillers, high molecular weight formulations are being developed. However, increasing molecular weights result in higher and higher viscosities. The higher the viscosity, the more difficult it is to inject the desired amount of dermal filler into the desired location, or to extract any excess. In addition, because the dermal filler must be injected within the existing skin layers, and there is minimal ability to create a pocket for the filler to reside in, it is difficult to manipulate high molecular weight fillers within existing skin tissue to achieve the desired cosmetic effect. Also, once injected, high molecular weight dermal fillers may shift to a different location and create an undesirable cosmetic defect. Current methods which seek to use a lysing agent to remove excess or unwanted filler do not provide much differential action with respect to native tissue, causing damage to adjacent tissues and substantially increasing the risk of a poor aesthetic outcome.

Ultrasonic energy can be used to shear-thin highly viscous materials, and the applicants have found that ultrasonic energy can successfully be used to shear-thin collagen-based dermal fillers. The energy can be applied via direct contact ultrasound (at frequencies of 20-200 kHz) or via high intensity, focused, field effect ultrasound or "HIFU" (at frequencies of 50 kHz-20 MHz). Since a non-thermal shearing action will be desired from the HIFU source, the frequencies of interest will dip below the traditional lower frequency limit of high frequency medical ultrasound, 500 kHz, to at least 100 kHz. The lower frequency limit will typically be defined by the desired resolution of the focal point for treatment. Ultrasonic energy can also be used to undermine or dissect tissue, to release folds, or to create pockets within tissue.

The requirements and construction of devices for delivering contact ultrasound and HIFU will be different. Contact devices must come into direct contact with a filler in order for an ultrasonic element to shear-thin the filler material. HIFU devices, on the other hand, focus field effect ultrasound so as to shear-thin the filler material without direct contact between the ultrasound radiator and the filler. However, readily known devices are deficient in that contact devices are generally designed for the macroscopic coagulation or ablation of tissue surfaces, while HIFU devices are generally designed for the image-guided hyperthermic, coagulative, or cavitation-induced destruction of tissue at depth. Accordingly, improved ultrasonic apparatuses that are safe and effective for non-thermal, shallow depth dermatological treatments are required. In addition, methods for manipulating high molecular weight, high viscosity dermal fillers and shallow facial tissues are desired.

SUMMARY

A first embodiment of an ultrasonic surgical apparatus includes a medical ultrasound handpiece having a distal end and an ultrasound radiator mounted proximally from the distal end. The ultrasound radiator is configured to create a beam of ultrasound energy having a focal point at a predetermined distance from the ultrasound radiator in the direction of the distal end, and has at least one monolithic ultrasound source with a focused emitting surface or at least one array ultrasound source configured as an electronically focusable array. The first embodiment also includes a guide member for placement around a facial feature, whereupon the ultrasound handpiece is slidably engaged with the guide member to position the focal point within the skin.

A method of using the device of the first embodiment includes the steps of: injecting a dermal filler into the dermis of a facial feature; placing the distal guide member of the first embodiment on the surface of the skin so as to surround the facial feature; applying an acoustic gel to the skin over the facial feature; engaging the distal end of the ultrasound handpiece of the first embodiment with the emplaced guide member; and slidably translating the ultrasound handpiece upon the emplaced guide member to position the focal point of the ultrasound radiator within the injected dermal filler, then subsequently powering the ultrasound radiator to shear-thin the dermal filler.

A second embodiment of an ultrasonic surgical apparatus includes a medical ultrasound handpiece having a distal end, a distal rolling member for placement over a facial feature, and a ultrasound radiator mounted proximally from the distal end. The ultrasound radiator is configured to create a beam of ultrasound energy having a focal point at a predetermined distance from the ultrasound radiator in the direction of the distal end, and has at least one monolithic ultrasound source with a focused emitting surface or at least one array ultrasound source configured as an electronically focusable array. In certain expressions of the embodiment, the distal rolling member is externally coupled to the ultrasound radiator through an acoustic coupling medium generally contained within the medical ultrasound handpiece. In other expressions of the embodiment, the distal rolling member is internally coupled to the focusing ultrasound radiator, which is contained within the distal rolling member.

A method of using the device of the second embodiment includes the steps of: injecting a dermal filler into the dermis of the facial feature; placing the distal rolling member of the device of the second embodiment on the surface of the skin over the facial feature; applying an acoustic gel to the skin over the facial feature; and rollingly translating the distal rolling member over the skin to position the focal point of the focusing ultrasound radiator within the injected dermal filler, then subsequently powering the ultrasound radiator to shear-thin the dermal filler.

A third embodiment of an ultrasonic surgical apparatus includes a medical ultrasound handpiece assembly having an ultrasound transducer and an end effector coupled to the ultrasound transducer. The end effector has, in order, a distal probe tip, a probe neck, a probe dilation region, and ultrasonically active shaft, with the shaft being coaxially held within an ultrasonically inactive probe sheath. The probe dilation region is configured to have an average outside diameter that is equal to or greater than the average outside diameter of the probe tip and the average outside diameter of the probe neck. The probe sheath is configured to have an outside diameter that is approximately equal to the outside diameter of the probe dilation region so as to create a uniform junction between the probe sheath and the probe dilation region. In certain expressions of the embodiment, the junction may be tight between the probe sheath and the probe dilation region. In other expressions of the embodiment, the junction may be loose but self-cleaning.

A method of using the device of the third embodiment includes the steps of: injecting a dermal filler into a facial feature; inserting at least the distal probe tip of the device of the third embodiment beneath the surface of the skin and into the injected dermal filler; powering the ultrasound transducer to operate the probe tip; and inserting at least the distal probe tip into the injected dermal filler. A preferred method further includes the step, following the powering step, of inserting the probe dilation region beneath the surface of the skin to protect the surface of the skin from unintended contact with ultrasonically active portions of the probe.

A fourth embodiment of an ultrasound surgical apparatus includes a medical ultrasound handpiece assembly having an ultrasound transducer and an end effector coupled to the ultrasound transducer. The end effector has, in order, a distal probe tip, a probe neck, and an ultrasonically active shaft, with the shaft coaxially being held within an ultrasonically inactive probe sheath. The probe sheath is configured such that the distal end of the probe sheath is slidably operable to both cover and expose at least the probe tip. In certain expressions of the embodiment, the distal end of the probe sheath is configured to slidably retract when the probe sheath experiences a certain longitudinal resistance. In other expressions of the embodiment, the proximal end of the probe sheath is coupled to an adjustment mechanism for slidably retracting and extending the distal end of the probe sheath.

A method of using the device of the fourth embodiment includes the steps of: inserting at least the distal probe tip of the device of the fourth embodiment beneath the surface of the skin; powering the ultrasound transducer to operate the distal probe tip; inserting the distal end of the ultrasonically inactive probe sheath beneath the surface of the skin while the ultrasound transducer is powered; advancing the probe tip while the ultrasound transducer is powered; and retracting the distal end of the probe sheath to expose a greater length of the distal probe tip. A preferred method for use with devices including an adjustment mechanism further includes the step, following the insertion of the distal probe tip, of inserting the distal end of the probe sheath beneath the surface of the skin to protect the surface of the skin from unintended contact with ultrasonically active portions of the probe. The method may be applied to injected dermal fillers and blepharoplasty.

A fifth embodiment of an ultrasonic core for an ultrasound surgical apparatus includes a transducer structure affixed to a longitudinally elongated, generally planar, single crystal or polycrystalline material waveguide. The waveguide has, in order, a first resonator or proximal end portion, a transduction portion, and a second resonator. The fifth embodiment may also include a single or polycrystalline material end effector portion monolithically or resonantly coupled to the waveguide to serve at least as an ultrasonically active shaft.

Other aspects of the disclosed ultrasonic apparatus and method for shear-thinning dermal fillers will become apparent from the following description, the accompanying drawings, and the appended claims. Several benefits and advantages are obtained from one or more of the expressions of the embodiments of the invention. In one example, the ultrasound apparatuses disclosed herein help enable the economic manipulation of high molecular weight, high viscosity dermal fillers in vivo. In another example, the ultrasound apparatuses disclosed herein provide for the ultrasonic manipulation of tissues within specific layers or at specific depths while shielding overlying tissue. In yet another example, the methods of shear-thinning dermal filler materials disclosed herein help enable the in vivo reshaping of previously injected dermal fillers. In other examples, the devices and methods are used in microsurgical applications such as blepharoplasty. In general, contact and non-contact devices are disclosed which can be beneficially used to instantaneously decrease the viscosity of a dermal filler material without permanently decreasing the molecular weight of the material and/or the ability of the material to 'gel,' thereby increasing the long-term viability of injectable dermal filler treatments. Features of the devices allowing for the finely controlled application of ultrasound near or within sensitive soft tissues, such as the epidermis and dermis, are of course useful in other types of dermatological and microsurgical procedures.

BRIEF DESCRIPTION OF THE DRAWINGS

FIG. 14 is a cross-sectional side view of various end effector probe constructions.

FIG. 15 is a side view of a distal probe tip.

FIGS. 16 and 17 are front views of the distal probe tips shown in FIG. 14.

FIGS. 18 and 20 are perspective views of probe necks (including blunt distal probe tips).

FIGS. 19 and 21 are cross-sectional end views of the respective probe necks.

DETAILED DESCRIPTION

Figure 1:
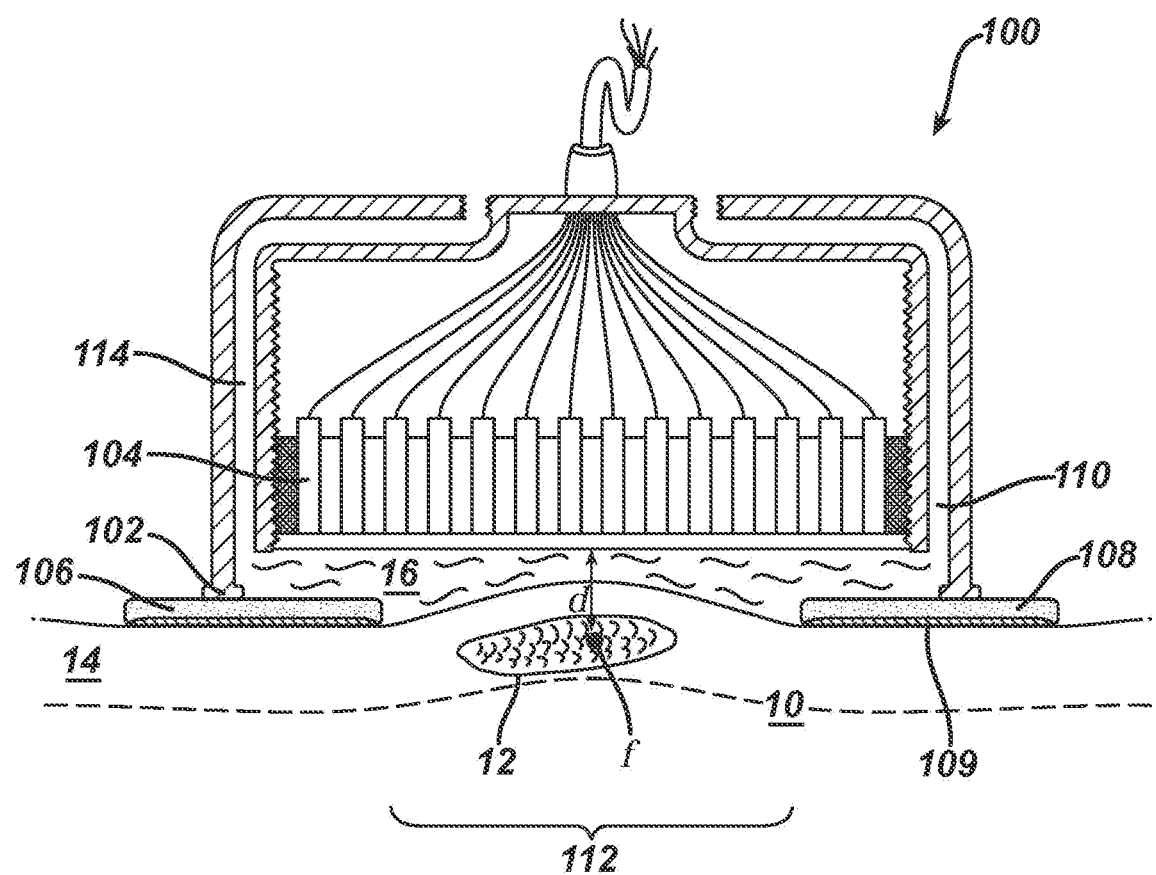
FIG. 1 is a cross-sectional side view of a medical ultrasound handpiece and guide member.

Before explaining the several embodiments of the present invention in detail, it should be noted that the expressions and embodiments are not limited in their application or use to the details of construction and arrangement of parts and steps illustrated in the accompanying drawings and description. The illustrative expressions and embodiments may be implemented or incorporated in other expressions, embodiments, variations, and modifications, and may be practiced or carried out in various ways. Furthermore, unless otherwise indicated, the terms and expressions employed herein have been chosen for the purpose of describing the illustrative embodiments of the present invention for the convenience of the reader, and are not for the purpose of limiting the invention.

It is further understood that any one or more of the following-described expressions, embodiments, examples, etc. may be combined with any one or more of the other following-described expressions, embodiments, examples, etc. Such modifications and variations are intended to be included within the scope of the claims.

A first embodiment of the invention is shown in FIGS. 1-4. The first embodiment includes a medical ultrasound handpiece 100 having a distal end 102 and a focusing ultrasound radiator 104 mounted proximally from the distal end. The ultrasound radiator 104 is configured to create a beam of ultrasound energy having a focal point, f, at a predetermined distance, d, from the ultrasound radiator 104 in the direction of the distal end 102. This configuration is used to focus ultrasound energy within a facial feature 10 having a pocket of dermal filler 12 implanted in the dermis (including the dermal junctions) to cause shear-thinning of the dermal filler 12. The ultrasound radiator 104 has at least one monolithic source with a focused emitting surface, at least one array source configured as an electronically focusable array, or a combination of such ultrasound sources. Examples of array sources are disclosed in PCT Application Publication No. WO/2006/082573, the entire contents of which are incorporated herein by reference.

Figure 6:
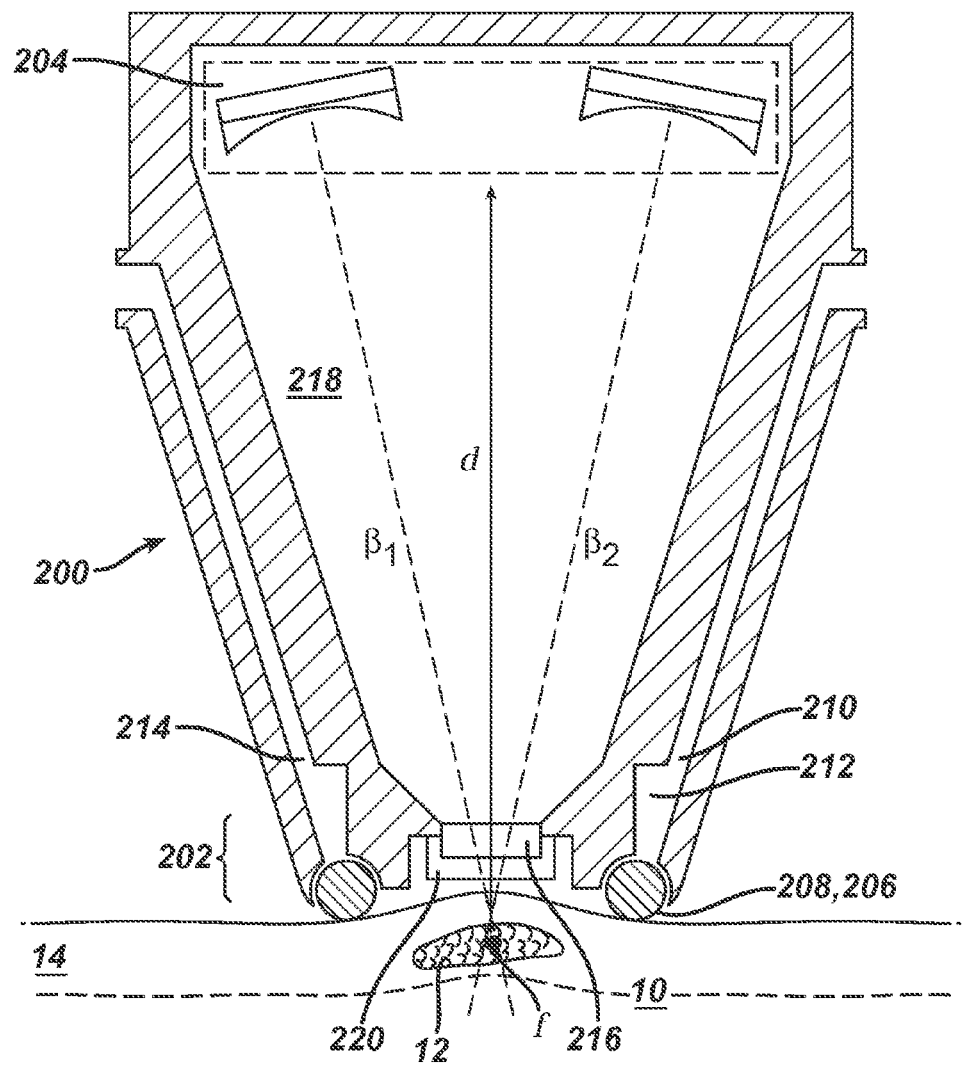

Because a focused monolithic source generates a shear which is strongest at the perimeter of the generated acoustic wave profile, additional sources may configured so that the beam axes, $B_1$ through $B_n$, of the sources generally converge upon the focal point f to enhance the ability of device to create shear proximate the focal point. A configuration of multiple ultrasound sources in a non-overlapping, convergingly focused assembly, as illustrated in FIG. 6, can enable this edge effect to be accentuated by varying the relative phases and intensities of the emitted ultrasound energy. However, this advantage is limited as a matter of practicality to devices which include a small plurality of focused monolithic sources, since a large array of transducers operated in this manner approximates the function of a single array source, i.e., multiplicity has rapidly diminishing returns in the face of increasing customization and complexity. The ultrasound radiator 104 is preferably configured to create both longitudinal and transverse acoustic waves, and should be coupled to the skin through an acoustic gel 16, which serves to improve coupling to the skin 14 and to improve the lubricity of the distal end 102 for movement over the skin 14. The use of acoustic gels and the dispensing of such gels are known in the art. See, for example, U.S. Pat. App. Publication No. 2008/0027328. The ultrasound radiator 104 should emit about 1 to 20 watts of effective power, with the heat generated thereby being dissipated or removed via thermal radiation, thermal conduction, or thermal mass or capacitance in order to prevent injury during continuous acoustic excitation. The acoustic gel 16 may be used to assist in such heat dissipation or removal.

It is important to note that if energy delivery is focused too deeply, then vital nerves and/or muscles may be damaged. However, if energy delivery is focused too shallowly, then the epidermis may be burned. The first embodiment also includes a guide member 106 for placement around the facial feature 10. The guide member 106 serves to define an area for treatment and to protect the skin 14 around that area from diffuse ultrasound energy near the focal point (or erroneous manipulation of the handpiece). The predetermined distance d may generally be adjusted electrically within an array ultrasound source, mechanically by varying the thickness of the guide member 106 (or adding additional members 106), and/or mechanically by varying the position of the focusing ultrasound radiator 104 with respect to the distal end 102 with a mechanical positioning system. However, guide member 106 may also serve to resist localized distortion of the skin 14 during application of the handpiece 100 to ensure that the predetermined distance d falls within the dermis (including the dermal junctions), as opposed to the epidermis or hypodermis, during a treatment procedure so as to minimize the need to adjust the distance d during a procedure.

In a first expression of the first embodiment, shown in FIG. 1, the distal guide member 106 may be a locating ring 108 to be positioned around the facial feature 10. In one construction, the locating ring 108 may be adhered to the surface of the skin 14 surrounding the facial feature 10 by an adhesive backing 109. In another construction, the locating ring 108 may be adhered to the surface of the skin 14 surrounding the facial feature 10 by a partial vacuum applied by a vacuum port 110 connected to a chamber 112 defined within locating ring 108 (and between the medical ultrasound handpiece 100 and the skin 14). In these or other constructions, the chamber 112 may be supplied with an acoustic gel 16 through the vacuum port 110, or through a separate fluid port 114. In one exemplary construction, the locating ring 108 is constructed from a flexible foam sheet. The foam is preferably flexible to conform to the face but essentially incompressible under typical loads (up to 5 psi) in order to maintain its shape thickness. The foam is preferably open-celled to provide a path for vacuum and to enhance acoustic protection around the periphery of the chamber 112. Locating ring 108 may define a substantially annular periphery for chamber 112, but may also or alternately be cut by the user to define the periphery of an area for treatment. The distal end 102 is slidably engaged with the locating ring 108 to position the focal point f within the skin 14.

Figure 2:
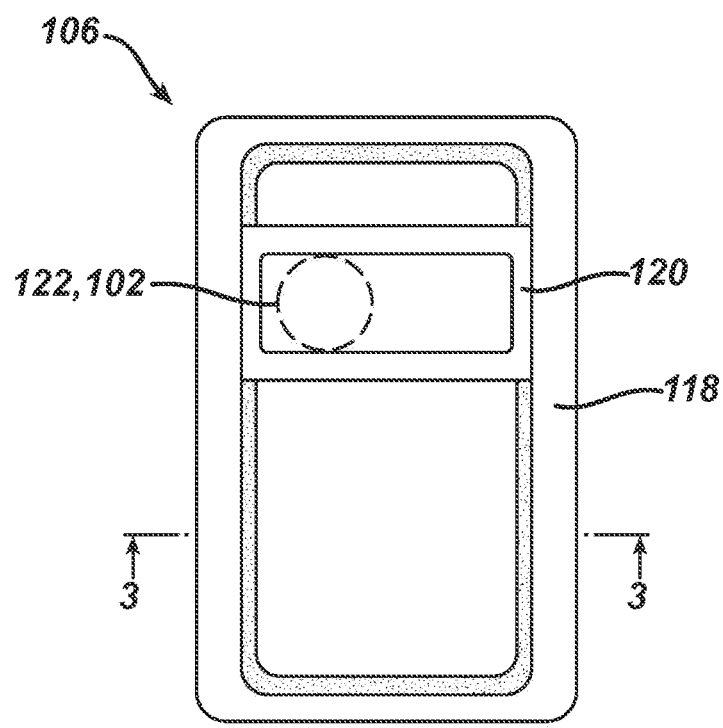
FIG. 2 is a plan view of a guide member, with a distal end of a medical ultrasound handpiece outlined in phantom lines for context.
Figure 3:
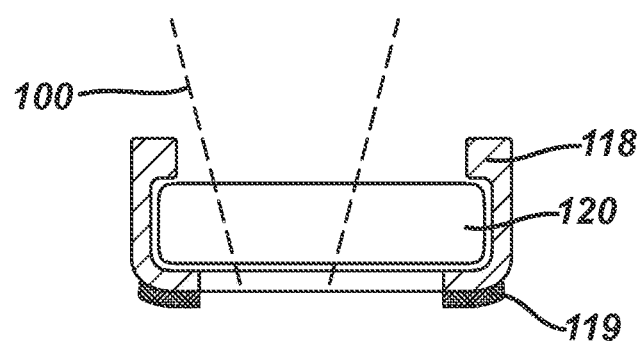
FIG. 3 is a cross-sectional side view of the guide member of FIG. 2, with a medical ultrasound handpiece outlined in phantom lines for context.
Figure 4:
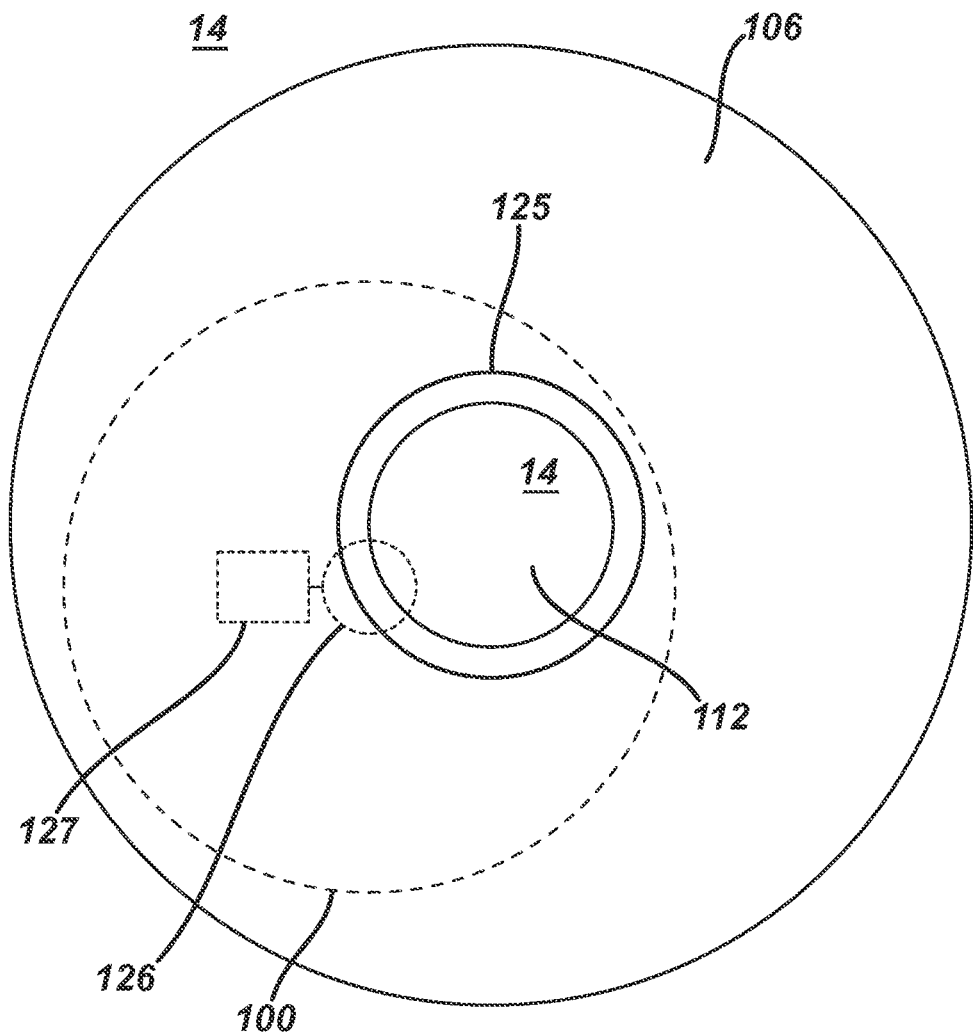
FIG. 4 is a schematic top view of a guide member with a passive wire loop. A medical ultrasound handpiece with an active wire loop is shown in phantom lines for sake of clarity.

In a second expression of the first embodiment, shown in FIGS. 2 and 3, the distal guide member 106 may be a locating base 118 with a slidable, interlocking shuttle member 120. In one construction, the locating base 118 may be adhered to the surface of the skin 14 surrounding the facial feature 10 by an adhesive backing 119. The shuttle member 120 is configured to receive the distal end 102 of the medical ultrasound handpiece 100, which may serve as or provide a repositionable foot 122. The repositionable foot 122 may treat larger areas or long tracks by enabling the sequential treatment of a series of contiguous 'spots' within the facial feature 10. The repositionable foot 122 may be slidably repositioned within the locating base 118 by the user or under computer control. In one construction, the repositionable foot 122 may be detachable from the medical ultrasound handpiece 100. In one variation, the repositionable foot 122 may be a single use, consumable part. In another variation, the repositionable foot 122 may be a reusable, sterilizable part. In an exemplary construction, one of a plurality of repositionable feet 122 having varying thicknesses may be detachably affixed to the ultrasound handpiece 100 to mechanically vary the position of the focusing ultrasound radiator 104 with respect to the distal end 102, and thus the depth at which the predetermined distance d is found within the skin 14. In another exemplary construction, one of a plurality of repositionable feet 122 having varying areal dimensions may be detachably affixed to the ultrasound handpiece 100 to control the application of diffuse ultrasound energy near the focal point to the skin 14. The distal end 102 is slidably engaged with the locating base 118, via the shuttle 120, to position the focal point f within the skin 14.

In a third expression of the first embodiment, the medical ultrasound handpiece 100 includes a registration system 124 configured to monitor the location and/or track of the focal point f with respect to the distal guide member 106. Registration and tracking systems may include: software for tracking instrument position; electrically resonant rings, defined by a passive wire loop 125 (with a load such as a resistor and capacitor connected in series) affixed to the guide member 106 and an active wire loop 126 excited by a radio frequency element 127 mounted in the ultrasound handpiece 100, for proximity warning; magnetic coupling between the ultrasound handpiece 100 and the guide member 106, established in part by loading the guide member 106 with either a high susceptibility material or a permanent magnet material, for proximity warning; an electrical conductivity sensor (not shown), configured to detect the different electrical conductivities of the guide member 106 and the skin 14, for perimeter violation warnings; or a polarization sensor (not shown), configured to indirectly measure the differential electrical susceptibility of tissue prior to and after ultrasonic treatment, for indirectly tracking instrument position (more precisely, prior treatment positions). The guide member 106 may also be designed to have a very different electrical susceptibility so that the polarization sensor may be used for perimeter violation warnings. The delivery of ultrasound energy may be manually or automatically controlled based on the residence time of the ultrasound handpiece 100 over any particular portion of the facial feature 10 as it is moved back and forth across the surface of the skin 14 within the guide member 106. The delivery of ultrasound energy may also be automatically controlled based on measurements of skin characteristics during ultrasound treatment, such as the electrical susceptibility of pre-treatment and post-treatment tissue during the course of a procedure.

In a method of using the expressions of the first embodiment, a dermal filler 12 is injected into the dermis of the facial feature 10, and a distal guide member 106 is placed on the surface of the skin 14 so as to surround the facial feature 10. The dermal filler 12 may be injected before or after placement of the guide member 106. The medical ultrasound handpiece 100 is placed on the guide member 106, and an acoustic gel 16 is applied to the skin 14 over the facial feature 10. The acoustic gel 16 may be applied before or after placement of the ultrasound handpiece 100 on the guide member 106, depending upon the source of the gel, e.g., separate applicator or application via a handpiece port 110 or 114. The distal end 102 of the ultrasound handpiece 100 is engaged with the guide member 106, and slidably translated upon the guide member 106 to position the focal point f of the focusing ultrasound radiator 104 within the injected dermal filler 12, whereupon the ultrasound radiator 104 is powered to shear-thin the dermal filler 12. In one variation of the method, the ultrasound handpiece 100 is removed from engagement with the guide member 106 and the dermal filler 12 is manipulated from the surface of the skin 14 while in a shear-thinned state. In another variation of the method, both the ultrasound handpiece 100 and the guide member 106 are removed from the skin 14, and the dermal filler 12 is manipulated from the surface of the skin 14 while in a shear-thinned state.

In an implementation of the method, the skin 14 of the facial feature 10 is pulled into the chamber 112 defined by the distal guide member 106 by a partial vacuum. This permits more robust definition of the skin surface plane in the presence of wrinkles, and serves to accurately position the surface of the skin 14 with respect to the focusing ultrasound radiator 104 and focal point f. The focusing ultrasound radiator 104 is subsequently powered to shear-thin the injected dermal filler 12. In another implementation of the method, the skin 14 of the facial feature 10 is placed into tension, and the distal guide member is subsequently adhered onto the tensioned surface of the skin 14. This similarly improves the definition of the skin surface plane, as well as the accuracy of the positioning of the surface of the skin 14 with respect to the ultrasound radiator 104. The ultrasound radiator 104 is subsequently powered to shear-thin the injected dermal filler 12.

A second embodiment of the invention is shown in FIGS. 5-8. The second embodiment includes a medical ultrasound handpiece 200 having a distal end 202, a distal rolling member 206 for placement over a facial feature 10, and a focusing ultrasound radiator 204 mounted proximally from the distal end 202. The ultrasound radiator 204 is configured to create a beam of ultrasound energy having a focal point, f, at a predetermined distance, d, as otherwise described in the context of the first embodiment.

Figure 5:
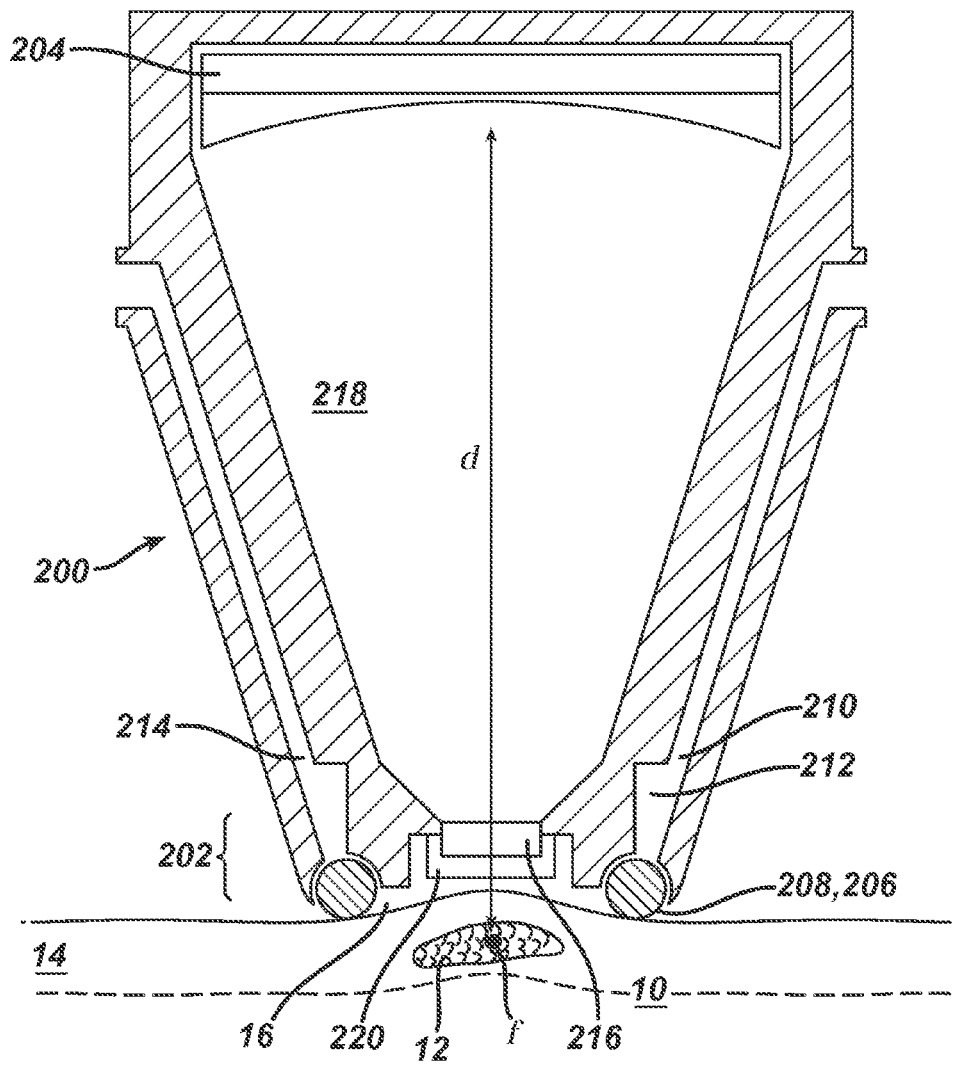
FIGS. 5 and 6 are schematic side views of medical ultrasound handpieces.

In a first expression of the second embodiment, shown in FIGS. 5 and 6, the distal rolling member 206 may be a ring of bearings 208, e.g., roller bearings or ball bearings, disposed at the distal end 202 to facilitate motion across the surface of the skin 14. The distal end 202 of the medical ultrasound handpiece 200 includes an acoustic head 216 coupled to the focusing ultrasound radiator 204 through an internal acoustic coupling medium 218 such as a fluid or gel. The acoustic head 216 is preferably constructed from polysulfone, REXOLITE® (a thermoset material produced by crosslinking polystyrene with divinylbenzene, marketed by C-LEC Plastics of Willingboro, N.J.) or "LOTEN" (marketed by Sigma Transducers of Kennewick Wash.). Regardless of the material used, the acoustic impedance of the acoustic head 216 should be within a factor of 5 of the acoustic impedance of water, $1.5 \times 10^6$ kg/m$^2$*sec. Additional construction details intended to minimize the reflection of ultrasound energy are known within the art. See, e.g., U.S. Pat. Nos. 6,082,180 and 6,666,825. In one construction, the acoustic head 216 includes a separable interfacial boot 220 configured to shield the acoustic head 216 from contact with the surface of the skin 14. The interfacial boot 220 is preferably constructed from silicone, since it provides a reasonable impedance match and is biocompatible for patient contact. Functionally, silicone may also be stretched across the acoustic head 216 by the user for a tight, gapless fit. The interfacial boot 220 may be treated as a single use, consumable part or a reusable, sterilizable part. In another construction, a partial vacuum may be applied to the skin 14 proximate the distal end 202 by a vacuum manifold 212 to enhance contact between the acoustic head 216 and the skin 14. In this or other constructions, the distal end 202 may be supplied with an acoustic gel 16 through the vacuum manifold 212 or through a fluid port 214 disposed proximate the acoustic head 216. In one variation, the ultrasound handpiece 200 may include both a vacuum manifold 212 and a fluid port 214, with the fluid port 214 being located circumferentially oppositely from a vacuum source 210 within the vacuum manifold 212.

Figure 7:
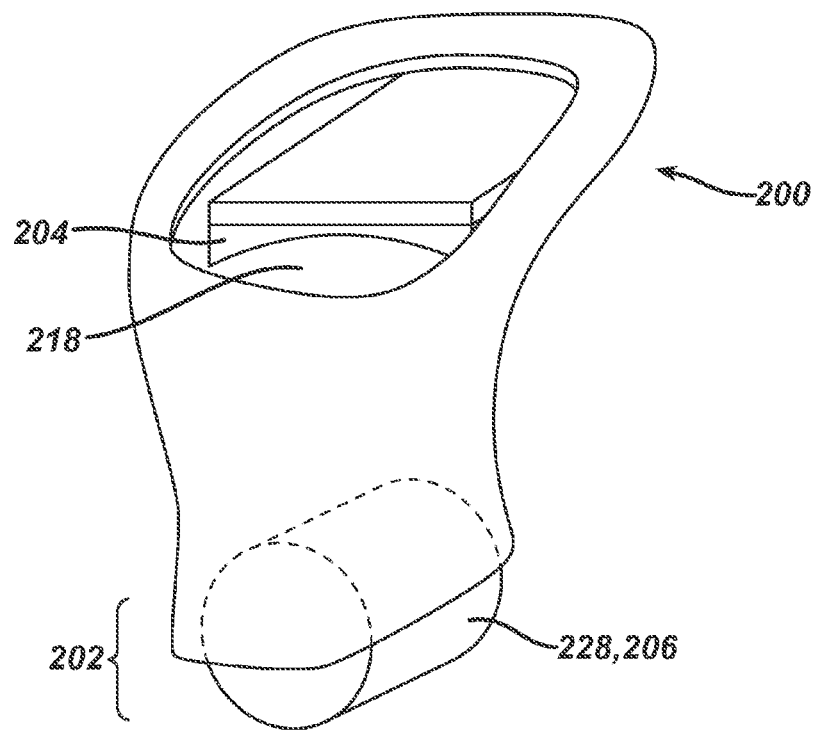
FIG. 7 is a perspective, cut-away view of a medical ultrasound handpiece with a distal rolling member or "ball." Obscured portions of the ball are outlined in phantom lines, and mounting structure, electrical connections, etc., have been omitted.
Figure 8:
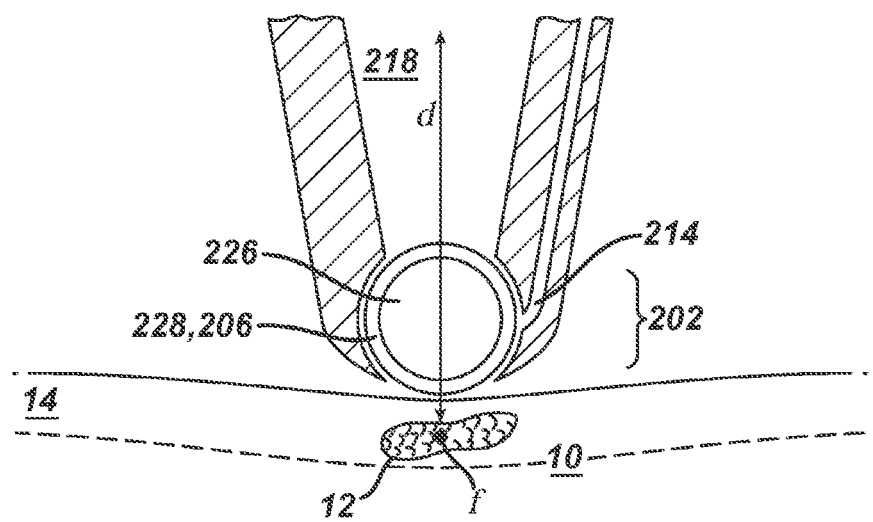
FIG. 8 is a schematic, side detail view of a distal end and distal rolling member.
Figure 9:
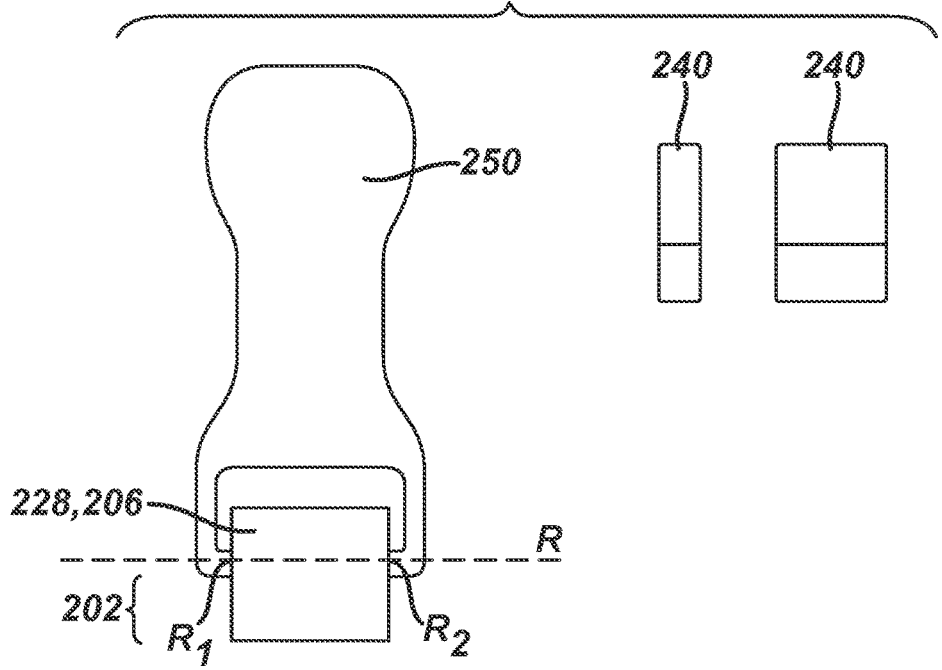
FIG. 9 is a front view of a medical ultrasound handpiece, as well as multiple rings for attachment to a distal rolling member or "ball."
Figure 10:
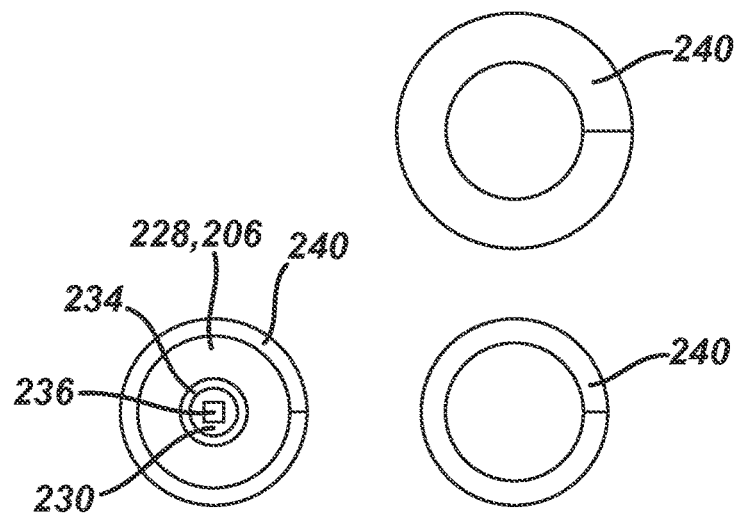
FIG. 10 is a side view of the "ball" of FIG. 9, as well as multiple rings for attachment to the "ball."
Figure 11:
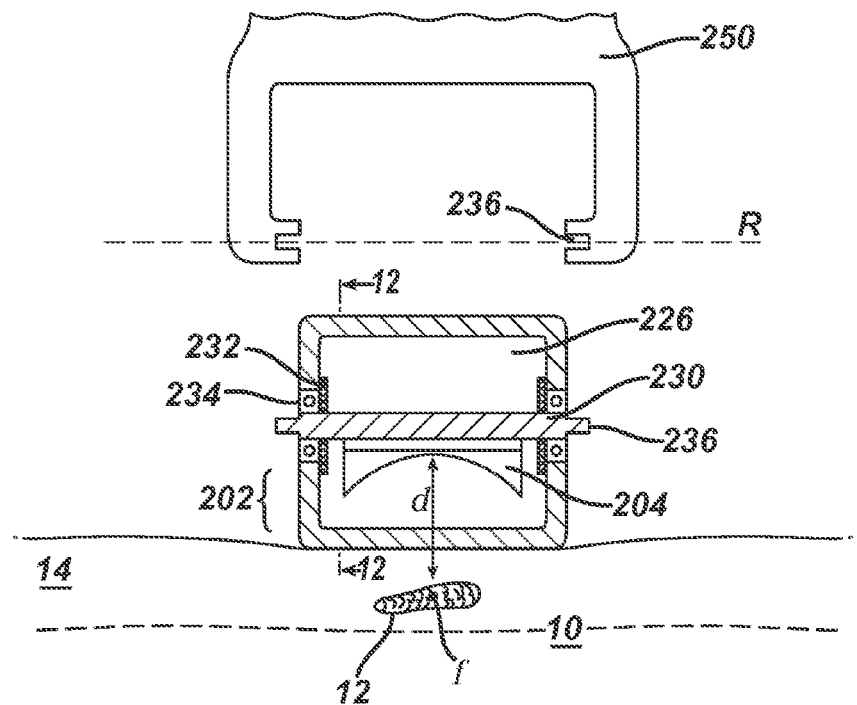
FIG. 11 is a partially exploded, cross-sectional front view of the "ball" of FIGS. 9 and 10.
Figure 12:
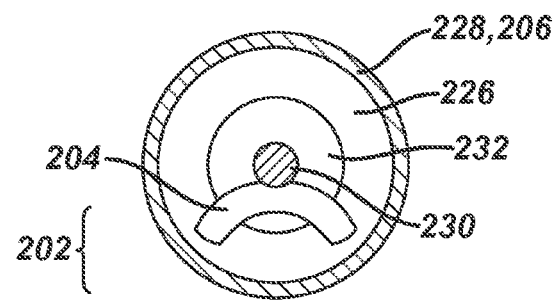
FIG. 12 is a cross-sectional side view of the "ball" of FIGS. 9-11.
Figure 13:
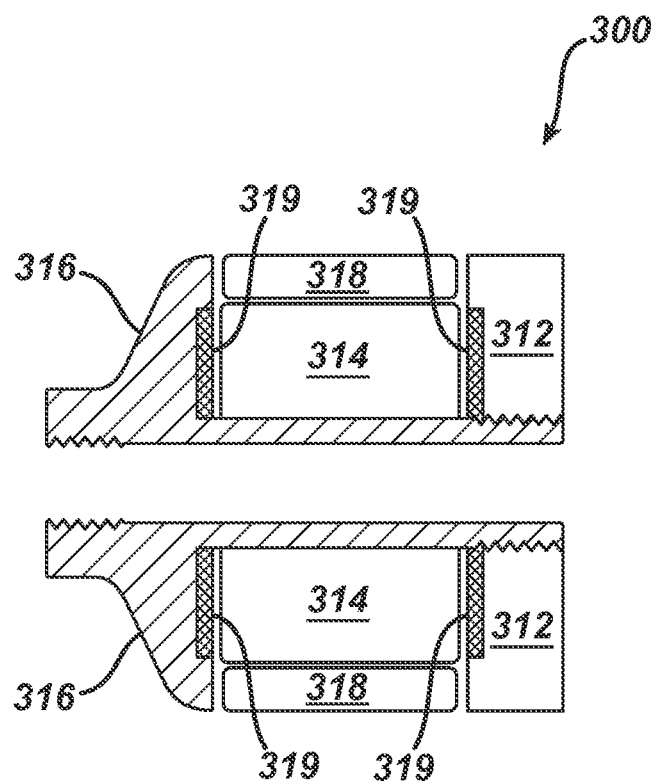
FIG. 13 is a schematic side view of a transducer structure in a medical ultrasound handpiece.

In a second expression of the second embodiment, shown in FIGS. 7 and 8, the distal rolling member 206 may be a cylinder or a generally smoothly curved volume of rotation 228, e.g., truncated ellipsoids, semi-ellipsoids, spheres, and the like, hereinafter generalized under the term "ball," disposed at the distal end 202. The ball 228 is externally coupled to the focusing ultrasound radiator 204 through an acoustic coupling medium 218 generally contained within the medical ultrasound handpiece 200. In one construction, the ball 228 may be formed from an acoustically transparent material. In another construction, the surfaces of the ball may be internally coupled through an acoustic coupling fluid or gel 226 contained within the ball 228. In one construction, acoustic gel 16 may be dispensed from within the ultrasound handpiece 200 as a coating on the surface of the ball 228 for use as a lubricant and acoustic coupling medium between the exposed surface of the ball 228 and the surface of the skin 14. In another construction, acoustic gel 16 may be dispensed onto the ball 228 through a separate fluid port 214 at the distal end 202.

In a third expression of the second embodiment, shown in FIGS. 9-12, the distal rolling member 206 may also be a ball 228. However, the ball 228 may be mounted to the medical ultrasound handpiece 200 for rotation about a predetermined axis, R. The ball 228 in fact serves in part as the distal end 202 of the medical ultrasound handpiece 200, with the focusing ultrasound radiator 204 being located within the ball 228 and the ball 228 being internally coupled to the ultrasound radiator 204 through an acoustic coupling fluid 226 contained within the ball 228. The ball 228 may include a stator 230 extending between the axial ends, $R_1$ and $R_2$, of the axis of rotation of the ball 228, one or more seals 232 disposed about the interface between the stator 230 and the axial ends $R_1$ and $R_2$ and, optionally, bearings 234 disposed at the interface between the stator 230 and the axial ends $R_1$ and $R_2$. The ultrasound radiator 204 is mounted to the stator 230, which may be fixed or user-adjustably fixed in orientation with respect to a handle portion 250 of the ultrasound handpiece 200. In one construction, the stator is fixed in orientation with respect to the handle by a pin-and-plug connection 236 between the stator 230 and the handle portion 250. In another construction, the stator is user-adjustably fixed in orientation with respect to the handle portion 250 by a pin-and-plug connection 236 in which the pin and plug (illustrated for exemplary purposes as rectangular projections and voids) may be conformably interconnected together in any of a plurality of positions. In one variation, the handle portion 250 may be a single use, consumable part. In another variation, the handle portion 250 may be a reusable, sterilizable part.

In an implementation of the third expression, a ring 240 of material may be removably attached to the ball 228. The ring 240 serves as a rotating patient-contact surface. In one variation, the ring 240 may be a single use, consumable part. In another variation, the ring 240 may be a reusable, sterilizable part. In one exemplary construction, one of a plurality of rings 240 having varying material thicknesses may be removably attached to the ball 228 to mechanically vary the position of the focusing ultrasound radiator 204 with respect to the distal end 202, and thus the depth at which the predetermined distance d is found within the skin 14. In another exemplary construction, one of a plurality of rings 240 having varying widths may be removably attached to the ball 228 to mechanically limit the transmission of diffuse ultrasound energy from the ball 228 to portions of the skin 14 adjacent to a linear facial feature 10.

In a method of using the expressions of the second embodiment, a dermal filler 12 is injected into the dermis of the facial feature 10, and the distal rolling member 206 is placed on the surface of the skin 14 over the facial feature 10. An acoustic gel 16 may be applied to the skin 14 over the facial feature 10 before or after placement of the distal rolling member 206 on the skin 14, depending upon the source of the acoustic gel, e.g., separate applicator, application via a handpiece port 214, or transfer from the surface of the distal rolling member 206. The distal rolling member 206 is rollingly translated over the skin 14 to position the focal point f of the focusing ultrasound radiator 204 within the injected dermal filler 12, whereupon the ultrasound radiator 204 is powered to shear-thin the dermal filler 12. In one variation of the method, ultrasound radiator 204 is depowered and the distal rolling member 206 is further rollingly translated over the skin 14 to manipulate the dermal filler from the surface of the skin 14 while in a shear-thinned state. In another variation of the method, the ultrasound handpiece 200 is removed, and the dermal filler 12 is manipulated from the surface of the skin 14 while in a shear-thinned state.

In an implementation of the method relating to the first expression, the skin 14 of the facial feature 10 is pulled against the acoustic head 216 by a partial vacuum. This permits more robust definition of the skin surface plane in the presence of wrinkles, and serves to accurately position the surface of the skin 14 with respect to the focusing ultrasound radiator 204 and focal point f. The focusing ultrasound radiator 204 is subsequently powered to shear-thin the injected dermal filler 12.

A third embodiment of the invention is shown in FIGS. 13-21. The third embodiment includes a medical ultrasound handpiece assembly 300 having an ultrasound transducer 310, which may be configured as a "Langevin stack." A "Langevin stack" generally includes, in order, a first resonator or end-bell 312, a transducer portion 314, and a second resonator or fore-bell 316, as well as various ancillary components such as mounts, intermediate gain stages, and the like which may be interposed between or mounted around components 312, 314, and 316. Examples of ultrasonic surgical instruments with this general configuration are disclosed in U.S. Pat. Nos. 5,322,055 and 5,954,736. The transducer material in the transducer portion 312 may be piezoelectric, but may alternately be magnetostrictive, with a coils 318 and permanent magnets 319 bracketing the transducer material, or electrostrictive. Unless otherwise indicated, illustrations omitting specialized transducer components as the aforementioned coils and magnets should be understood as being generic, schematic representations rather than limiting disclosures. The ultrasound handpiece assembly 300 and ultrasound transducer 310 are coupled to an end effector 320, as further described below. Examples of medical ultrasound handpieces coupled to ultrasonic blades and other surgical end effectors are disclosed in U.S. Pat. Nos. 6,278,218; 6,283,981; 6,309,400; 6,325,811; and 6,423,082, as well as U.S. patent application Ser. No. 11/726,625, entitled "Ultrasonic Surgical Instruments," filed on Mar. 22, 2007, and Ser. No. 11/998,543, entitled "Ultrasonic Surgical Instrument Blades," filed on Nov. 30, 2007, all of which are incorporated by reference herein. The ultrasonic transducer 310 and coupled end effector 320 are preferably an integral number of one-half system wavelengths (n$\lambda$/2) in length. Unless otherwise indicated, illustrations omitting routine components or illustrating partial structures should be understood as being generic, schematic representations rather than limiting disclosures.

The end effector 320 includes, in order, a distal probe tip 322, a probe neck 324, a proximal probe dilation region 326, and an ultrasonically active shaft 328, with the shaft coaxially held within an ultrasonically inactive probe sheath 330 and operatively connected to the dilation region 326. The probe tip 322 is generally rounded or paddle like, but may include a minor distal-most blade portion 323 as described below. The dilation region 326 is configured to have an average outside diameter that is equal to or larger than the average outside diameter of the probe tip 322, as well as that of probe neck 324. The probe sheath 330 is configured to have an outside diameter that is approximately equal to the outside diameter of the dilation region 326. The dilation region 326 is positioned at a proximal anti-node 332, and is used to dilate the surface of the skin 14 so that the insertion force associated inserting with the probe sheath 330 under an initial perforation is minimized. A small initial hole, formed by probe tip 322 or another instrument, followed by reversible dilation appears to create the smallest long term hole in the surface of the skin 14. The end effector should emit about 1 to 20 watts of effective power, but may have an instantaneous requirement of up to about 30 watts during penetration of the skin 14. It is important to note that while dermal filler procedures are a primary application for such devices due to post-surgical cosmetic concerns, the devices may also advantageously be scaled for use in deep blunt dissection or sculpting procedures where the snagging of the probe sheath 330 on tissue surfaces during an insertion transition from the device blade/probe 322-326 to the probe sheath 330 is a concern.

In a first expression of the third embodiment, shown in FIG. 14, the probe dilation region 326 is located proximate the first anti-node 332 proximal from the probe tip 322. In variations of the first embodiment, the dilation region could be located proximate an even more proximal anti-node. In one construction, the junction between the dilation region 326 and the ultrasonically inactive probe sheath 330 (when the end effector 320 is closed) may be located at a node 334 proximal from the anti-node 332. This allows for a very tight junction, which minimizes the likelihood of tissue snagging at the interface between the dilation region 326 and the probe sheath 330. In another construction, the junction between the dilation region 326 and the probe sheath 330 (when the end effector 320 is closed) may be located at an anti-node 332. The junction is preferably located at the same anti-node 332 as the transition between the probe neck 324 and the dilation region 326. The latter construction minimizes ultrasound gain impact, but necessitates a gap between the dilation region 326 and the probe sheath 330. The impact of the gap is somewhat mitigated because the ultrasonically active shaft 328 and dilation region 326 are active at the junction and will tend to self-clean.

In a second expression of the third embodiment, shown in FIG. 15, the distal probe tip 322 may be sharpened to include a distal-most mechanical blade portion 323 to facilitate rapid penetration with minimal thermal spread. The mechanical blade portion 323, while useful to enable rapid skin penetration, is preferably minimized in size and extent to reduce the likelihood that other tissue structures will be inadvertently damaged or disrupted as the probe tip 322 is wanded back and forth to shear-thin, blunt dissect tissue, and/or emulsify fat. Alternately, in a third expression of the third embodiment, illustrated in the topmost example in FIG. 14 and in an end view in FIG. 16, the probe tip 322 may be dull. A dull tip allows the user to safely push the probe tip 322 around in a blunt dissection mode, while initial penetration and dilation of the skin are accomplished with an unpowered needle or an obturator.

In a fourth expression of the third embodiment, shown in FIGS. 17-21, the surface area of the distal probe tip 322 and/or probe neck 324 is increased, while holding the cross-sectional area of the part(s) constant, by configuring at least one of these structures to have an undulating periphery in cross-section. This improves power transfer efficiency into the dermal filler 12 and/or other target tissues. In one construction, illustrated in the bottommost example in FIG. 14 and in an end view in FIG. 17, the probe tip 322 may have a high aspect ratio, with portions of the probe tip 322 being wider than the width of the probe dilation region 326. A high aspect ratio probe tip 322 allows for an increase in the surface area-to-volume ratio of the device, but may be inserted through, or itself create, a small incision-like slit in the surface of the skin 14. Such constructions are intended to be within the scope of devices where the dilation region 326 has an average outside diameter that is equal to or larger than the average outside diameter of the probe tip 322. In another construction, shown in FIGS. 18 and 19, a portion of the probe neck 324 may be configured to include a plurality of longitudinally extending, circumferentially arrayed slats 324a with openings 324b to an internal lumen 331. The slats 324a may be have a sheet-like cross-sectional profile, or may be configured to include one or more externally protruding structures, such as ribs 324c, in order to increase the surface-area-to-volume ratio of the device. In yet another construction, shown in FIGS. 20 and 21, portions of the distal probe tip 322 and/or probe neck 324 may be configured as a solid rod defining a plurality of longitudinally extending, circumferentially arrayed ribs 324c alternating with plurality of similarly disposed indentations 324d. In one modification of the latter construction, a proximal portion of the probe neck 324 may be configured to provide an internal lumen 331 in fluid communication with the indentations 324d for the injection and/or withdrawal of fluid material proximate the probe tip 322.

Finally, it is important to note that in various constructions, and as illustrated in middle example of FIG. 14, the end effector 320, and particularly the probe tip 322 and/or probe neck 324, may be axisymmetric or axially asymmetric, so that the term diameter should be understood generally as referring to the characteristic width of the referenced part, rather than a geometric diameter determined with respect to a single central longitudinal axis.

Figure 22:
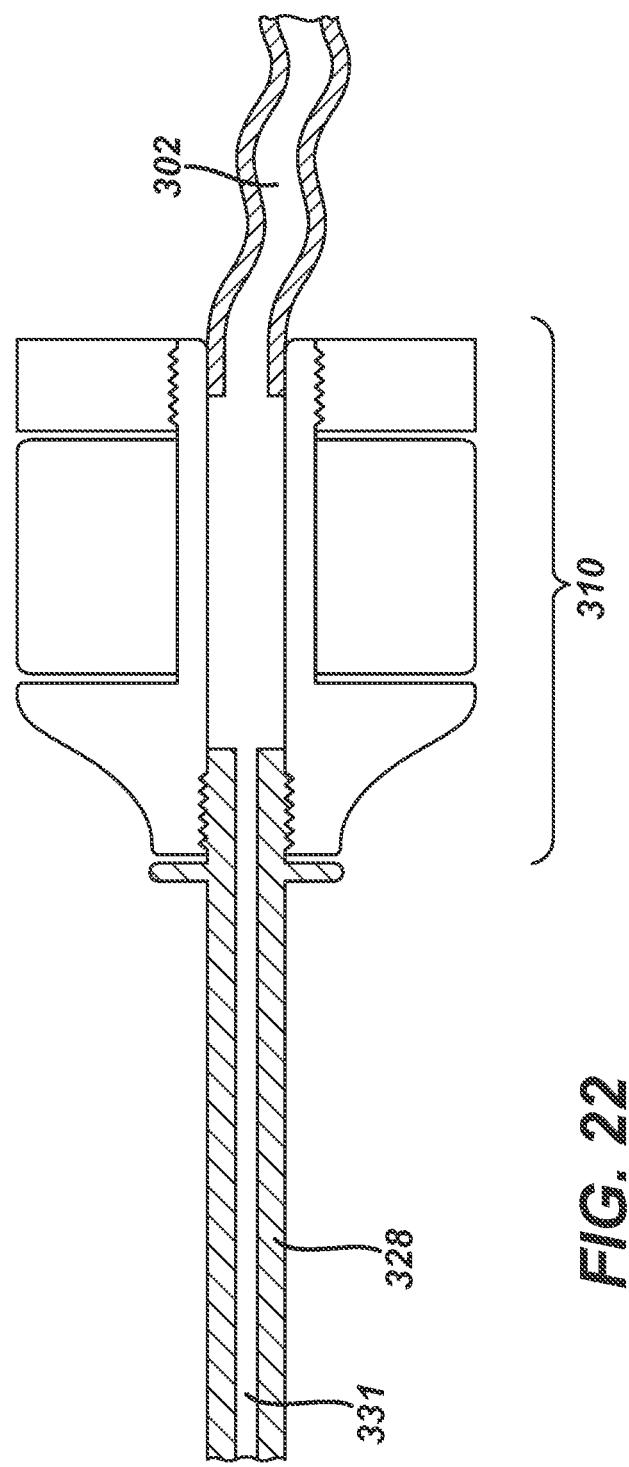
FIGS. 22-24 are schematic side views of aspects of a medical hand piece assembly relating to fluid communications configurations.
Figure 23:
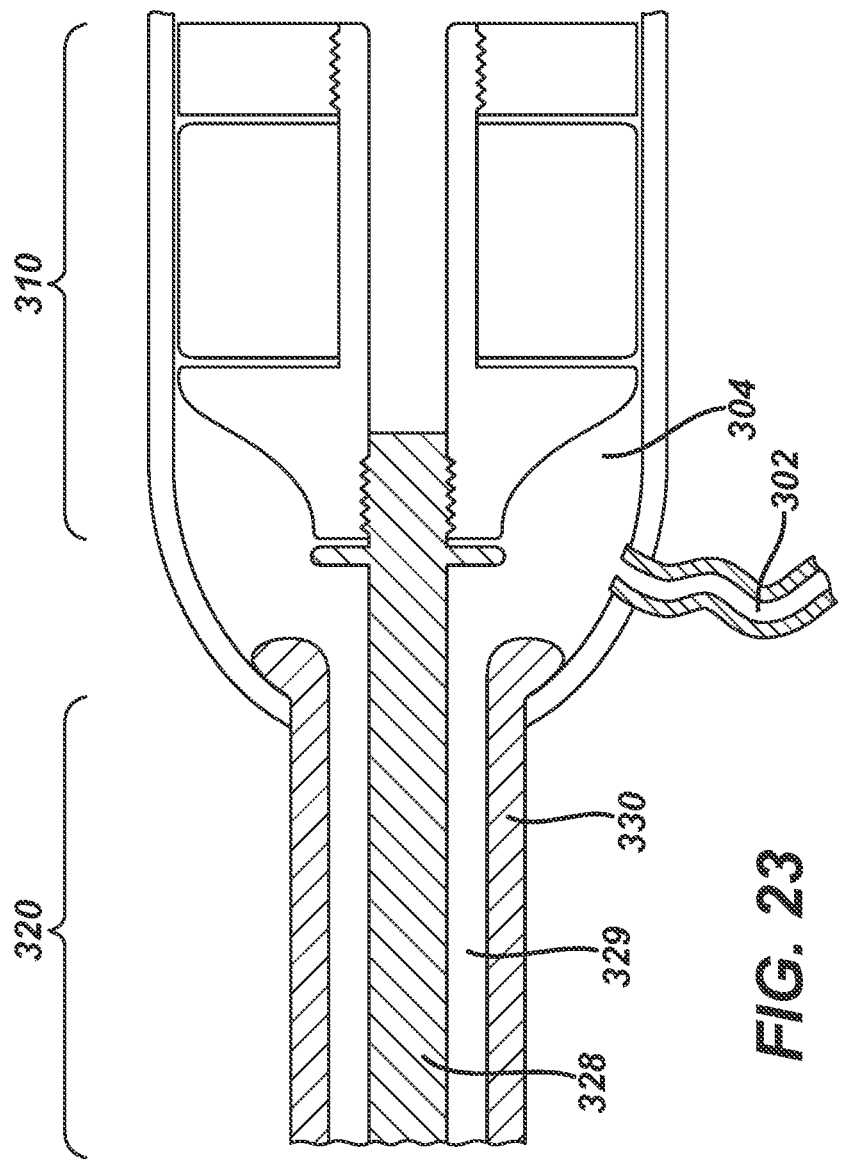

In a fifth expression of the third embodiment, the medical ultrasound handpiece assembly 300 is configured to shear-thin or fluidize a material transiting within one more lumens in the end effector 320. The challenge of injecting precise amounts of dermal filler in a precise location along a facial feature 10, such as the nasolabial fold, increases as the viscosity of the dermal filler increases and the size of the injection needle lumen decreases. Ultrasonic energy may be used to shear-thin the dermal filler while the dermal filler passes from a reservoir on the surgical instrument and through a lumen in the end effector 320. Ultrasonic energy may also be used to shear-thin the dermal filler or to fluidize other materials while those materials are transiting within the end effector 320. Ultrasound handpiece assembly 300 consequently may include at least one fluid lumen 302 in fluid communication with the end effector 320. In one construction, ultrasonically active shaft 328 includes an internal lumen 331, with fluid lumen 302 in fluid communication with internal lumen 331. In one exemplary construction, shown in FIG. 22, shaft 328 is secured to ultrasound transducer 310, which may be configured as a "Langevin stack" with an integrated fluid path. In another construction, the interstitial space 329 between ultrasonically inactive probe sheath 330 and shaft 328 serves as a fluid lumen, with fluid lumen 302 in fluid communication with the proximal end of probe sheath 330 and interstitial space 329. In one exemplary construction, shown in FIG. 23, a fluid lumen 302 bypasses the ultrasound transducer 310 within the handpiece assembly 300 and joins a manifold 304 receiving the proximal end of probe sheath 330 upon assembly of the end effector 320 with the handpiece assembly 300. In one variation, the internal lumen 331 is used to suction material from the distal end of the end effector 320, and the interstitial space 329 is used to inject materials such as dermal filler or irrigation fluids. In another variation, the internal lumen 331 is used to inject materials such as dermal filler or irrigation fluids, and the interstitial space 329 is used to suction material from the distal end of the end effector 320. In other variations, only one structure may serve as a fluid lumen, and both functions may take place through that lumen. Where the interstitial space 329 is used as a fluid lumen, the end effector may be opened by retracting the probe sheath 330 from the dilation region 326. Adjustment mechanisms for retracting the probe sheath 330 are described in detail in the context of the fourth embodiment of the invention, described below.

Figure 24:
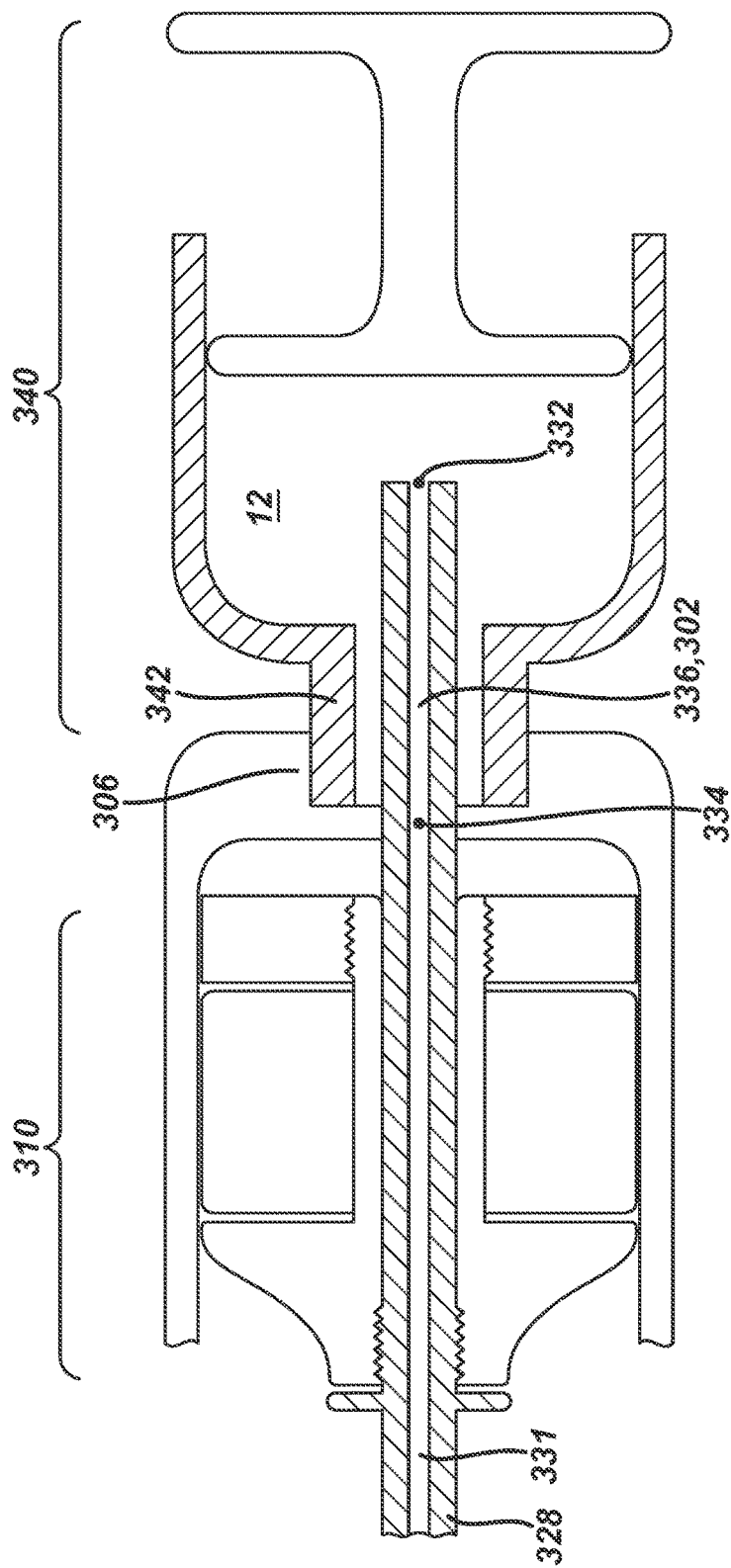

In an implementation of the fifth expression, shown in FIG. 24, ultrasonically active shaft 328 includes an oppositely projecting portion 336 serving as the fluid lumen 302. Portion 336 projects from a proximal end of the ultrasound transducer 310 and within a handpiece port 306 configured for connection to a syringe 340 via, e.g., a complementary-configured port 306 and syringe tip 342 such as those in found luer lock connections. Portion 336 projects within at least the syringe tip 342, whereupon ultrasound energy transmitted to portion 336 during operation of ultrasound transducer shear-thins dermal filler held within syringe 340. The handpiece port 306 is preferably located at a node 334 of the projecting portion 336. The free end of the projecting portion 336 is preferably located at an anti-node 332 so as to maximize shear-thinning at the entrance of the comparatively narrow-bore fluid lumen 302. In other implementations, syringe 340 may be combined within the handpiece assembly 300 as a unit, so that port 306 is an internal point of connection to an integrated syringe structure.

In a method of using the expressions of the third embodiment, a dermal filler 12 is injected into the facial feature 10, and at least the distal probe tip 322 of the device is inserted beneath the surface of the skin 14. The dermal filler 12 may be injected before or after insertion of the distal probe tip 322 within the skin, depending upon the source of the dermal filler, e.g., separate applicator or injection through a fluid lumen of the end effector 320 (such as interstitial space 329 or internal lumen 331). Also, the probe tip 322 may be inserted through an existing perforation in the skin 14 (such as made by an applicator or obturator) or through a perforation made by a distal-most blade portion 323 of the probe tip 322. The ultrasound transducer 310 is powered to operate the probe tip 322, and the probe tip is inserted into the dermal filler 12 to shear-thin the filler. In one variation of the method, the ultrasound transducer 310 is depowered and the dermal filler 12 is manipulated from the surface of the skin 14 while in a shear-thinned state. In another variation of the method, the ultrasound transducer 310 is depowered and the probe tip 322 withdrawn from the skin, whereupon the dermal filler 12 is manipulated from the surface of the skin 14 while in a shear-thinned state.

In a preferred implementation of the method, the probe dilation region 326 is inserted beneath the surface of the skin 14 after the ultrasound transducer 310 is powered, whereupon the ultrasonically inactive probe sheath 430 is inserted beneath the skin to protect the surface of the skin 14 from unintended contact with ultrasonically active portions of the probe. Ultrasound transducer 320 may be depowered prior to removal of the probe sheath 430, dilation region 326, and probe tip 422 to further protect the surface of the skin 14. In a variation of the implementation possible where separate instruments provide initial penetration and dilation of the skin, the dilation region 326 is brought into contact with the surface of the skin, whereupon the ultrasound transducer 320 is powered and the dilation region 326 and probe sheath 430 are inserted beneath the skin.

In another method of using the expressions of the third embodiment, the devices may be used to perform blepharoplasty. The distal probe tip 322 is inserted beneath the surface of the skin above a periorbital fat pad. Although the probe tip 322 may be inserted through an existing perforation in the skin 14 (such as made by an obturator), the skin is preferably perforated by a distal-most blade portion 323 of the probe tip 322. The ultrasound transducer 310 is powered to operate the probe tip 322 and to advance the distal probe tip 322 into the periorbital fat pad. Advantageously, devices scaled for typical dermal filler procedures are also suitably scaled for blepharoplasty, such that the probe dilation region 326 and the ultrasonically inactive probe sheath 330 may be inserted beneath the surface of the skin 14 during advancement of the distal probe tip 322. This isolates the skin 14 from prolonged contact with ultrasonically active portions of the probe. Upon reaching the interior of the periorbital fat pad, the distal probe tip 322, and potentially a distal portion of the probe neck 324, is manipulated within the periorbital fat pad while the ultrasound transducer 310 is powered to fluidize and shift or lyse and remove periorbital fat. The distal probe tip 322 may also be used to shear-thin a dermal filler 12 that has been injected into the periorbital fat pad in order to further shape the pad, or to inject a dermal filler 12 to take the place of previously removed fat.

A fourth embodiment of the invention is shown in FIGS. 25-33. The fourth embodiment is substantially similar to the third embodiment, as heretofore described, but omits the probe dilation region 326, and consequently the junction between the ultrasonically inactive probe sheath 330 and the dilation region 326. In the referenced figures, elements with reference numbers differing only in the lead digit, e.g., distal probe tips 322 and 422, should be understood to be similar or identical to those elements described in the context of the third embodiment, but for the above-indicated points of distinction. With specific regard to the fourth embodiment, ultrasonically active shaft 428 is coaxially held within the ultrasonically inactive probe sheath 430 and operatively connected to the probe neck 424. The probe sheath 430 is configured such that the distal end of the probe sheath 430 is slidably operable to both cover and expose at least the probe tip 422. It is important to note that in some procedures, dermal fillers are injected substantially below the dermis, particularly at or above the interface between the musculature and the periosteum in order to alter facial features such as the jaw line. Consequently, some expressions of the embodiment are adapted for use in this application, or similar microsurgical procedures in which ultrasonic instruments are used to inject material, remove material, or dissect tissues at very precise locations.

Figure 25:
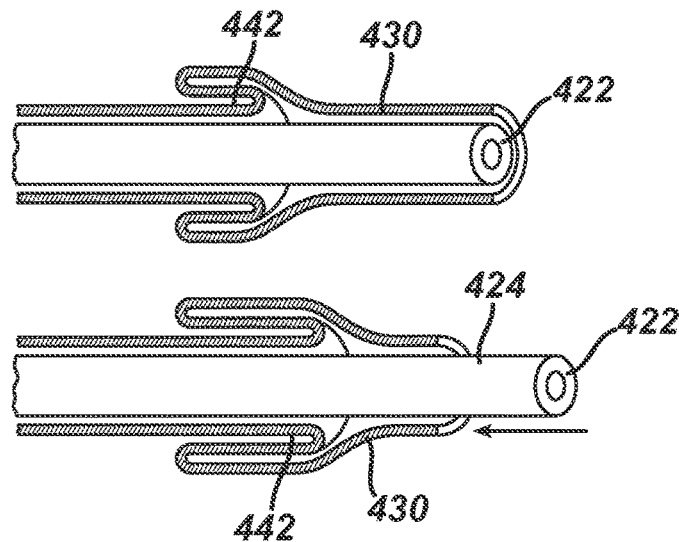
FIG. 25 is a cut-away side view of a probe sheath retraction mechanism.

In a first expression of the fourth embodiment, shown in FIG. 25, at least a portion of the ultrasonically inactive probe sheath 430 is longitudinally flexible and includes an S-shaped crease 442. The crease 442 allows the distal end of the probe sheath 430 to slidably retract in response to a longitudinal resistance to the advancement of the probe sheath 430. Specifically, portions of the probe sheath 430 distally adjacent to the crease 442 may slide proximally over the crease 442, and ultimately be folded under successive distally adjacent portions of the sheath, in response to sufficient and continued longitudinal resistance to advancement. This folding action causes the probe sheath 430 to retract relative to the ultrasonically active portions of the probe, exposing greater lengths of the probe tip 422 and probe neck 424. The stiffness of the probe sheath 430 may be adapted such that portions of the probe sheath 430 distally adjacent to the crease 442 will not fold into the crease as the probe tip 422 and probe sheath 430 are advanced into soft tissue, but will fold into the crease when the probe tip 422 is advanced into stiff tissue such as muscle or hard tissue such bone. The stiffness may also be adapted solely with respect to hard tissue. Soft tissues proximate the insertion track can then be substantially protected from ultrasonically active portions of the probe both during and after advancement of the probe.

Figure 26:
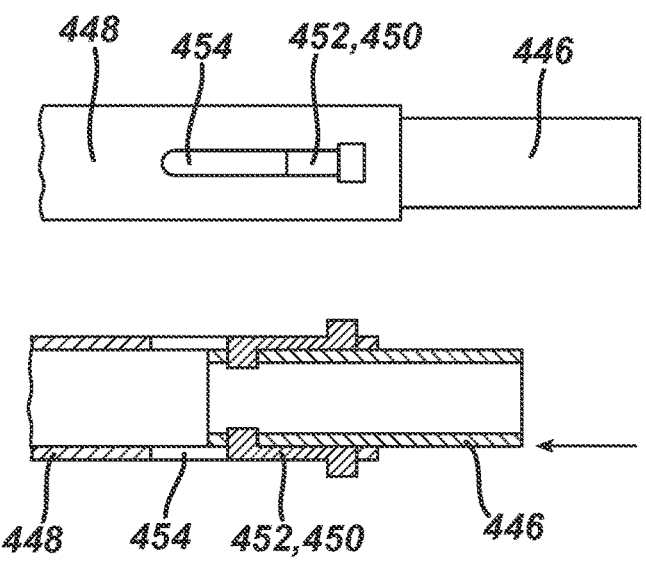
FIG. 26 combines an edge view ("Before") and cross-sectional top view ("After") to illustrate another probe sheath retraction mechanism.

In a second expression of the fourth embodiment, shown in FIG. 26, the distal end of the ultrasonically inactive probe sheath 430 includes a spring-biased mechanism 450 configured to normally extend a distal-most segment 446 of the probe sheath 430 out from a proximally adjoining segment 448, but slidably retract the distal-most segment 446 in response to sufficient longitudinal resistance to the advancement of the probe sheath 430. In one construction, the spring-biased mechanism 450 includes at least two circumferentially opposing elastic dogbones 452 having opposing ends anchored to the distal-most segment 446 and the proximal segment 448, respectively. Preferably, the elastic dogbones 452 are configured to stretch within longitudinal slots 454 of the proximal segment so that interference between the proximal ends of the dogbones 452 and the proximal ends of the longitudinal slots 454 limits the travel of the distal-most segment 446 In modifications of the construction, other structures such as internal stops in the interior of the proximal segment 448, external stops on the exterior of distal-most segment 446, and longitudinal grooves in the proximal end of the distal-most segment 446 may serve as travel limiting structures. In other constructions, coil springs or volute springs may be used with various combinations of anchorings, slots, and stops.

The spring force of the spring-biased mechanism 450 may be adapted such that the distal-most segment 446 will not appreciably expose proximal portions of the probe tip 422 as it is advanced into soft tissue, but will operate when the probe tip 422 is advanced into stiff tissue such as muscle or hard tissue such bone. Soft tissues proximate the insertion track can then be substantially protected from the ultrasonically active portions of the probe both during and after advancement of the probe. The probe sheath 430 and sheath segments 446, 448 are constructed from a comparatively rigid material, and preferably constructed from thermoplastic materials such as ULTEM® (a polyetherimide marketed by SABIC Americas, Inc. of Houston, Tex.), fiber reinforced composites (e.g., pultruded glass or carbon fiber tubing), or braided catheter tubing.

Figure 27:
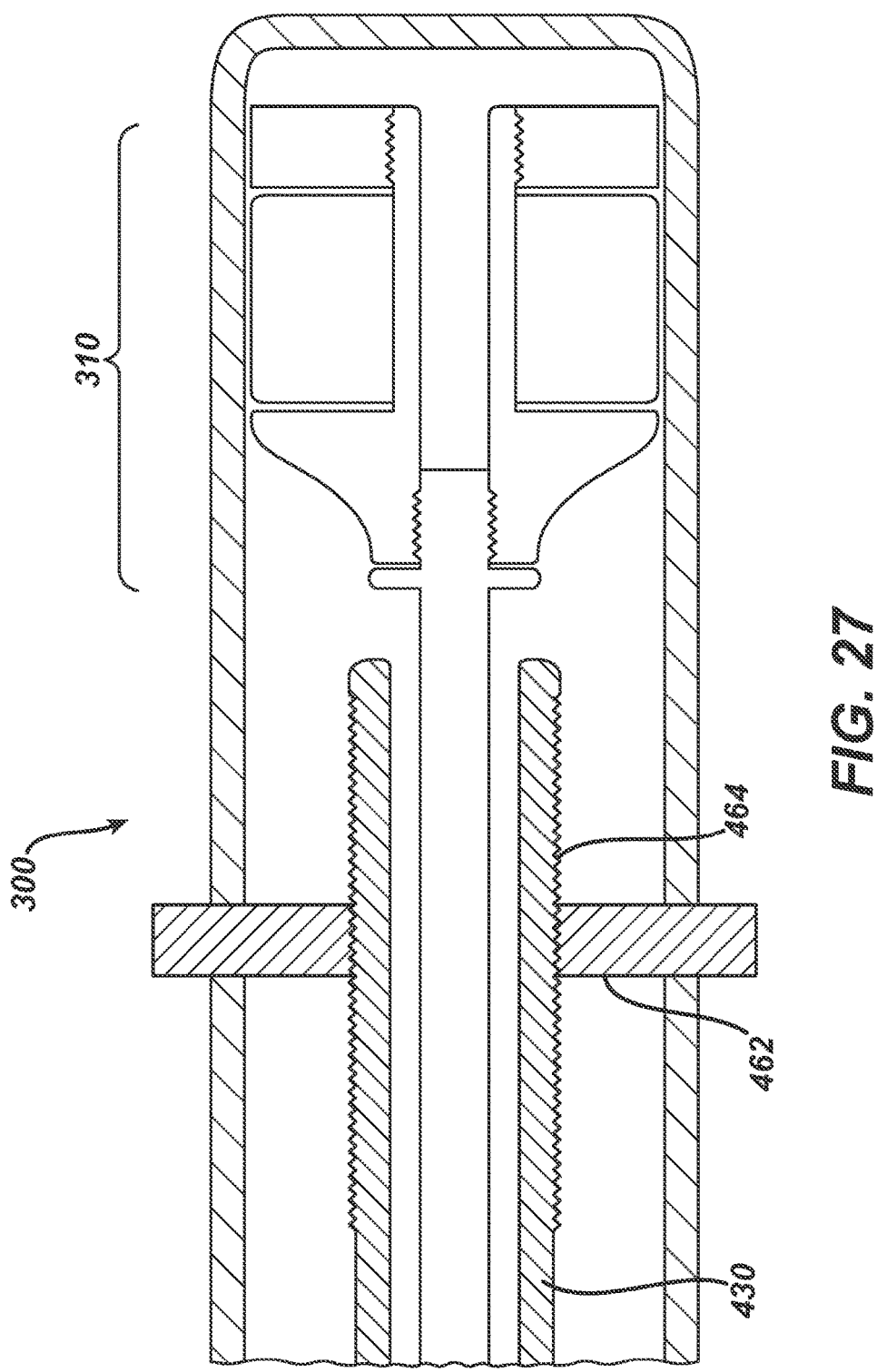
FIGS. 27 and 28 are a schematic side views of medical hand piece assemblies relating to operation of the probe sheath.
Figure 28:
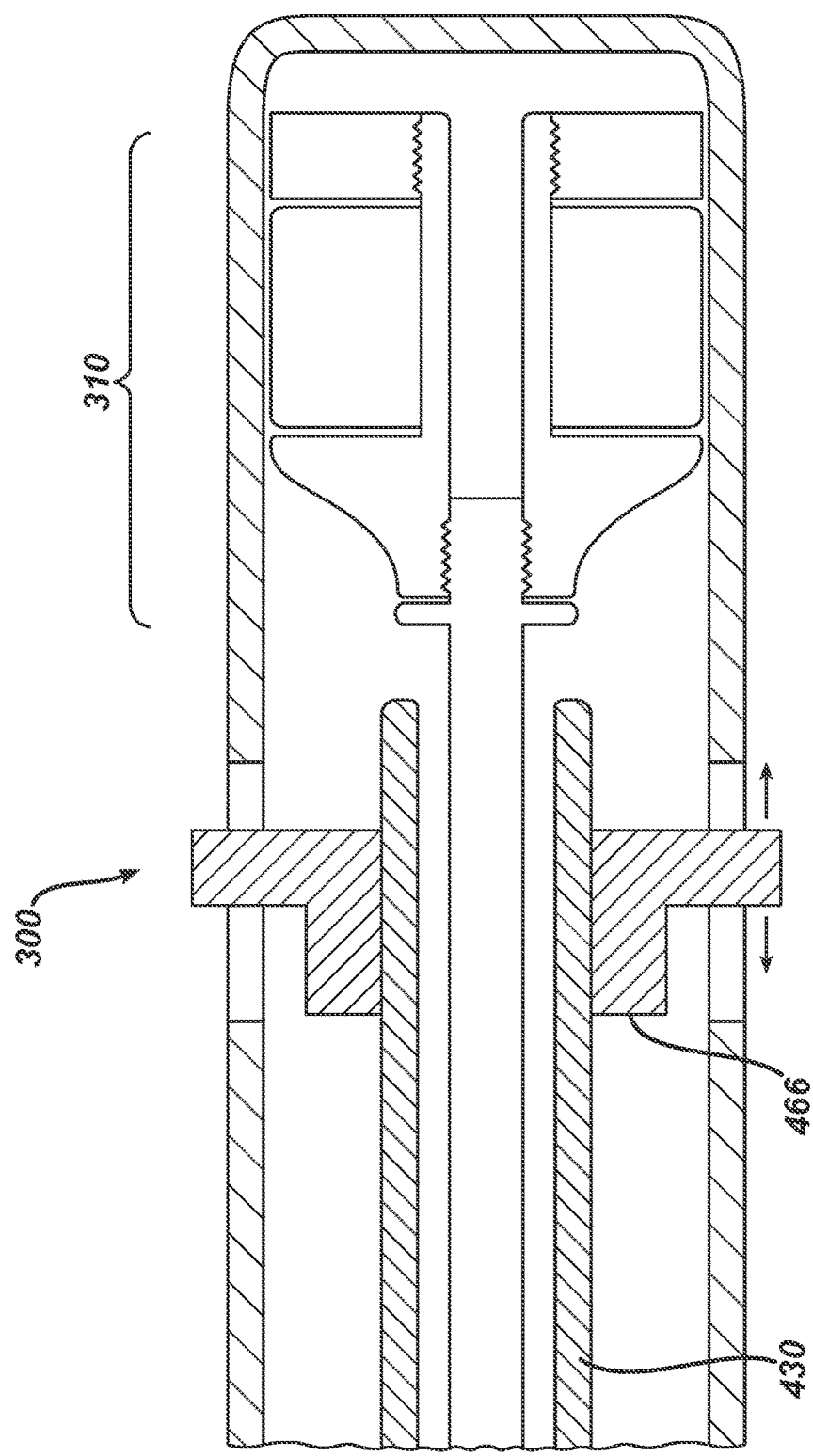

In a third expression of the fourth embodiment, shown in FIGS. 27 and 28, a proximal portion of the ultrasonically inactive probe sheath 430 is coupled to an adjustment mechanism 460 configured to positively position the distal end of the probe sheath 430 over at least the distal probe tip 422. In one construction, the adjustment mechanism 460 includes an internally threaded drive member 462 that couples to external threads 464 on the proximal portion of the probe sheath 430. Such threads may be integral to the proximal portion of the probe sheath 430 or be part of an adapter bound to the proximal portion of the probe sheath 430. In another construction, the adjustment mechanism includes a slide member 466 that is mechanically linked or chemically bound to the proximal portion of the probe sheath 430. The adjustment mechanism is manually or mechanically actuated to slidably operate the distal end of the probe sheath 430 over at least the distal probe tip 422.

The adjustment mechanism is preferably a component of the medical ultrasound handpiece assembly 400. Positive positioning of the distal end of the probe sheath 430 over at least the distal probe 422 from a handpiece assembly enables ready modification of the contact length between tissue and at least the distal probe tip 422 to a length suitable for the intended target. For example, the distal most-end of the probe sheath 430 may be retracted to expose a predetermined length of the probe tip 422 (and potentially the probe neck 424, as further discussed below) corresponding to the spread of tiers in which a dermal filler has been injected. Where a single, small tier has been injected, only a small contact length is needed, with greater contact lengths increasing the risk of unintended tissue damage. Where multiple tiers have been injected, a larger contact length may be desired so as to permit shear-thinning of the entire tiered depth in a single procedure. Finally, in other procedures, and particularly procedures such as liposuction, very large contact lengths may be required into order to employ the surgical device efficiently. For further example, as noted above, dermal fillers may be injected even below musculature in some procedures. Positive positioning of the distal end of the probe sheath 430 over the distal probe tip 422 from the handpiece assembly enables shallower tissues proximate the insertion track, even stiff or tough tissues, to be substantially protected from ultrasonically active portions of the probe after further advancement of ultrasonically active portions of the probe.

Figure 29:
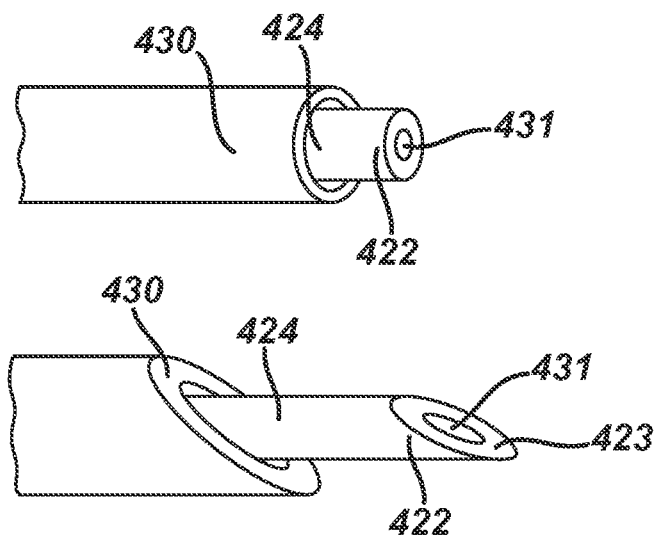
FIGS. 29-31 are perspective views of varying probe configurations.

In implementations of the expressions of the fourth embodiment, shown in FIG. 29, the distal probe tip 422 may be a blunt tip with an opening to an internal lumen 431 continuing through the probe neck 424 and ultrasonically active shaft 428 to establish fluid communication with the handpiece assembly 400. The blunt tip is atraumatic and will tend to stay within structures like fat pockets once it has been introduced. The blunt tip may also be used in other procedures to sculpt bone and cartilage or to remove deposits. Alternately, the probe tip 422 may be a beveled needle tip with a distal-most blade portion 423 and an opening to the internal lumen 431. The needle tip is useful for penetrating tough tissues such as fascia. Probe tip and probe neck configurations such as those described in the context of the third embodiment are envisioned as well. Finally, the distal-most portion of the ultrasonically inactive probe sheath 430 may be blunt, but may alternately be beveled to aid in insertion into soft tissue.

Figure 30:
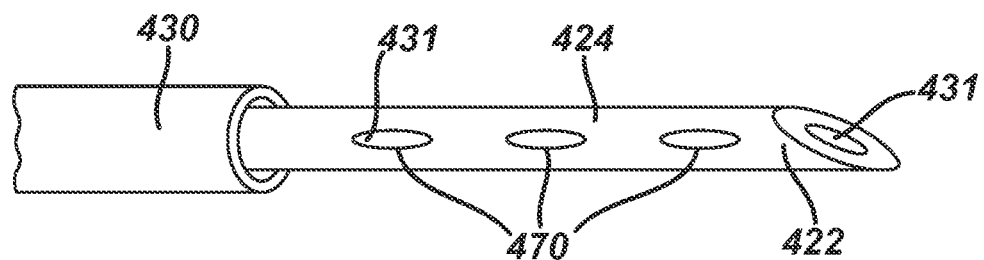
Figure 31:
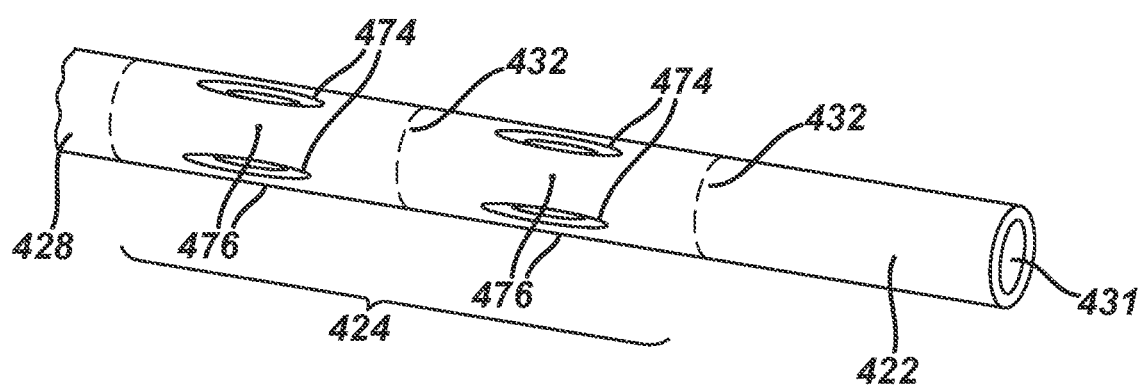
Figure 32:
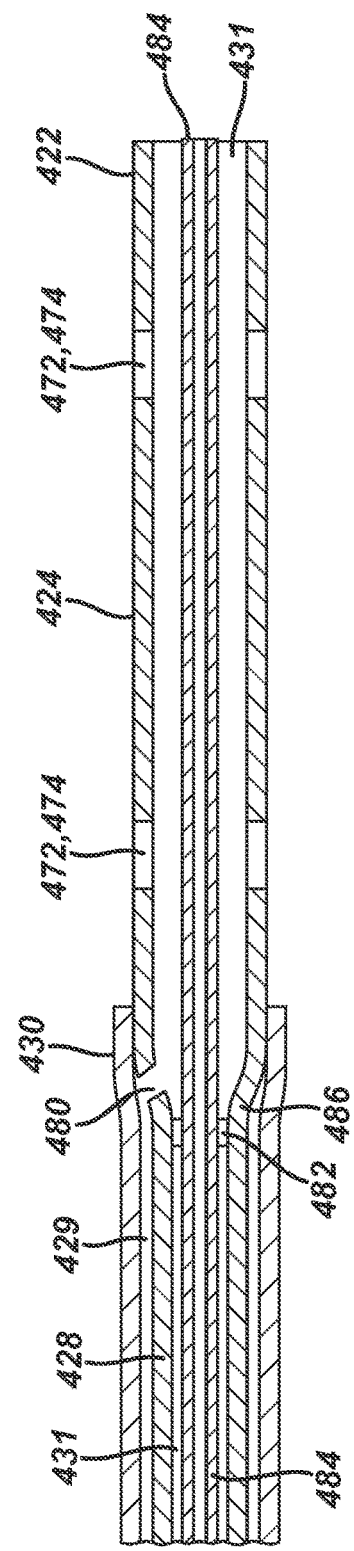
FIG. 32 is a cross-sectional view of a probe configuration including a cannula.

In further implementations of the expressions of the fourth embodiment, shown in FIGS. 30 and 31, the probe neck 424 may include a plurality of slots 470 opening into an internal lumen 431. As indicated earlier, probe tip configurations such as those described in the context of the third embodiment are envisioned as well, so that internal lumen 431 may or may not extend distally into distal probe tip 422. In a first construction, the plurality of slots is configured as a longitudinal array of slots 472. This allows the device to provide additional injection or suction capability along an extended length of the active probe when the probe neck 424 is exposed. In a second construction, the plurality of slots is configured as a plurality of longitudinally elongated, circumferentially arrayed slots 474 alternating with plurality of similarly elongated and disposed bridges 476. The bridges, of course, join proximal and distal portions of the probe neck 424. However, the bridges will also develop a transverse mode of vibration when the probe neck 424 (and ultrasonically active shaft 428 and probe tip 422) are driven longitudinally by the ultrasound transducer 410. The plurality of slots 474 and alternating bridges 476 are preferably located at a node 434. When the bridges 476 experience transverse vibration, proximate dermal filler will be readily shear-thinned. Where tissue removal can be performed, or in other procedures such a liposuction, soft tissues proximate to the bridges 476 will be readily lysed for suction by the end effector 420. The applicants note that in other procedures, the probe sheath 430 may be partially or completely omitted in favor of a separate obturator, with the remainder of the probe scaled to dimensions generally unsuitable for dermal applications. A probe sheath 430, if any, would serve to protect the user from accidental contact with the active portions of the probe 428 at the proximal end of the end effector 420, with a distal end of the end effector being exposed for several inches or more. The longitudinal array of slots 472 may then be configured as a longitudinal array where each longitudinal position in the array includes a plurality of longitudinally elongated, circumferentially arrayed slots 474 alternating with plurality of similarly elongated and disposed bridges 476. The longitudinal positions in the array may correspond to nodes 434. Such a extended-length device may be usefully employed in conventional liposuction procedures occurring essentially within the hypodermis.

In yet further implementations of the expressions of the fourth embodiment, where all of the ultrasonically active shaft 428, probe neck 424, and distal probe tip 422 include an internal lumen 431, and the shaft 428 and ultrasonically inactive probe sheath 430 form an interstitial space 429, a proximal portion of the probe neck 424 may include a lateral aperture 480 for fluid communication between the internal lumen 431 and the interstitial space 429, and a seal 482 disposed proximally from the lateral aperture 480 to seal the internal lumen 431. At least one cannula 484 providing an inner lumen 486 may penetrate the seal 482 and extend distally from the lateral aperture 480. In one variation, the cannula 484 extends distally to the distal probe tip 422. In another variation, the proximal portion of the probe neck 484 is configured as a distally-opening bell 486, with the lateral aperture 480 being disposed in the narrowing portion of the bell. In this variation, the probe sheath preferably seals (generally—the seal does not need to be complete or particularly efficient) against the probe neck 424. The cannula 484 may be used for suction or to inject materials such as dermal filler or irrigation fluids. The distal portion of the internal lumen 431, i.e., that portion distal from the seal 482, may be also be for suction or to inject materials such as dermal filler or irrigation fluids. In a preferred mode of operation, the cannula 484 is used for suction and the internal lumen is used for irrigation. The slots 472 or 474 described previously may present. In the preferred mode of operation, the slots 472 or 474 may serve as irrigation paths to establish a longitudinally-oriented 'flushing circuit' for tissue and tissue debris generated by ultrasonic operation of the probe tip 422 and probe neck 424.

In a method of using the expressions of the fourth embodiment, the distal probe tip 422 of the device is inserted beneath the surface of the skin 14. The probe tip 422 may be inserted through an existing perforation in the skin 14 (such as made by an applicator or obturator) or through a perforation made by a distal-most blade portion 423 of the probe tip 422. The ultrasound transducer 410 is powered to operate the probe tip 422. The distal end of the ultrasonically inactive probe sheath 430 is inserted beneath the surface of the skin 14. As the probe tip is advanced, the distal end of the probe sheath 430 is retracted to expose a greater length of at least probe tip 422. In one variation, the retraction of the distal end of the probe sheath 430 is caused by a longitudinal resistance to the advancement of the distal end of the probe sheath 430. In another variation, the user retracts the distal end of the probe sheath using an adjustment mechanism 460. In another variation, the distal end of the probe sheath 430 initially covers substantially all proximal portions of the probe tip 422, with retraction of the distal end of the probe sheath exposing proximal portions of the probe tip only after an initial penetration of the skin.

In an implementation of the method, a dermal filler 12 is injected into the facial feature 10. The dermal filler 12 may be injected before or after insertion of the probe tip 422 within the skin, depending upon the source of the dermal filler, e.g., separate applicator or injection through a fluid lumen of the end effector 420 (such as interstitial space 429 or internal lumen 431). The probe tip is used to shear-thin the dermal filler 12. In one variation of the implementation, the ultrasound transducer 410 is depowered and the dermal filler 12 is manipulated from the surface of the skin 14 while in a shear-thinned state. In another variation of the method, the ultrasound transducer 410 is depowered, and the probe tip 422 and probe sheath 430 withdrawn from the skin, whereupon the dermal filler 12 is manipulated from the surface of the skin 14 while in a shear-thinned state.

In another implementation of the method, the device is used to perform blepharoplasty. The distal probe tip 422 is inserted beneath the surface of the skin above a periorbital fat pad. Upon reaching the interior of the periorbital fat pad, the distal probe tip 422, and potentially a distal portion of the probe neck 424, may be manipulated within the periorbital fat pad while the ultrasound transducer 410 is powered to fluidize and shift or lyse and remove periorbital fat. The distal probe tip 422 may also be used to shear-thin a dermal filler 12 that has been injected into the periorbital fat pad in order to further shape the pad, or to inject a dermal filler 12 to take the place of previously removed fat. In a variation of the method, presented in the context of the present implementation, the distal end of the ultrasonically inactive probe sheath 430 is separable from the ultrasonic surgical instrument, e.g., by separating a frangible portion of the probe sheath 430 providing a perforated or scored periphery, or uncoupling coupling between distal and proximal portions of the probe sheath. The distal end of the probe sheath 430 is separated from the instrument (although still coaxially positioned on the instrument), whereupon the instrument is withdrawn while the separated distal end of the probe sheath remains in place beneath the surface of the skin. The separated distal end of the probe sheath 430 can thus function as an obturator, and the ultrasonic surgical instrument can later be reinserted through this obturator. Also, other surgical instruments, exploratory instruments, cannulae, and the like can be inserted through this obturator as part of a greater surgical procedure. The separated distal end of the probe sheath is, of course, eventually withdrawn from beneath the skin to complete that stage of the overall surgical procedure.

The expressions of the third and fourth embodiments advantageously shear-thin dermal fillers to make injection procedures more precise while simultaneously enabling the use of highly molecular weight, high longevity biomaterials. The same ultrasound end effector may be used to inject dermal fillers and to facilitate the bloodless dissection of tissue, as well as to create pockets for dermal filler and/or to remove unwanted tissue, such as fat. The end effectors 320 and 420 also may be used in vivo to thin previously injected filler so that it can be finger massaged to the desired location and thickness, as well as to remove excess filler if it has been inadvertently injected. If irrigation of a tissue pocket is desired, the same fluid lumen may be used for suction irrigation as for dermal filler injection and adjustment.

In a fifth embodiment of the invention, shown in FIGS. 33-76, the active portions of medical ultrasound handpiece assemblies 300 or 400 (and similar devices) and contact end effectors 320 or 420 (and similar devices) may be constructed from a single crystal or polycrystalline resonating material, principally silicon, although germanium, diamond, and sapphire may also be used. Preferably, these structures are manufactured from a semiconductor wafer so as to be manufacturable using existing semiconductor processes. In addition, the transducer material may be a lead-free piezoelectric material, such as barium titanate, or a magnetostrictive material, such as nickel or "GALFENOL" (gallium-iron alloys marketed by ETREMA Products, Inc. of Ames, Iowa), so that the device may be both inexpensive enough to be employed as a single use device and suitable for disposal as ordinary medical waste, as opposed to lead-bearing hazardous waste. Other transducing materials, including ceramic PZT materials and electrostrictive materials, as well as single crystal materials, can also be used. PZT materials are typically lead-bearing, but have generally better piezoelectric performance. Electrostrictive materials are also frequently lead-bearing, but exhibit less hysteresis than piezoelectrics, have higher strain energy densities than piezoelectrics, and do not need to be poled; however electrostrictive materials also have greater temperature sensitivity, require greater differential voltages, and require different modes of electrical control (since strain varies quadratically rather than linearly with respect to the applied voltage). Electrostrictive transducer structures and transducers may be manufactured from materials such as PMN (lead magnesium niobate), PSN (lead strontium niobate), or PMN-PT (lead magnesium niobate with lead titanate dopant), and may be driven in either a $d_{31}$ or $d_{33}$ mode. Magnetostrictive materials do not require poling, are ductile, can be used with low voltage drive circuits, and permit the use of designs which minimize potential electrical leakage by electrically isolating the waveguide and end effector from the surrounding electromagnetic coil, electrical contacts, and handpiece housing; however magnetostrictive materials are subject to eddy current effects and magnetostrictive power transfer is comparatively less power efficient, so as to require some form of active cooling of magnetostrictive actuators and surrounding electromagnetic coils.

Figure 33:
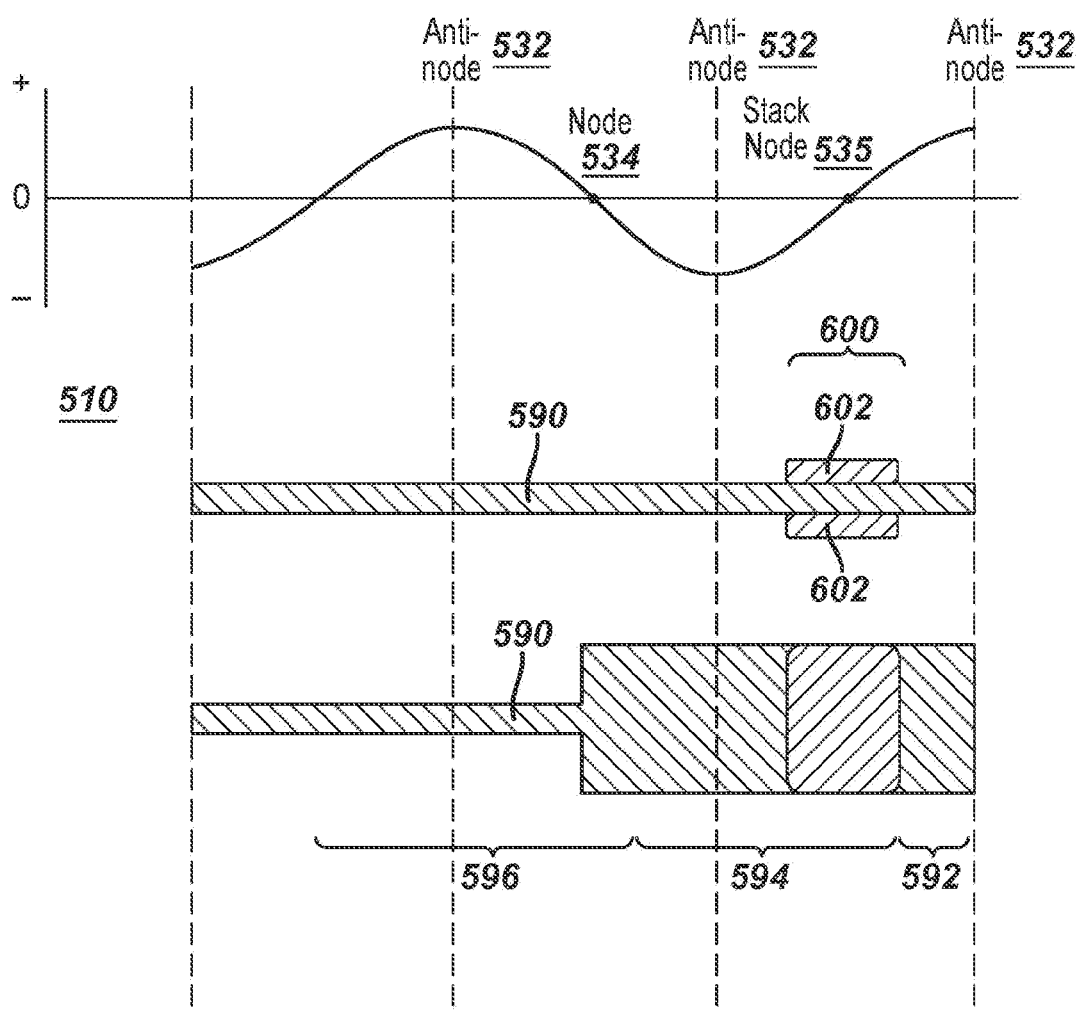
FIG. 33 is schematic view with side and edge views of an ultrasonic core.
Figure 34:
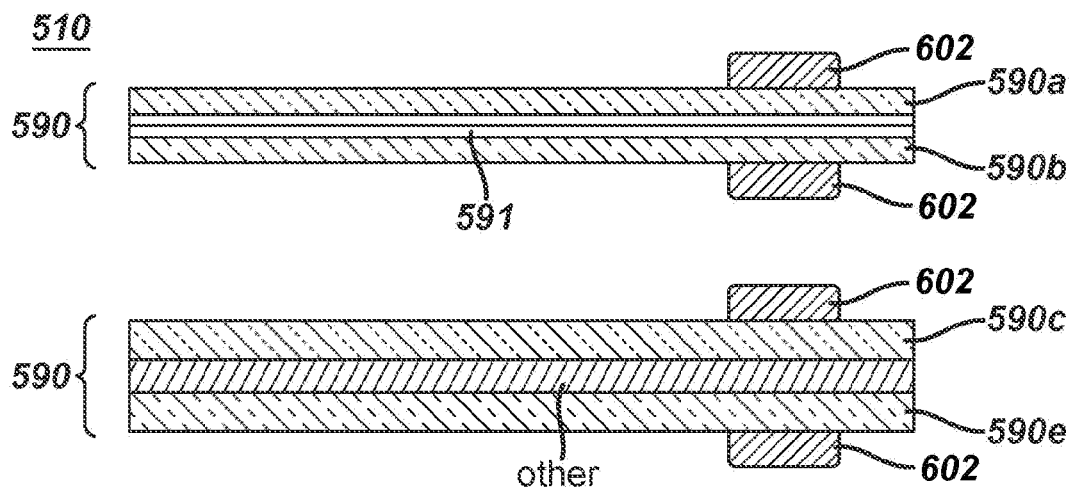
FIG. 34 is a cross-sectional edge view of exemplary laminated ultrasonic core constructions.
Figure 35:
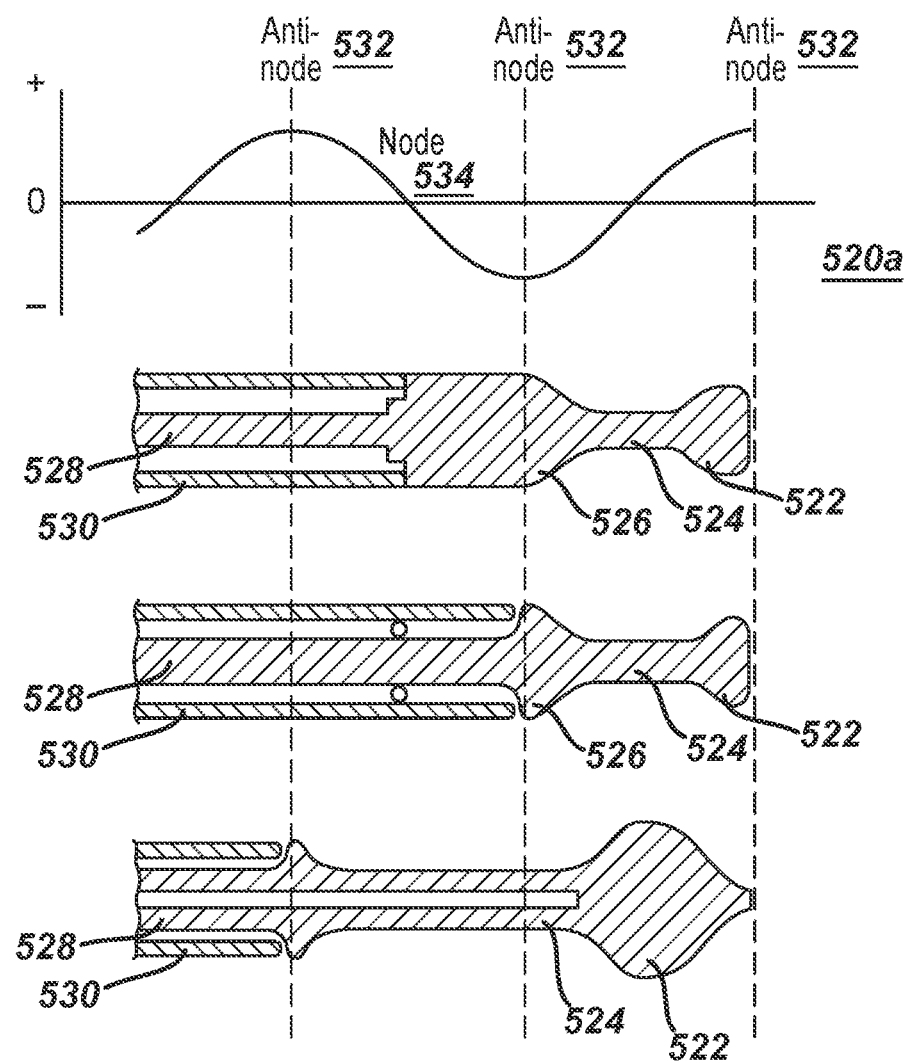
FIG. 35 is a cross-sectional side view of exemplary end effector portions.
Figure 36:
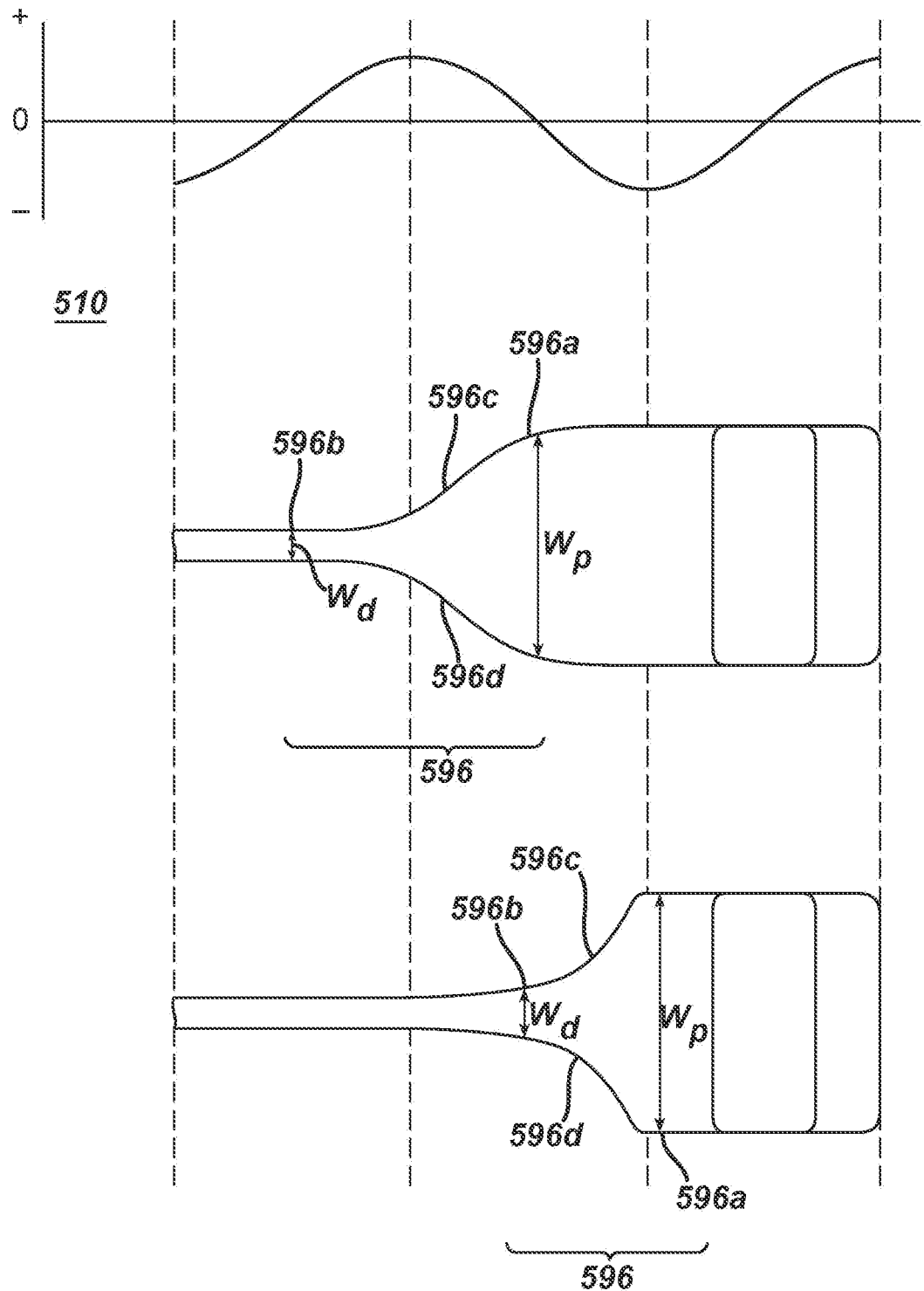
FIGS. 36 and 37 are schematic side views of exemplary second resonator configurations.

The fifth embodiment, illustrated schematically in FIGS. 33 and 34, includes an ultrasonic core 510 for an ultrasonic surgical apparatus including a longitudinally elongated, generally planar waveguide 590 constructed from a single crystal or polycrystalline material, and a transducer structure 600 including one or more transducers 602 affixed to the waveguide 590. The waveguide material is preferably silicon. For sake of clarity in the following discussion, the term "end" will be understood as referring to a longitudinal boundary, or a surface representing such a boundary; the term "edge" will be understood as referring to a lateral boundary, or surface representing such boundary, in a direction within the plane of the waveguide 590; and the term "side" will be understood as referring to a lateral boundary, or surface representing such a boundary, in a direction perpendicular to the plane of the waveguide 590.

The waveguide 590 includes, in order, a first resonator or proximal end portion 592, a transduction portion 594, and a second resonator or distal end portion 596, as well as optional ancillary structures such as mounts or mount connections, intermediate gain stage structures, and the like which may be formed between components 592, 594, and 596. In one construction, the waveguide 590 is a monolithic structure. In another construction, shown in FIG. 34, the waveguide 590 is a laminated structure including a plurality of planar layers 590a, 590b, etc. of the material. In one variation of the latter construction, two adjoining layers, e.g., 590a and 590b, may define a longitudinal channel, or other internal voids, which may serve, for example, as an internal lumen 591. In another variation of the latter construction, adjacent layers 590c and 590e may be separated by other materials, as further described below, in the laminated structure. The fifth embodiment may also include a single or polycrystalline material end effector portion 520a, such as those shown in FIG. 35, configured to serve at least as an ultrasonically active shaft 528. The end effector portion 520a preferably is configured to serve as a complete surgical probe (excepting ultrasonically inactive components such as the probe sheath 530); for example, one having an ultrasonically active shaft 528 and a distal probe tip 522. In one construction, the end effector portion 520*a* and the waveguide 590 (or a plurality of the layers thereof) are a monolithic structure, and thus monolithically coupled. Such a construction is suitable for precision microsurgical procedures such as dermatological procedures, dermal filler procedures like those described above, or neurological or hand surgeries. In another construction, the end effector portion 520*a* and the waveguide 590 are resonantly adjoining, i.e., resonantly connected at a node 534 for the transmission of a mode of vibration, and thus resonantly coupled.

Figure 37:
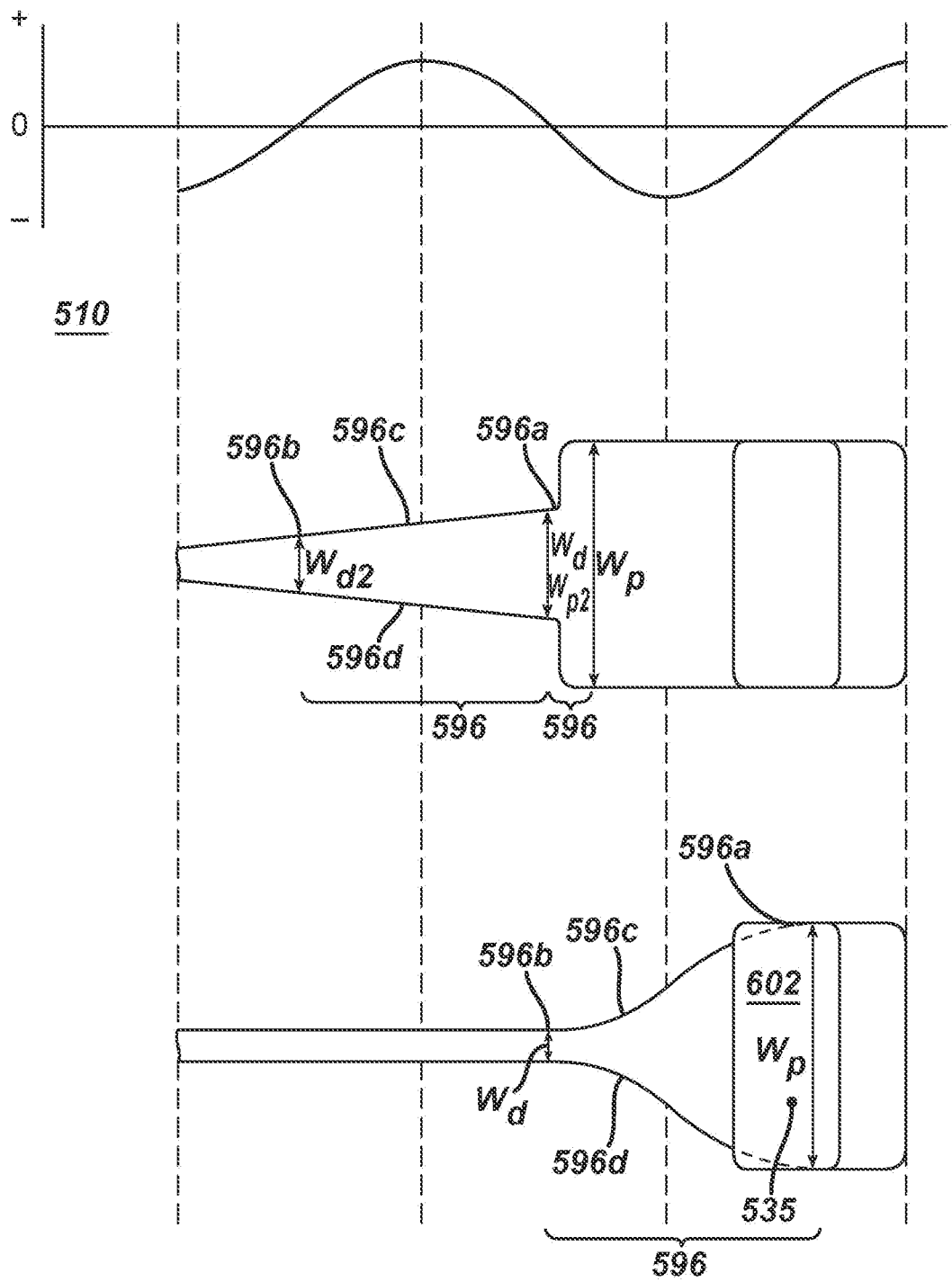

In a first expression of the fifth embodiment, shown in FIGS. 36-41, the second resonator 596 of waveguide 590 is configured to vary the magnitudes and/or modes of ultrasonic vibration created in the transduction portion 594 prior to transmission into an end effector portion 520*a*. The second resonator 596 includes a proximal end 596*a* having first transverse extent, e.g., a width $w_p$, a distal end 596*b* having a second, lesser transverse extent, e.g., a width $w_d$, and a body generally narrowing between the first and second transverse extents so as to create vibrational gain. In various constructions, the edges 596*c* and 596*d* of the second resonator 596 may be sinusoidally curved (FIG. 37 bottom), convexly or concavely curved (FIG. 36, top and bottom), constantly tapered (FIG. 37 top left), discontinuously stepped (FIG. 37 top right), or a shaped with a combination of any of the foregoing to vary the mode of ultrasonic vibration and, typically, to separate desirable modes of vibration from undesirable modes of vibration. As shown in FIG. 37, bottom instance, portions of a transducer 602 may extend over the proximal end 596*a* of the second resonator 596, which in a monolithic structure such as the present waveguide 590 is generally distinguished by a rapid change in geometry near a node 534, or (as in FIG. 37 bottom) an intermediate or stack node 535.

Figure 38:
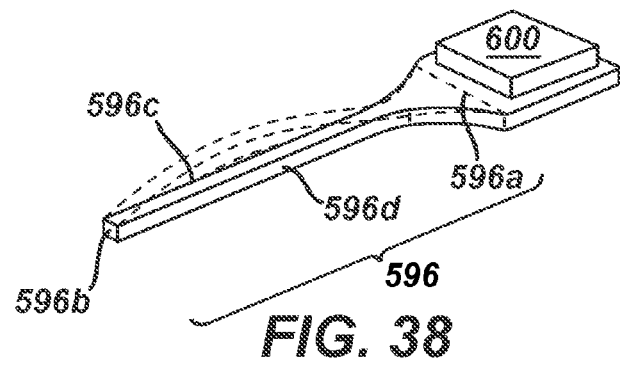
FIG. 38 is a perspective view of an exemplary second resonator configuration, with a resonant transverse mode of vibration shown in an exaggerated physical representation in phantom lines (top side only).
Figure 39:
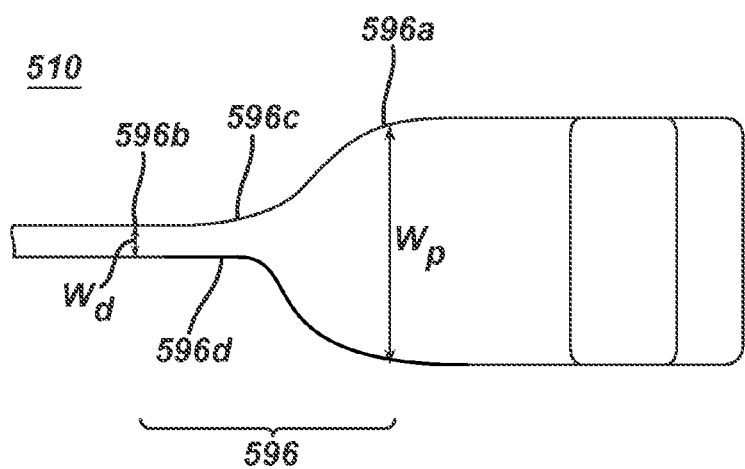
FIGS. 39 and 40 are schematic side views of exemplary second resonator configurations.
Figure 40:
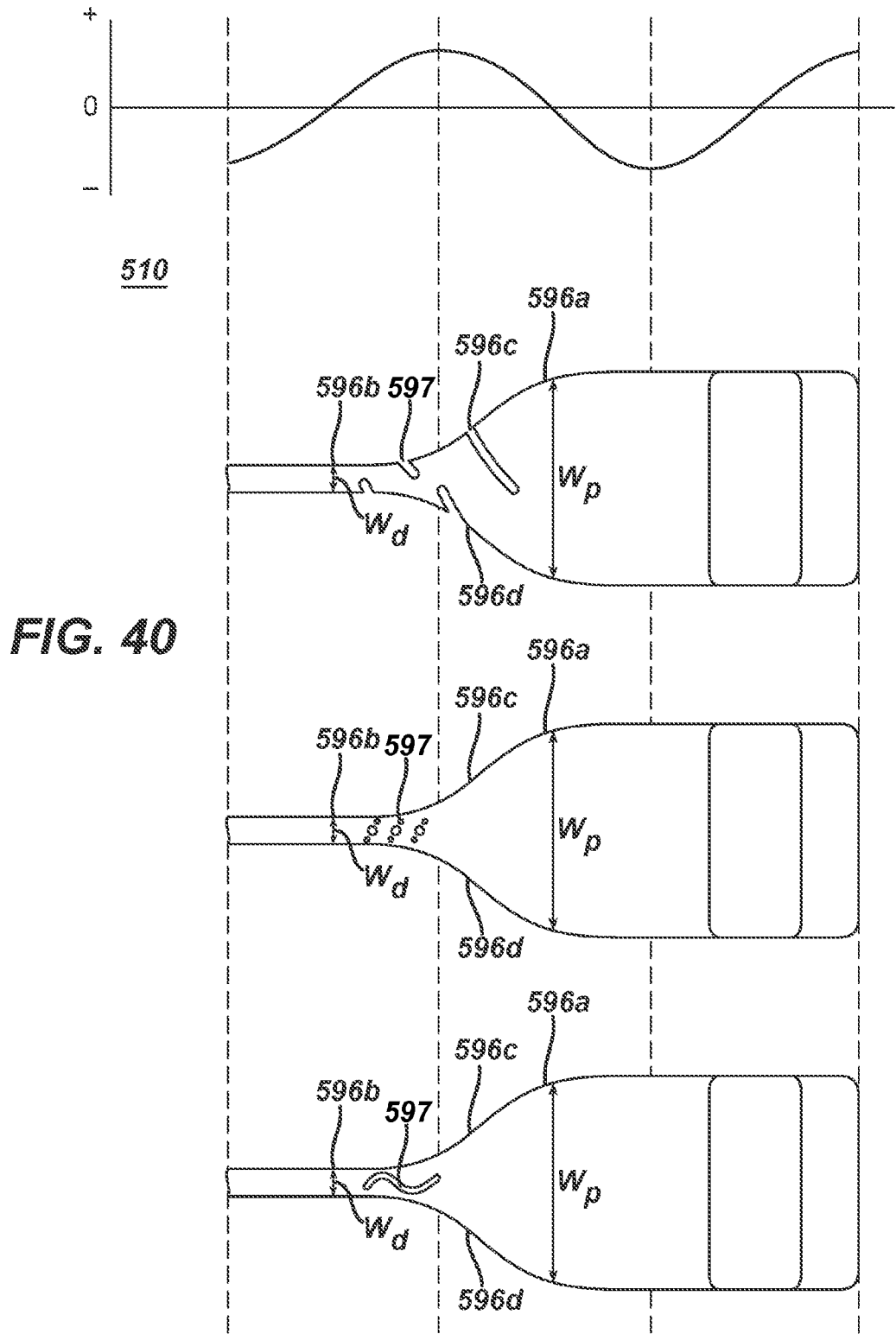

In a first construction of the first expression, shown in FIG. 38, the second resonator 596 is symmetric with respect to the central longitudinal axis of the waveguide 590 and has a substantial body portion with an essentially invariant transverse extent matching the second transverse extent of the distal end 596*b*. This symmetric and highly uniform construction can create a transverse mode of vibration at a subharmonic frequency, $\omega_n/N$ (where N=1, 2, 3, etc.), when transduction portion 594 is longitudinally vibrated at a primary frequency, $\omega_n$, due to autoparametric resonance. An end effector portion 520*a* coupled to the second resonator 596 may be configured to operate in a transverse working mode at a frequency equal to the subharmonic frequency, so that the mode of ultrasonic vibration is effectively transformed from a longitudinal driving mode at frequency $\omega_n$ to a transverse working mode at frequency w, IN.

In a second construction of the first expression, the second resonator 596 is asymmetric with respect to the central longitudinal axis of the waveguide 590. In an exemplary construction, shown in FIG. 39, the edges of the second resonator are asymmetric with respect to the central longitudinal axis of the wave guide 590, with one edge 596*c* of the second resonator 596 being sinusoidally curved and the opposite edge 596*d* of the second resonator 596 being concavely curved. In other exemplary constructions, edges 596*c* and 596*d* may be shaped with one or more of the foregoing shapes, but are not identically shaped. These asymmetric constructions cause symmetric shear mode vibrations which create an additional transverse mode of vibration in proximal end 596*a* when transduction portion 594 is longitudinally vibrated. In another exemplary construction, shown FIG. 40, the body of the second resonator is rendered asymmetric with respect to the central longitudinal axis of the wave guide 590 by at least one aperture 597. The aperture 597 may be a slot extending partially longitudinally and partially laterally inwards from an edge 596*c* or 596*d* of the second resonator 596. In one modification (FIG. 40 middle) apertures 597 may be a staggered array of holes. In another modification (FIG. 40 bottom) the aperture 597 may be a longitudinally extending, sinusoidal slot. These asymmetric constructions cause the longitudinal resonant mode to couple into an additional torsional mode of vibration when transduction portion 594 is longitudinally vibrated.

Figure 41:
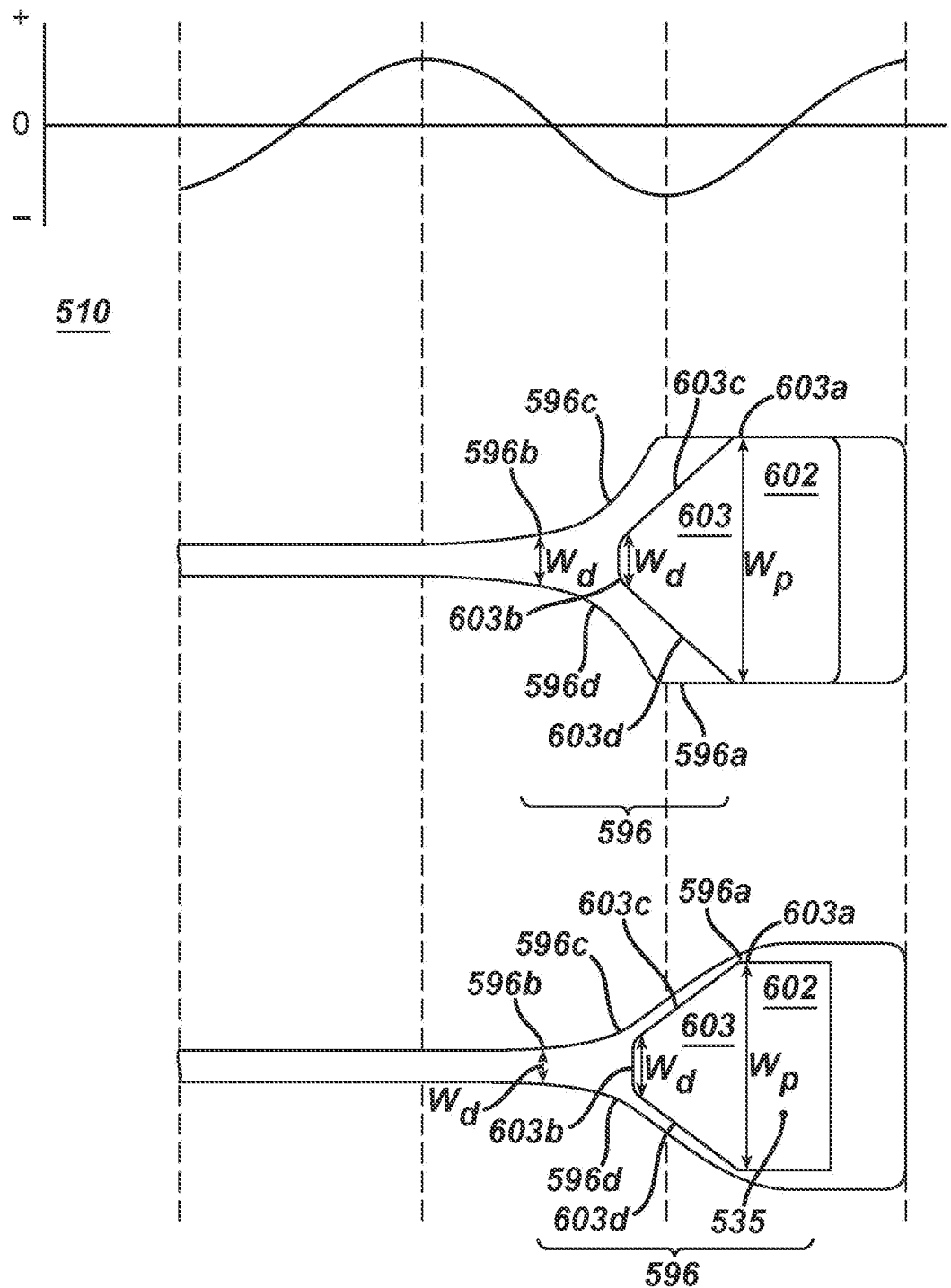
FIG. 41 is a schematic side view of exemplary second resonator configurations including a transducer gain portion.
Figure 42:
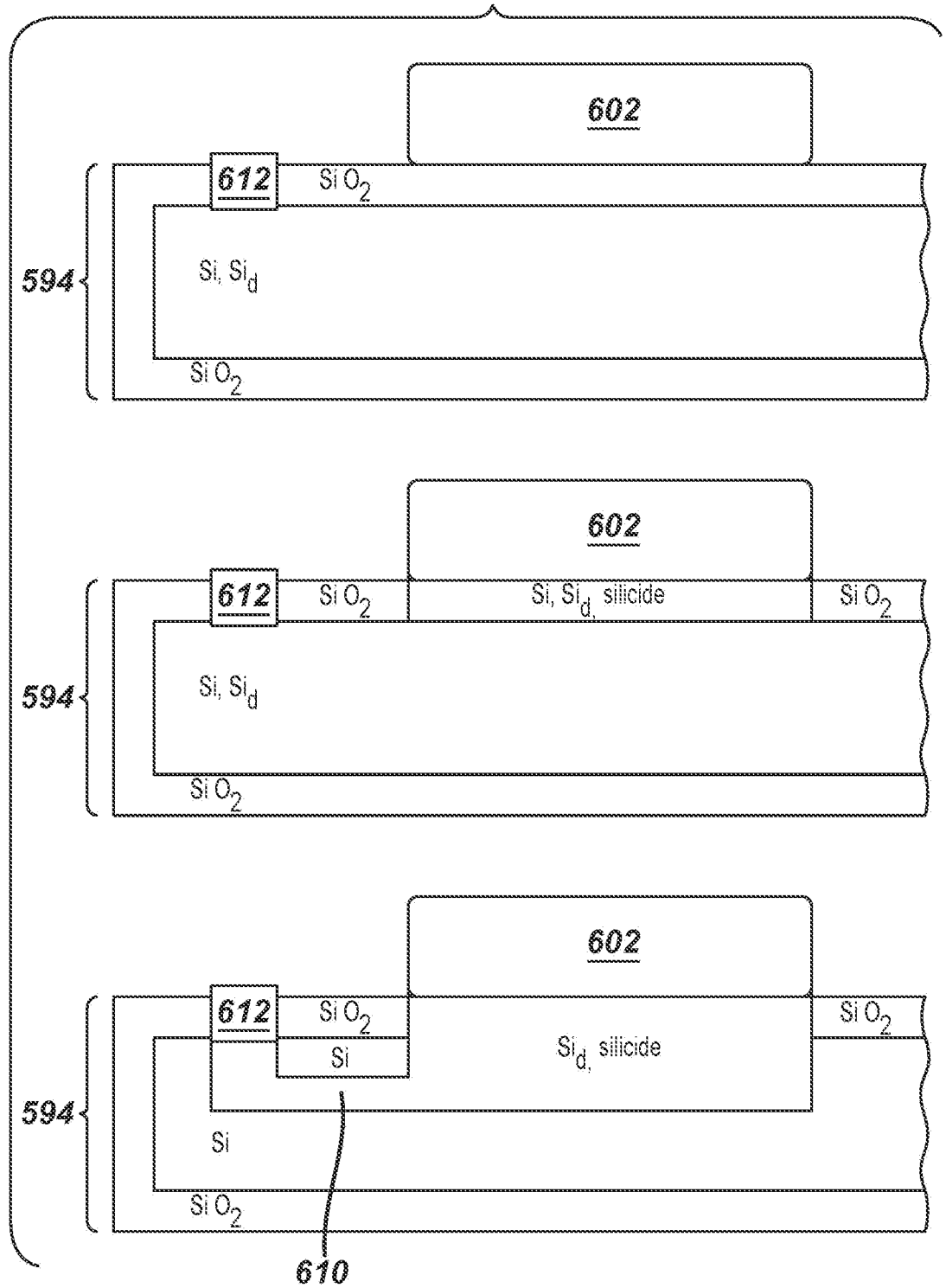
FIG. 42 is a schematic end view of exemplary transducer-to-waveguide bond and power structures.

In a third construction of the first expression, shown in FIG. 41, the second resonator 596 may include a gain portion 603 of a transducer 602 generally affixed to the adjoining transduction portion 594 of waveguide 590. The gain portion 603 may include a proximal end 603*a* having first transverse extent, e.g., a width $w_p$, a distal end 603*b* having a second, lesser transverse extent, e.g., a width $w_d$, and a body generally narrowing between the first and second transverse extents so as to create vibrational gain. In various constructions, the edges 603*c* and 603*d* of the gain portion 603 may be sinusoidally curved, convexly or concavely curved, constantly tapered, discontinuously stepped, or a shaped with a combination of any of the foregoing to vary the mode of ultrasonic vibration at the a distal end 596*b* of second resonator 596. The gain portion 603 may structured, affixed to the second resonator 596, and powered in essentially the same manners discussed below in the context of the transducer 602 and the transduction portion 594. The exposed side of the gain portion 603 may also be tapered from the proximal end 603*a* to the distal end 603*b*, i.e., the gain portion 603 may gradually reduce in thickness, as an additional means of increasing gain.

Figure 43:
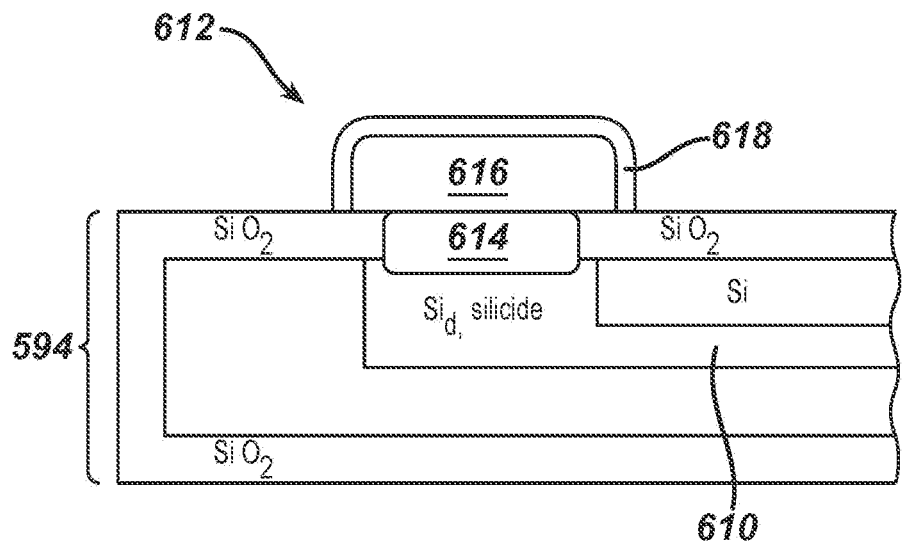
FIG. 43 is a schematic detail view of a waveguide electrical contact (Note: structure of transduction portion 594 is exemplary only).

In a second expression of the fifth embodiment, shown in FIGS. 42-59B, at least one transducer 602 is affixed to a side of the transduction portion 594 of waveguide 590. In a first construction of the second expression, shown in FIG. 42, the transducer 602 is a piezoelectric or electrostrictive ceramic directly bonded to a side of the transduction portion 594. In a first variation of the first construction, the bonded surface of the transduction portion 594 may consist essentially of an oxygen rich surface layer, e.g., silicon dioxide ($SiO_2$), to insulate the transducer 602 from the transduction portion 594. In a second variation of the first construction, the bonded surface of the transduction portion 594 may consist essentially of elemental silicon (Si), elemental silicon containing a dopant ($Si_d$), or a silicide. The substrate of the transduction portion 594 in the second variation may consist essentially of elemental silicon or elemental silicon containing a dopant (i.e., bulk-doped silicon). Where the subsurface of the transduction portion 594 consists essentially of undoped elemental silicon, an embedded path 610 of silicon containing a dopant, or silicide, may be included to provide a preferential electrical path. Other surfaces of the waveguide 590 may be insulated by an oxygen rich surface layer formed on the waveguide 590 to prevent unintentional grounding. At least one electrical contact 612 may be provided on the waveguide, e.g., on an exposed surface of the transduction portion 594, proximate a node 534. An exemplary electrical contact 612, shown in cross section in FIG. 43, is a solder pad penetrating the oxygen rich surface layer (if present), in electrical contact with the subsurface of the transduction portion, and in electrical contact with the embedded path 610 (if present). In one exemplary construction, the electrical contact 612 includes an aluminum-copper alloy bonding layer 614, a nickel pad 616, and a gold top coat 618. A ground wire may be soldered to the electrical contact 612 to complete the ground path for the transducer 602.

Figure 44:
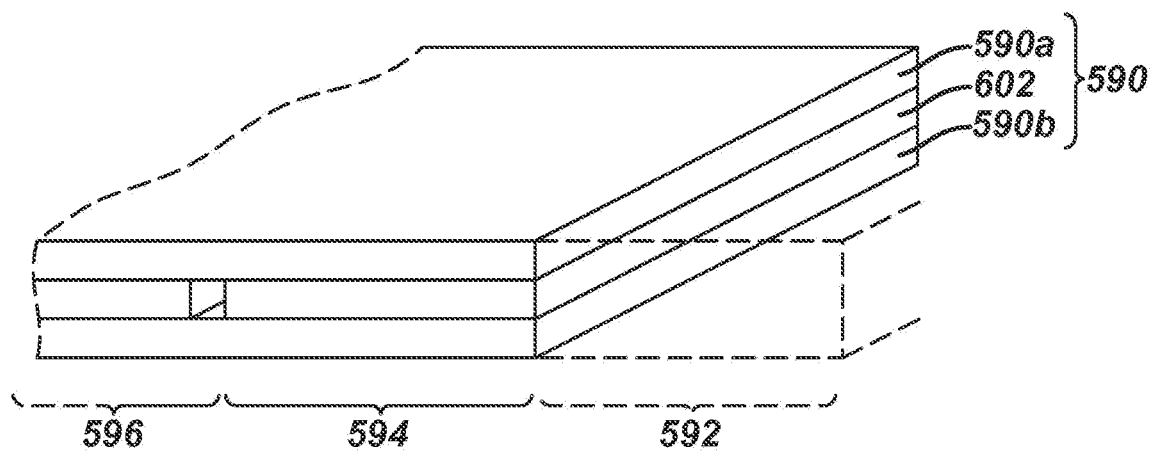
FIG. 44 is a schematic perspective view of a laminated waveguide with internal transducer. First resonator 592 is omitted but partially outlined in phantom lines for context.
Figure 45:
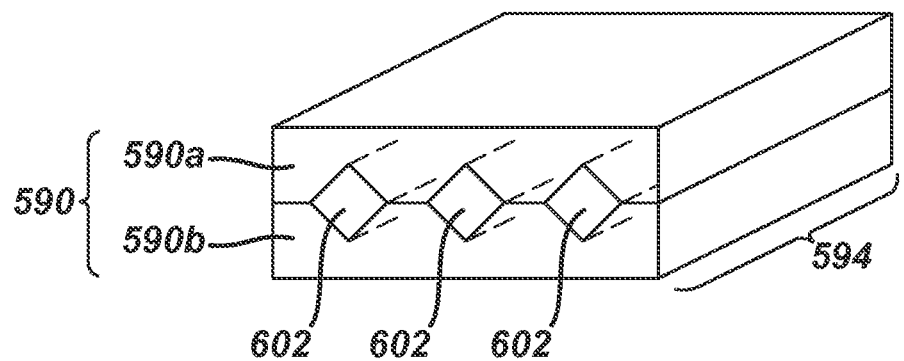
FIG. 45 is a schematic perspective view of a transduction portion, with first and second resonators omitted.

In a third variation of the first construction, shown in FIGS. 44 and 45, the transducer 602 is a piezoelectric or electrostrictive ceramic directly bonded on opposite sides to the transduction portions 594 of adjacent or adjoining layers 590a and 590b of a laminated waveguide 590. In a further variation, one layer may serve as an electrical source for the interstitially-disposed transducer 602 (when wired to an electrical source), and the other adjacent or adjoining layer may serve as an electrical ground (when wired to ground). In such a variation, the structure of the transduction portions 594 of both layers 590a and 590b may be the same as that described above, with an oxygen rich surface layer insulating adjoining portions, if any, of the transduction portions 594 of the layers. Alternately, the laminant between adjoining layers 590a and 590b may be an insulator. An exemplary laminant (not intended to be interpreted as "other materials" or to cause layers 590a and 590b to be considered adjacent rather than adjoining) is a silicon-to-silicon anodic bonding glass layer.

Figure 46:
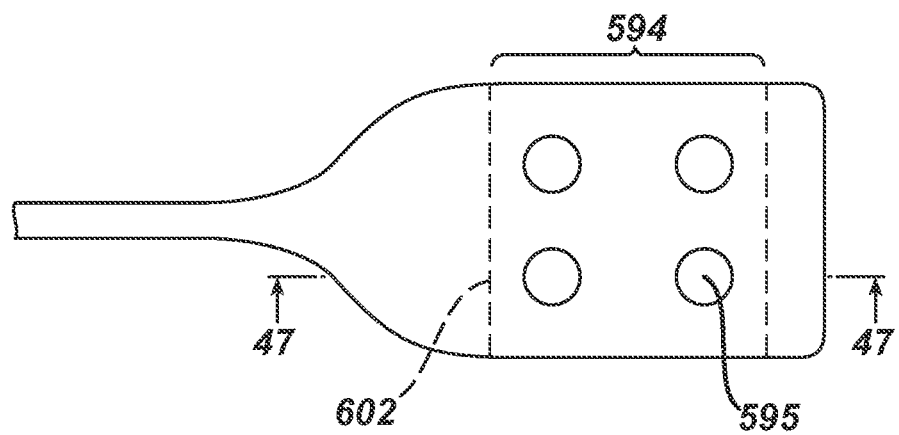
FIG. 46 is a side view of a transduction portion of a waveguide with the position of a transducer shown in phantom lines for context.
Figure 47:
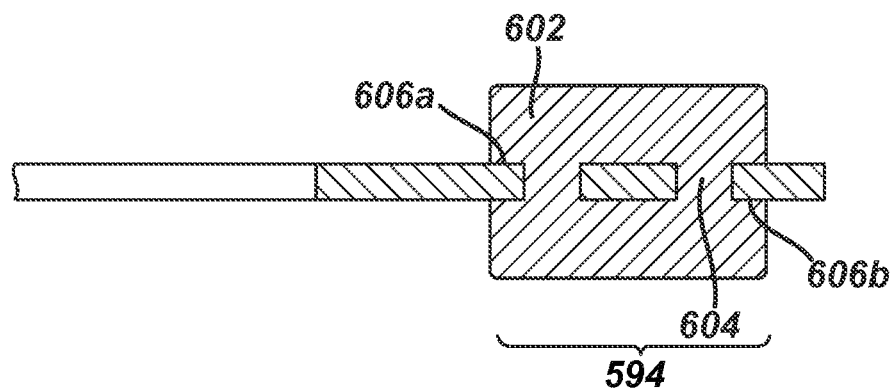
FIG. 47 is a cross-sectional edge view of the waveguide of FIG. 46.
Figure 48:
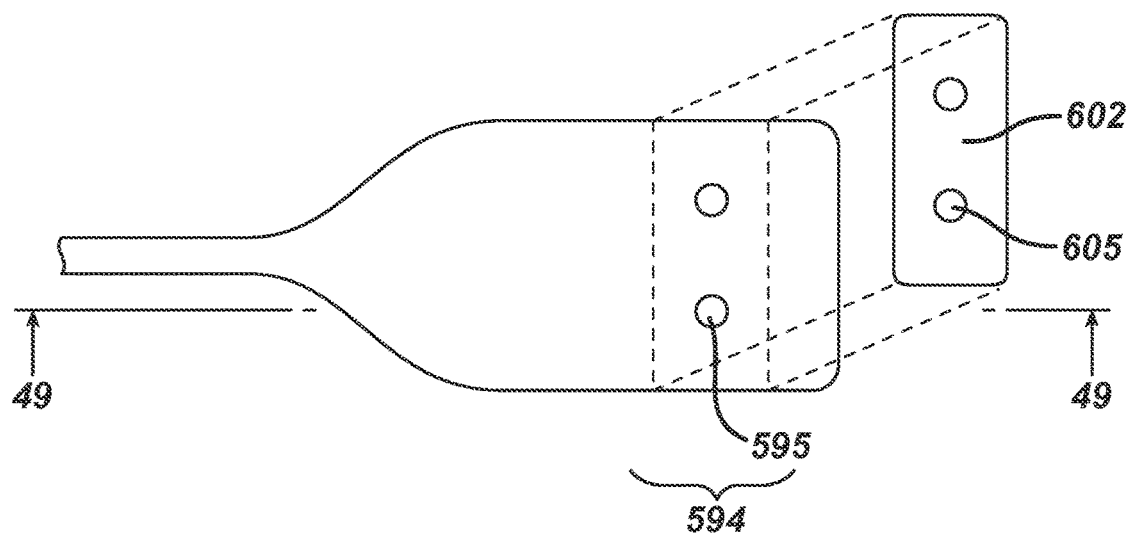
FIG. 48 is an exploded side view of a transduction portion of a waveguide.
Figure 49:
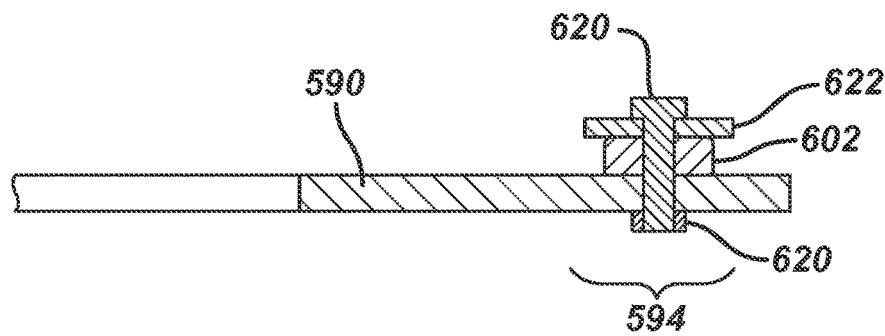
FIG. 49 is a cross-sectional edge view of the waveguide of FIG. 48, including a plate and compressive fastener.

In a fourth variation of the first construction, shown in FIGS. 46 and 47, the transducer 602 is a piezoelectric or electrostrictive ceramic directly bonded to both sides of the transduction portion 594. The transduction portion 594 includes at least one aperture 595 which is filled by a bridging portion 604 of a monolithic transducer 602. Abutment portions 606a and 606b of the transducer 602 abut the respective sides of the transduction portion 594 adjacent the at least one aperture 595. In addition to direct bonding of the transducer 602 with the transduction portion 594, mechanical abutment between the portions 604, 606a, 606b of the transducer 602 and the transduction portion 594 further affixes the transducer to the sides of the transduction portion 594. The transducer 602 may be formed in place by slip-forming and sintering the transducer material on the transduction portion 594.

Figure 50:
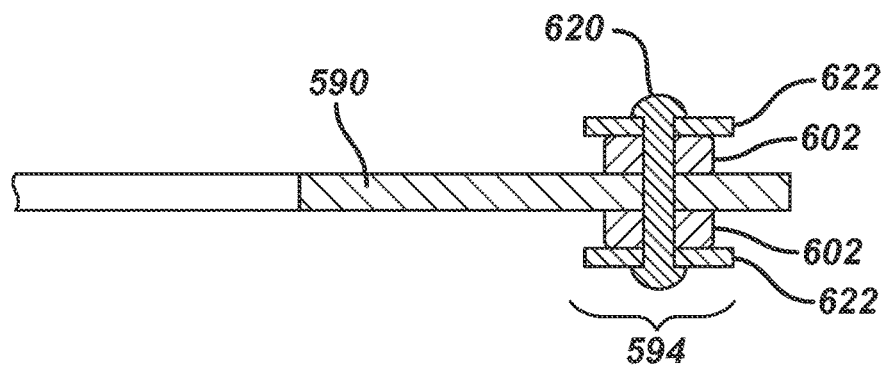
FIG. 50 is a cross-sectional edge view of a device similar to that shown in FIG. 48, but with symmetrically disposed transducers, plates, and a compressive fastener.
Figure 51A:
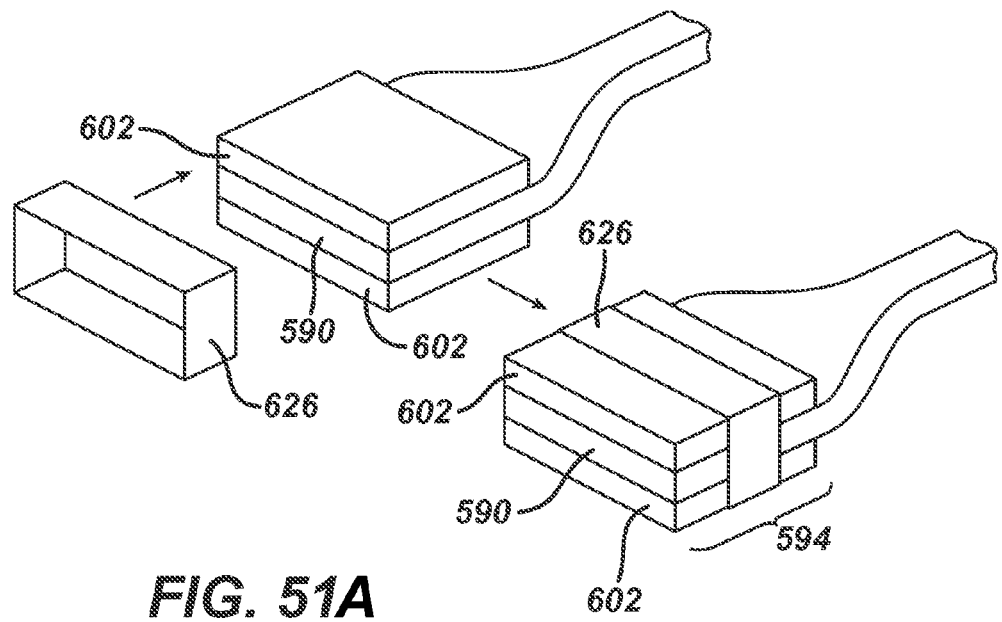
FIGS. 51A and 51B are perspective views of a transduction portion of a waveguide before and after the application of metal band.
Figure 51B:
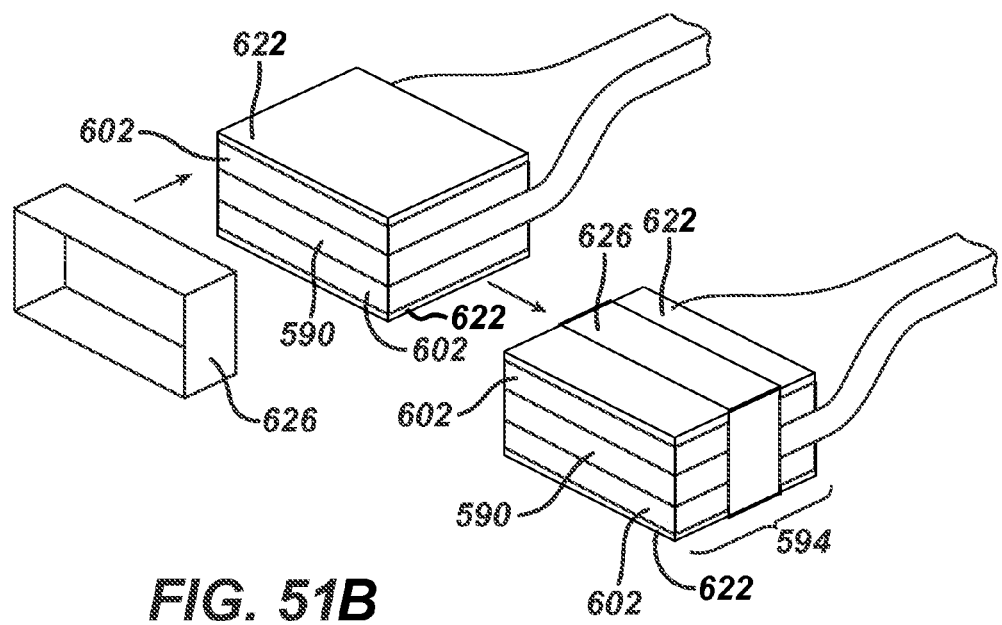
Figure 52A:
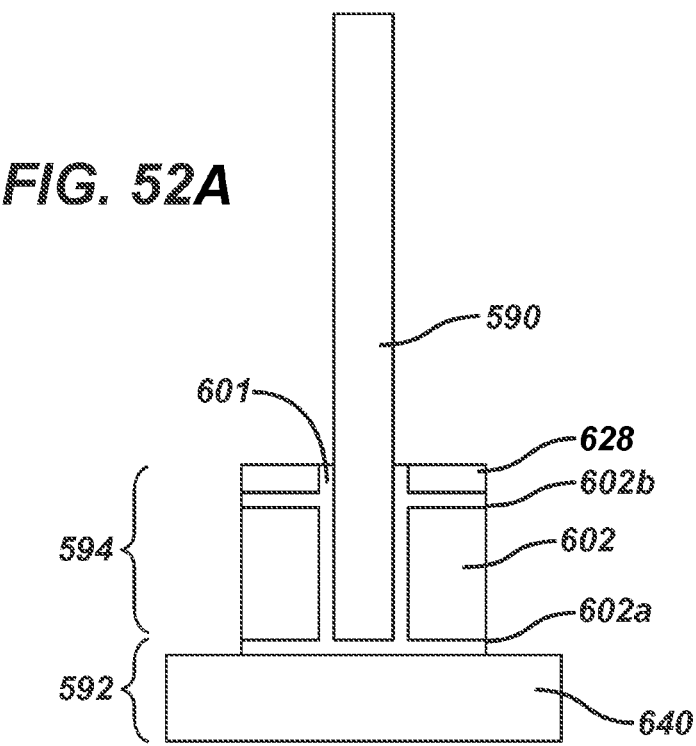
FIG. 52A is an edge view of a waveguide, with braze 601 exaggerated for visual clarity.

In a second construction of the second expression, the transducer 602 is clamped to a side of the transduction portion 594. This clamped construction is a simple mechanism for attachment, but also may be used to preload ceramic and single crystal transducers to increase power and displacement during shear mode operation of the transducer 602. In a first variation of the second construction, shown in FIGS. 48 and 49, the transduction portion 594 includes at least one aperture 595 and the transducer 602 includes at least one corresponding aperture 605. The aperture(s) 595 are preferably positioned at an anti-node 532. The corresponding apertures 595 and 605 are axially aligned and receive a compressive fastener 620, such as a bolt or rivet. In one modification, a plate 622 is disposed between an otherwise exposed side of the transducer 602 and the fastener 620 to distribute clamping forces over the transducer 602. In another modification (not specifically shown), a plate 624 is disposed between an otherwise exposed side of the transduction portion 594 and the fastener 620 to relieve local stress on the transduction portion 594 adjacent the aperture 595. As illustrated in FIG. 50, multiple transducers 602 and, if appropriate, multiple plates 622 may be clamped to the transduction portion 594 by the same compressive fastener 620. In a second variation of the second construction, shown in FIGS. 51A and 51B, a metal band 626 may be secured around the transduction portion 594 and transducer 602. The metal band is preferably heated, positioned, and allowed to cool to generate the clamping force. In one modification, a plate 622 is disposed between an otherwise exposed side of the transducer 602 and the metal band 626 to distribute clamping forces over the transducer 602. In another modification (not specifically shown), a plate 624 is disposed between an otherwise exposed side or edge of the transduction portion 594 and the metal band 626 to relieve local stress on the transduction portion 594 under the metal band 626. As illustrated in FIGS. 51A and 51B, multiple transducers 602 and, if appropriate, multiple plates 622 may be clamped to the transduction portion 594 by the same metal band 626.

In a third construction of the second expression, the transducer 602 is indirectly bonded to the transduction portion 594 by an adhesive or braze 601. Exemplary adhesives are epoxies, urethane acrylates, and cyanoacrylates, while exemplary brazes are set out in Table 1. In a first variation of the third construction, a proximal end 602a and a distal end 602b of the ultrasound transducer 602 are longitudinally compressed during bonding with the adhesive or braze 601. Once the adhesive has cured or the braze has cooled, the ultrasound transducer 602 remains residually compressed by the established bond between the transducer 602, the adhesive or braze 601, and the transduction portion 594. In a further variation, shown in FIG. 52A, a distal end plate 628 may be similarly bonded to the waveguide 590, in an abutting relationship with the distal end 602b, to resist decompression of the transducer 602 and, during construction, to distribute compressive forces over distal end 602b of the transducer 602. The distal end plate 628 may conveniently be similarly bonded to the distal end 602b to form an integrally bonded assembly. In a yet further variation, also shown in FIG. 52A, an end mass 640 may be similarly bonded to the first resonator or proximal end portion 592 of the waveguide 590, in an abutting relationship with the proximal end 602a, to resist decompression of the transducer 602 and, during construction, to distribute compressive forces over the proximal end 602a of the transducer 602. Where necessary or desirable, an adhesion layer may be applied to the bonding surfaces. The adhesion layer for an electrically conductive surface to be brazed with one of the compositions described herein may be prepared, for example, with a nickel plate and a gold top coat.

TABLE 1

Brazing Compositions and Temperatures

| Alloy composition | Melting range solidus | | Melting range liquidus | | Mushy range (Δ) | |
|---|---|---|---|---|---|---|
| | °C. | °F. | °C. | °F. | °C. | °F. |
| 70Sn/30Pb | 183 | 361 | 193 | 380 | 10 | 19 |
| 63Sn/37Pb | 183 | 361 | 183 | 361 | 0 | 0 |
| 60Sn/40Pb | 183 | 361 | 190 | 375 | 7 | 14 |
| 50Sn/50Pb | 183 | 361 | 216 | 420 | 33 | 59 |
| 40Sn/60Pb | 183 | 361 | 238 | 460 | 55 | 99 |
| 30Sn/70Pb | 185 | 365 | 255 | 491 | 70 | 126 |
| 25Sn/75Pb | 183 | 361 | 266 | 511 | 83 | 150 |
| 10Sn/90Pb | 268 | 514 | 302 | 575 | 34 | 61 |
| 5Sn/95Pb | 308 | 586 | 312 | 594 | 4 | 8 |
| 62Sn/36Pb/2Ag | 179 | 355 | 179 | 355 | 0 | 0 |
| 10Sn/88Pb/2Ag | 268 | 514 | 290 | 554 | 22 | 40 |
| 5Sn/95Pb | 308 | 586 | 312 | 594 | 4 | 8 |
| 62.5Sn/36Pb/2.5Ag | 179 | 355 | 179 | 355 | 0 | 0 |
| 10Sn/88Pb/2Ag | 268 | 514 | 290 | 554 | 22 | 40 |
| 5Sn/90Pb/5Ag | 292 | 558 | 292 | 558 | 0 | 0 |
| 5Sn/92.5Pb/2.5Ag | 287 | 549 | 296 | 564 | 9 | 15 |
| 5Sn/93.5Pb/1.5Ag | 296 | 564 | 301 | 574 | 5 | 10 |
| 2Sn/95.5Pb/2.5Ag | 299 | 570 | 304 | 579 | 5 | 9 |
| 1Sn/97.5Pb/1.5Ag | 309 | 588 | 309 | 588 | 0 | 0 |
| 96.5Sn/3.5Ag | 221 | 430 | 221 | 430 | 0 | 0 |

TABLE 1-continued

Brazing Compositions and Temperatures

| Alloy composition | Melting range solidus °C. | Melting range solidus °F. | Melting range liquidus °C. | Melting range liquidus °F. | Mushy range (Δ) °C. | Mushy range (Δ) °F. |
|---|---|---|---|---|---|---|
| 95Sn/5Sb | 235 | 455 | 240 | 464 | 5 | 9 |
| 42Sn/58Bi | 138 | 281 | 138 | 281 | 0 | 0 |
| 43Sn/43Pb/14Bi | 144 | 291 | 163 | 325 | 19 | 34 |
| 52Sn/48In | 118 | 244 | 131 | 268 | 13 | 24 |
| 70In/30Pb | 160 | 320 | 174 | 345 | 14 | 25 |
| 60In/40Pb | 174 | 345 | 185 | 365 | 11 | 20 |
| 70Sn/18Pb/12In | 162 | 324 | 162 | 324 | 0 | 0 |
| 90Pb/5In/5Ag | 290 | 554 | 310 | 590 | 20 | 36 |
| 92.5Pb/5lIn/2.5Ag | 300 | 572 | 310 | 590 | 10 | 18 |
| 97.5Pb/2.5Ag | 303 | 578 | 303 | 578 | 0 | 0 |

Source: Charles A. Harper, Electronic Packaging and Interconnection Handbook (4th Ed.), McGraw-Hill, 2004.

Figure 52B:
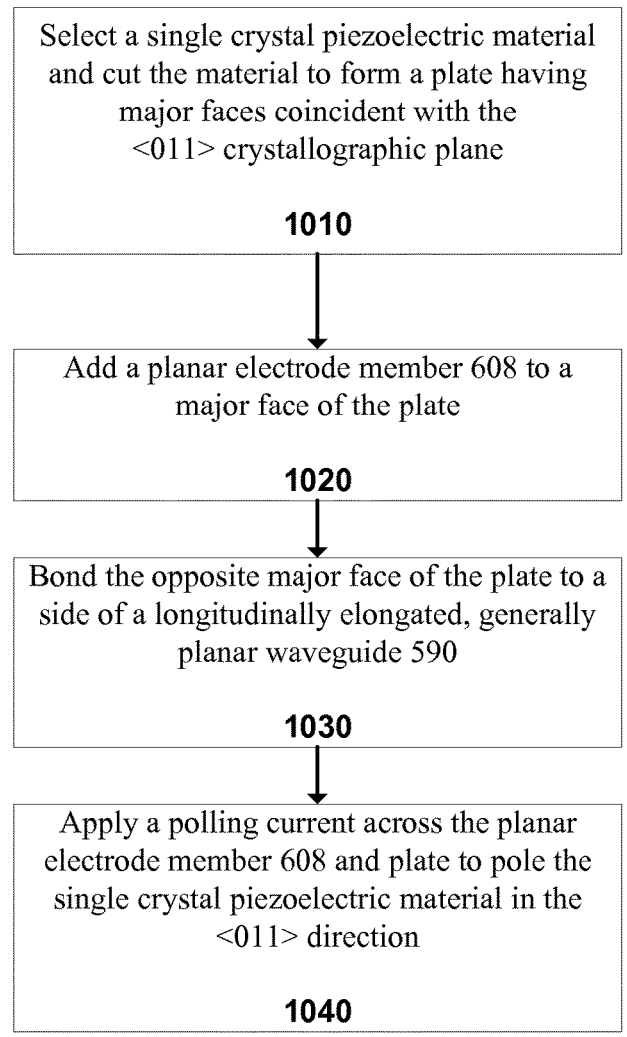
FIG. 52B is a diagram of a process for assembling an ultrasonic core with post-assembly poling.
Figure 52C:
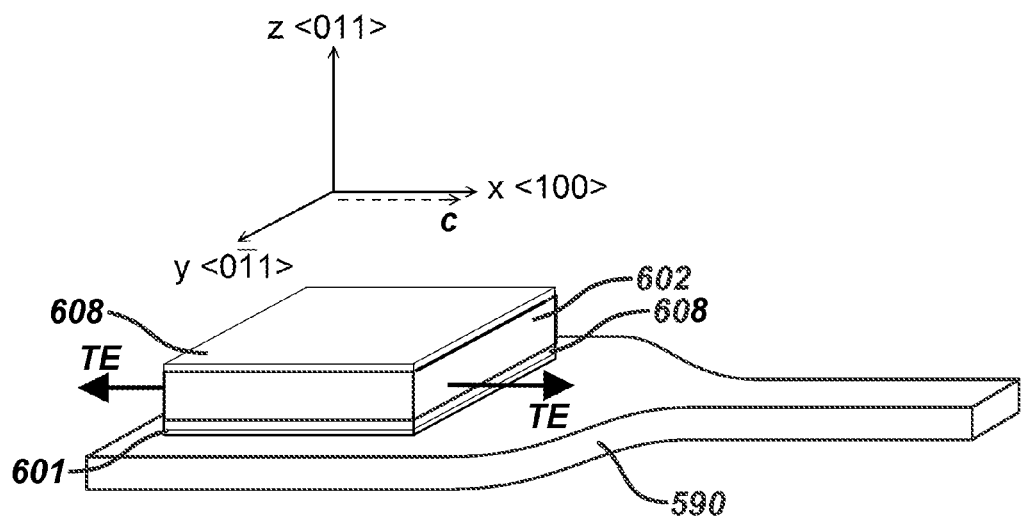
FIGS. 52C and 52D are schematic perspective views of ultrasonic core transducer structures amenable to post-assembly poling.

In manufacturing devices in accordance with the third construction, one can affix a pre-poled transducer 602 upon the transduction portion 594 of the waveguide 590; however, assembly processes employing high temperature/fast cure adhesives or typical brazes may depole the piezoelectric material during the assembly process. Consequently, a preferred method of manufacturing an ultrasonic core, diagrammed in FIG. 52B, involves selecting a single crystal piezoelectric material cut along a predetermined crystallographic plane and disposing said single crystal piezoelectric material between an opposing pair of planar electrodes such that poling the material via the planar electrodes favors the generation of piezoelectric mechanical stress in a direction parallel to the planes of the electrodes. As a result, as shown in FIGS. 52C and D, the transducer 602 may be bonded to the waveguide 590 to assemble the ultrasonic core, and the transducer may be poled after assembly of the ultrasonic core, permitting the use of fast cure adhesives or high temperature brazes. In a first step of the method 1010, one selects a single crystal piezoelectric material and cuts the material to form a plate having major faces coincident with the <011> crystallographic plane. In a second step 1020, one adds at least one planar electrode member 608 to a major face of the plate. It will also be apparent that an opposing planar electrode member 608 may be added to the opposite major face of the plate, and that either or both electrode members may be subdivided or otherwise configured as a plurality of electrode members, etc. In a third step 1030, one bonds the opposite major face of the plate to a side of a longitudinally elongated, generally planar waveguide 590. As in the fifth embodiment generally, it is preferred that the waveguide 590 is constructed from a single crystal or polycrystalline material, and highly preferred that the material be principally silicon. It should be noted that the transduction portion 594 of the waveguide 590 may itself serve as a planar electrode (in the manner illustrated in FIG. 42), or be provided with an adhesion layer or electrical contacts 612 (for example, contacts such as those illustrated in FIG. 43) to be brazed to the opposing planar electrode member 608. The bonding material used may be a conductive adhesive, e.g., conductor-filled epoxies or acrylates such as the epoxies disclosed in U.S. Pat. No. 4,210,704, or a braze, such as those described in Table 1. In a fourth step, 1040, one applies a poling current across the planar electrode member 608 and plate, to the waveguide 590 or opposing planar electrode member 608, to pole the single crystal piezoelectric material in the <011> direction (i.e., as used in the art, a direction perpendicular to the <011> crystallographic plane).

Figure 52D:
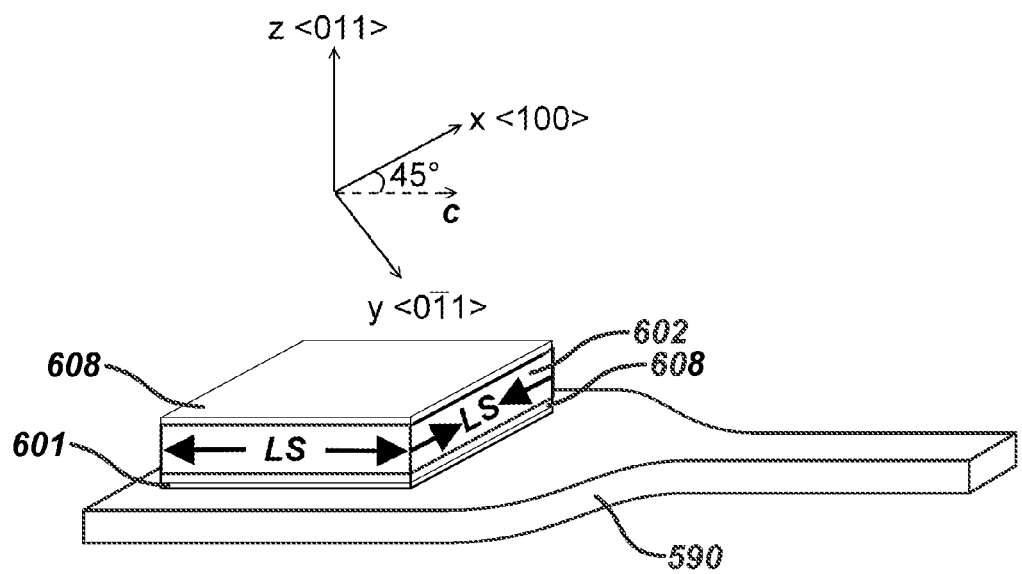

The transducer 602 formed by this method may, depending upon cut direction "c," be operated in a transverse extension mode ($d_{31}$, illustrated as "TE"; cut direction zxt+0°) as shown in FIG. 52C, or a longitudinal shear mode ($d_{36}$, illustrated as "LS"; cut direction zxt+45°) as shown in FIG. 52D. For a transverse extension mode transducer, it is preferred that the ratios of longitudinal extent to lateral extent between edges of the transducer and longitudinal extend to thickness each be greater than 5 to 1. For a longitudinal shear mode transducer, it is preferred that the ratios of longitudinal extent to lateral extent between edges of the transducer and longitudinal extent to thickness each be greater than 3.5 to 1. Exemplary single crystal piezoelectric materials suited for use with the method include PMN-PT (lead magnesium niobate with lead titanate dopant) and PIN-PMN-PT (lead indium niobate-lead magnesium niobate with lead titanate dopant), available from sources such as H.C. Materials Corp. of Bolingbrook, Ill., USA.

Figure 53A:
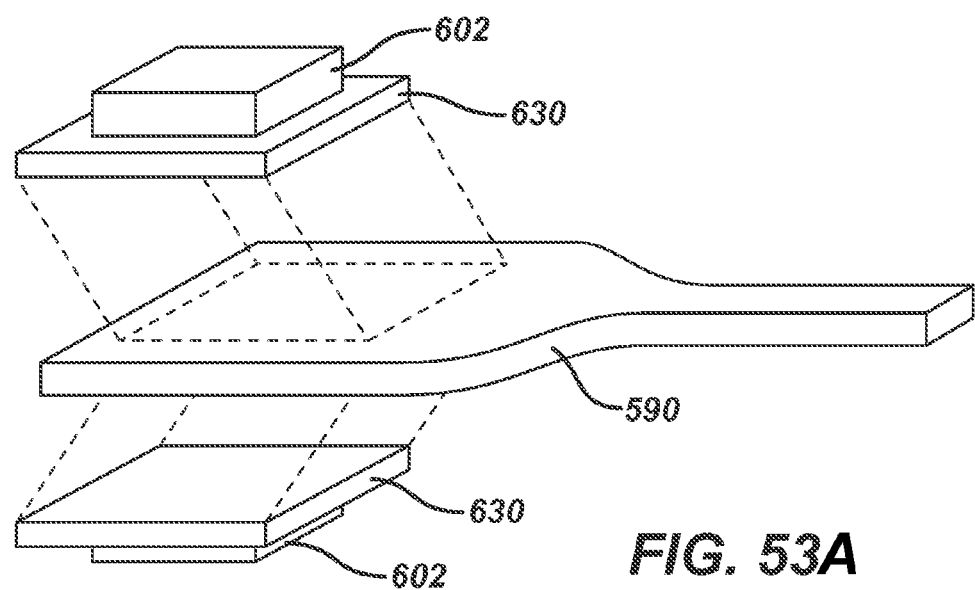
FIG. 53A is an exploded perspective view of a transduction portion of a waveguide including a carrier-transducer subassembly.

In one alternative to the third construction, shown in FIG. 53A, the transducer 602 is indirectly bonded to a carrier 630 by an adhesive or braze 601, and the carrier 630 is subsequently bonded to the transduction portion 594 as a subassembly. The carrier 630 is preferably constructed from silicon, but other similarly temperature resistant substrates may be used. The carrier-transducer subassembly may advantageously be prepared separately from preparation of the waveguide 590 and non-transducer structures such as the first resonator 592 and the second resonator 596, as well as any end effector portion 520a. The carrier 630 may also be bonded to the transduction portion 594 with a low temperature process, permitting the emplacement and use of surface mount-like electrical contacts, e.g., electrical contact 612, on the carrier 630 and/or waveguide 590 during the attachment of the carrier-transducer subassembly to the transduction portion 594, and preventing the potential depoling of the transducers 602. The carrier 630 could then be underfilled with a non-conductive adhesive around the joined surface mount electrical contacts. Alternately, the carrier 630 may be bulk-doped silicon, permitting conductive direct bonding to a bulk-doped silicon transduction portion 594 via a low-temperature silicon fusion process.

This may be particularly advantageous if the transducer 602 would otherwise be bonded to silicon with a high temperature braze (solidus melting point of >275° C.). In a further variation, the carrier 630 is indirectly bonded to the transduction portion 594 by a low temperature braze 601, such as the Sn—Bi and Sn—In alloys listed in Table 1. In yet another variation, the carrier 630 is indirectly bonded to the transduction portion 594 by a conductor-filled epoxy, such as those disclosed in U.S. Pat. No. 4,210,704, or a conductor-filled acrylate, such as those disclosed in European Patent No. 0144741. In another further variation, a silicon carrier 630 is laminated to the transduction portion 594 by silicon-glass-silicon anodic bonding. Silicon dioxide layers can be grown on the silicon carrier 630 and transduction portion 594, and a glass layer can be sputtered or deposited by a sol-gel process upon one of the silicon dioxide layers, followed by assembly and bonding using a DC voltage applied across the assembly, resulting in covalent bonding between the silicon dioxide and glass layers. Due to the insulating nature of the anodic bonding surface preparation and bond, the carrier may be provided with electrical contacts 612 and conductive paths 610 in the manner illustrated and discussed above with respect to FIGS. 42 and 43 and below with respect to FIGS. 58A-59B.

Figure 53B:
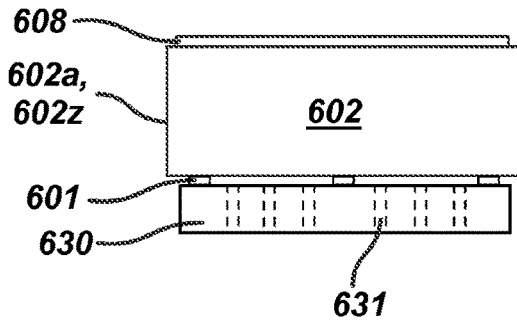
FIGS. 53B and 53C are detailed edge and side views, respectively, of a carrier-transducer subassembly amenable to post-subassembly poling.
Figure 53C:
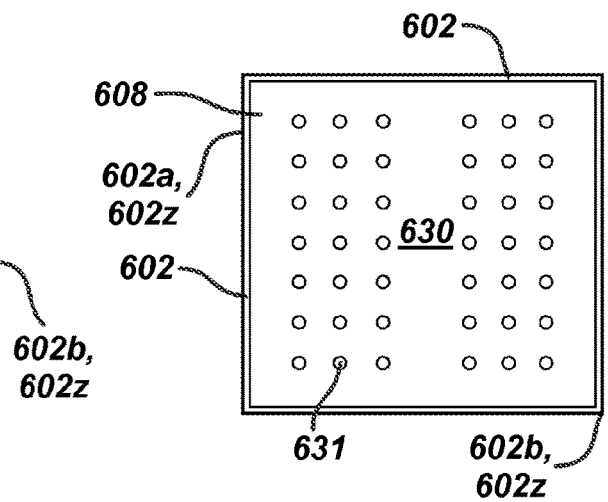
Figure 53D:
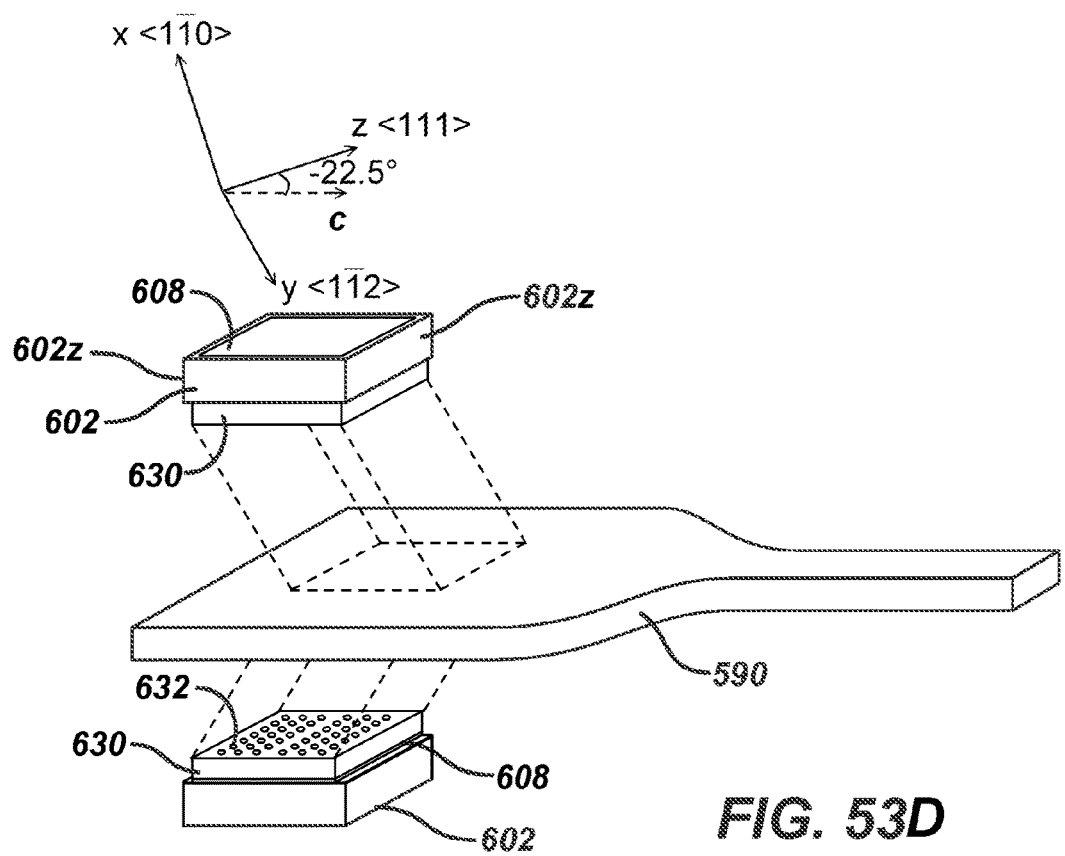
FIG. 53D is exploded perspective view of a transduction portion of a waveguide including the carrier-transducer subassembly of FIGS. 53B and 53C.
Figure 53E:
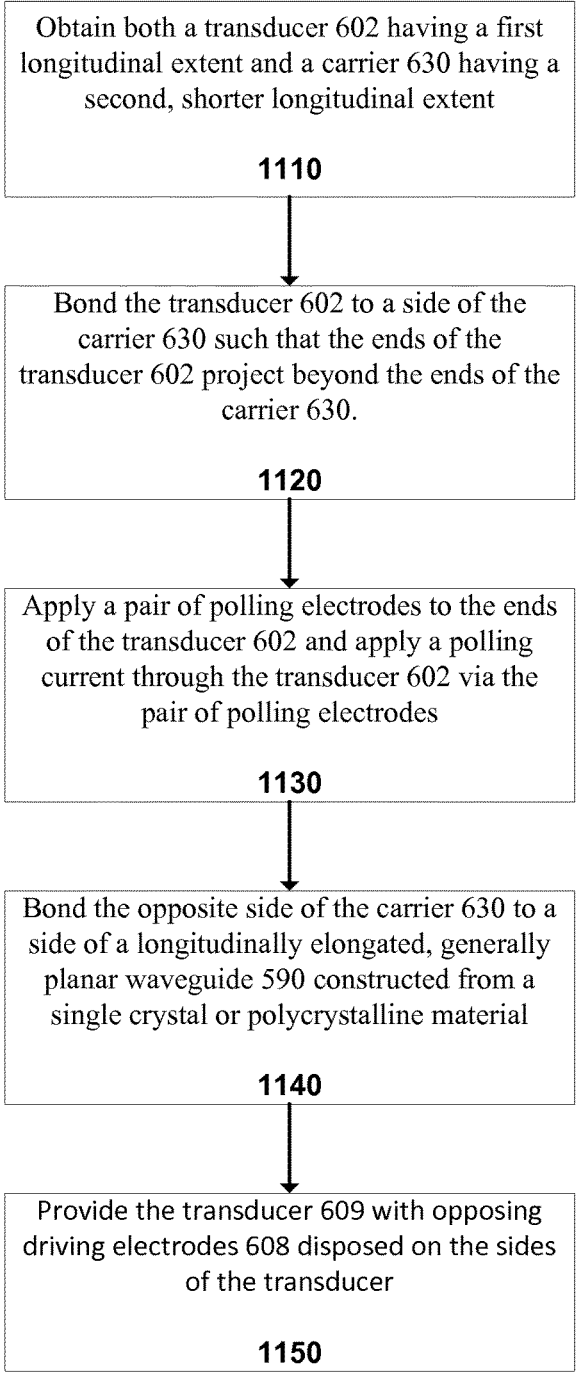
FIG. 53E is a diagram of a process for assembling a carrier-transducer subassembly with post-assembly poling.

In a variation of the alternative, shown in FIGS. 53B-53D, the transducer 602 is dimensioned to have a greater longitudinal extent than that of the carrier 630, i.e., the ends of the transducer 602 project beyond the ends of the carrier 630. The larger transducer 602 (or smaller carrier 630) advantageously allows the subassembly to be polled after the transducer 602 is affixed to the carrier 630 by applying electrodes to poling surfaces 602z disposed on the proximal end 602a and distal end 602b of the ultrasound transducer 602. The relative sizing of the transducer 602 and carrier 630 are not critical to poling via the transducer end surfaces, but advantageously reduce the precision and accuracy required for polling electrode positioning versus arrangements such as that shown in FIG. 53A, in which poling electrodes must essentially abut the carrier 630 in order to fully contact the transducer ends. Consequently, a preferred method of manufacturing an ultrasonic core, diagrammed in FIG. 53E, involves the step 1110 of obtaining both a transducer having a first longitudinal extent and a carrier having a second, shorter longitudinal extent. In a second step of the method 1120, one bonds the transducer 602 to a side of the carrier 630 to form a subassembly in which the ends of the transducer 602 project beyond the ends of the carrier 630. In a third step of the method 1130, one applies a pair of poling electrodes to the ends of the transducer 602 and applies a poling current through the transducer 602 via the pair of poling electrodes. In a fourth step of the method 1140, one subsequently bonds the opposite side of the carrier 630 to a side of a longitudinally elongated, generally planar waveguide 590 constructed from a single crystal or polycrystalline material. It is important to note that the transducer 602 is preferably not bonded to the carrier 630 across the entirety of their mutually opposing sides, but rather by a discontinuous pattern of balls or edge-to-edge oriented strips of bonding material 601. This first bonding material 601 is preferably a non-conductive, high strength adhesive such as unfilled epoxies, urethane acrylates, or the like, but could be a conductive high strength adhesive or low flow braze.

In a subsequent step 1150, the transducer 602 may be provided with opposing driving electrodes 608, as illustrated in FIGS. 53B and 53C. The otherwise exposed side of the transducer 602 may be provided with a first driving electrode 608 by screen printing, shadow mask vapor deposition, or the like. The side of the transducer 602 bonded to the carrier 630 may be provided with a second driving electrode 608 by underfilling the transducer with a second bonding material which is conductive, such as a metal-filled or carbon-filled epoxy or acrylate, or with a low temperature, free flowing braze. Such an underfill serves to surround the other bonding material 601 between the transducer 602 and carrier 630 and to provide a discontinuous drive electrode 608 or, where the other bonding material 601 is a conductive material, a composite drive electrode 608 for conducting current across the sides of the transducer 602. In one variation of the method step, the underfill may be introduced to the space between opposing sides of the transducer 602 and carrier 630 from the edges and/or ends of the transducer. In another variation of the method step, the underfill may be introduced to the space between opposing sides of the transducer 602 and carrier 630 through a plurality of through-holes 631, similar to through-silicon vias (or TSVs), disposed in the carrier 630 underneath the transducer. In this later variation, the underfill may advantageously be introduced and formed as part of the assembly process of the carrier 630 upon the transduction portion 594 of the waveguide 590, and remain at least partially disposed within the through-holes 631 so as to serve as an electrical connection to the transduction portion. In an exemplary construction, illustrated generally in FIG. 53D, a carrier-transducer subassembly formed by this method is longitudinally polled and operated in a transverse shear mode (d15, illustrated as "TS"; cut direction xzt −22.5°).

Figure 53F:
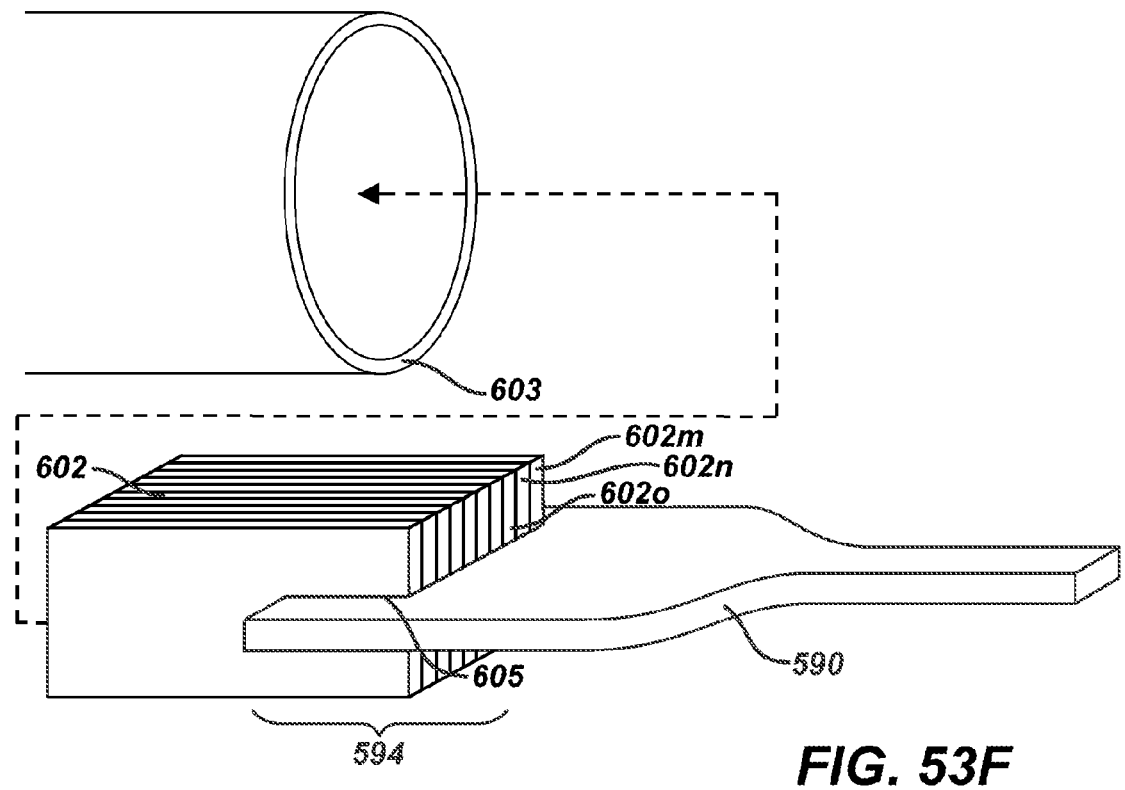
FIGS. 53F and 53G are partially exploded perspective views of magnetostrictive ultrasonic cores for use with a surrounding and encased coil.
Figure 53G:
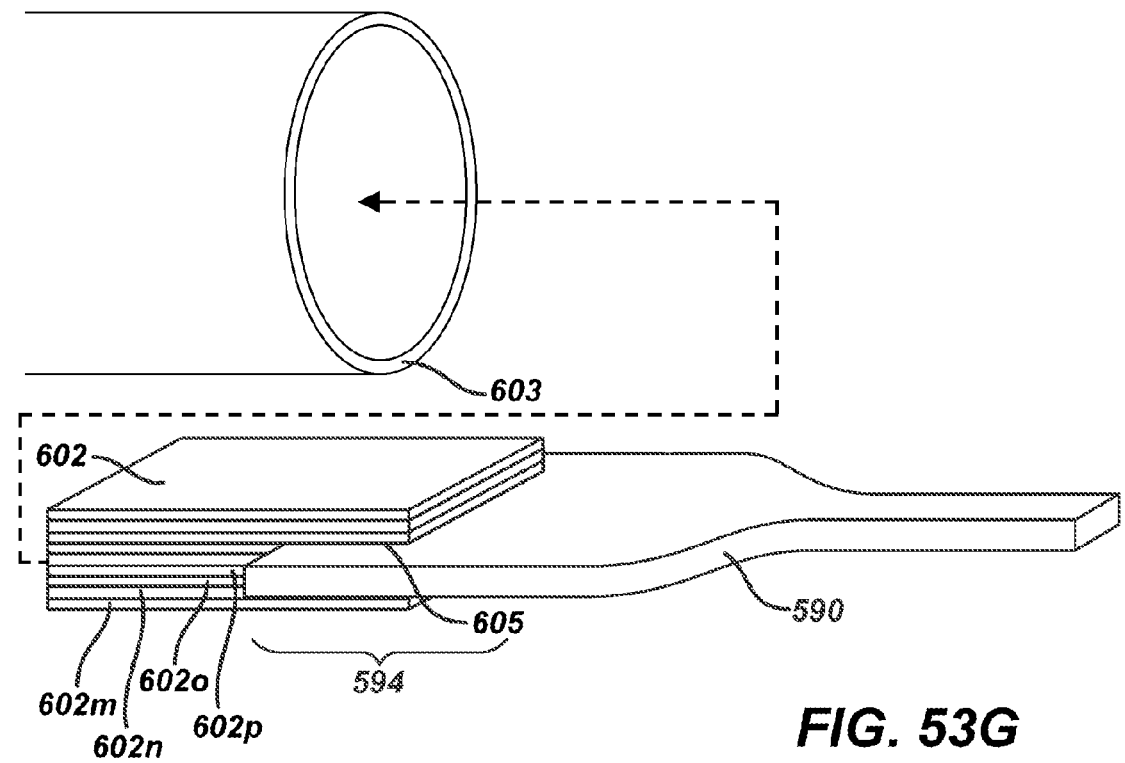

In another alternative to the third construction, shown in FIGS. 53F and 53G, a magnetostrictive transducer 602 and surrounding encased coil 603 may be substituted for the piezoelectric materials otherwise described. The magnetostrictive transducer 602 advantageously does not require poling, and thus may be quickly and securely bonded to the waveguide 590 using a fast cure adhesive or high temperature braze 601. The magnetostrictive transducer 602 may include an aperture 605 configured to receive a proximal end portion of the transduction portion 594 of the waveguide 590, in which case the first resonator 592 included in other constructions of the fifth embodiment may be omitted. The magnetostrictive transducer 602 is preferably a laminated structure formed from multiple layers 602m, 602n, 602o, etc. of magnetostrictive material so as to reduce eddy current losses during excitation within an oscillating magnetic field. Thus, in a first construction of the alternative, the aperture 605 may be formed parallel to the layers of magnetostrictive material by omitting a distal portion of one or more layers of magnetostrictive material, e.g., 602p, and in a second construction of the alternative, the aperture may be formed perpendicular to the layers of magnetostrictive material by any of various known techniques (molding, cutting, etc.). The transduction portion 594 is disposed within the aperture and secured by an adhesive or a braze 601, such as one from Table 1, in order to minimize acoustical impedance between the transducer 602 and the waveguide 690. Because operation of the magnetostrictive ultrasonic core, including transducer 602 and waveguide 590, requires the application of electrical current to only the encased coil 603, this alternative is particularly well suited for use in instruments employing the fluid communications configuration shown in FIG. 23—the encased coil 603 may be more easily insulated to prevent electrical leakage into irrigation fluids, cooling fluids, or the like communicated between the encased coil 603 and the ultrasonic core 510 than the more complex transducer structures 600 and transduction portions 594 of the waveguide 590 in other constructions.

Figure 54:
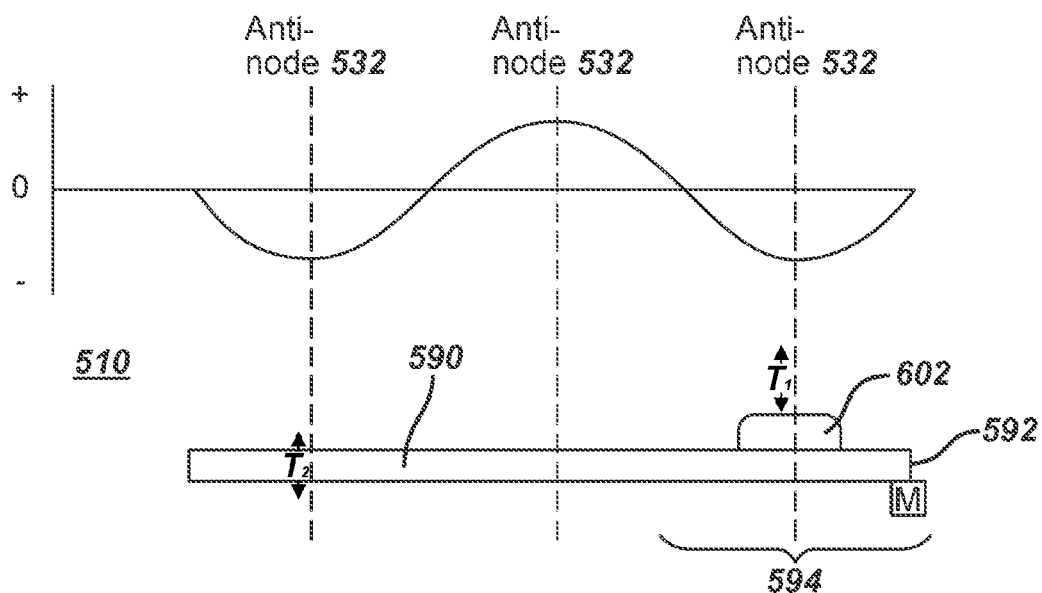
FIGS. 54 and 55 are schematic edge views of ultrasonic core transducer structures.
Figure 55:
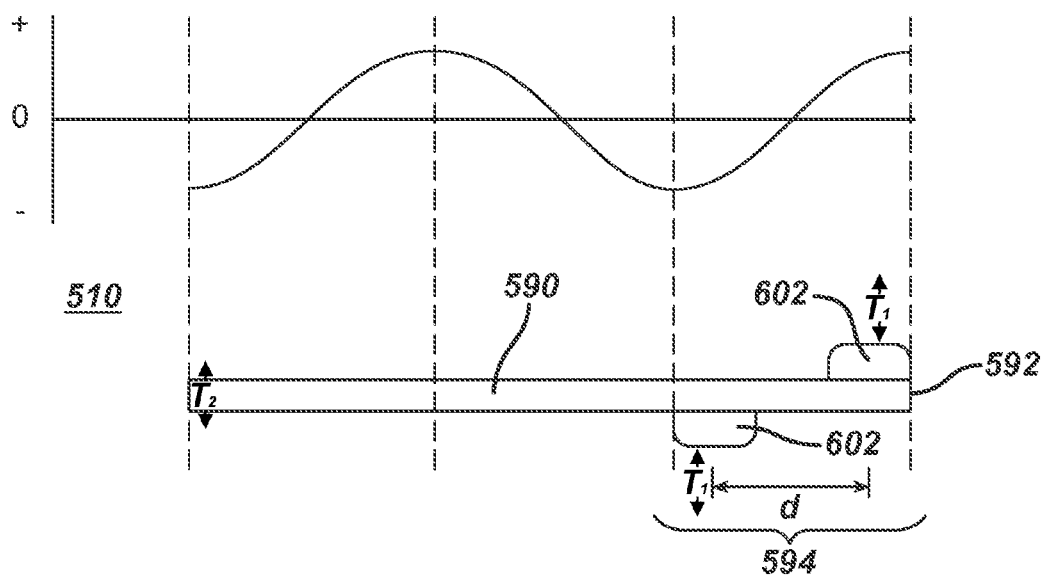
Figure 56:
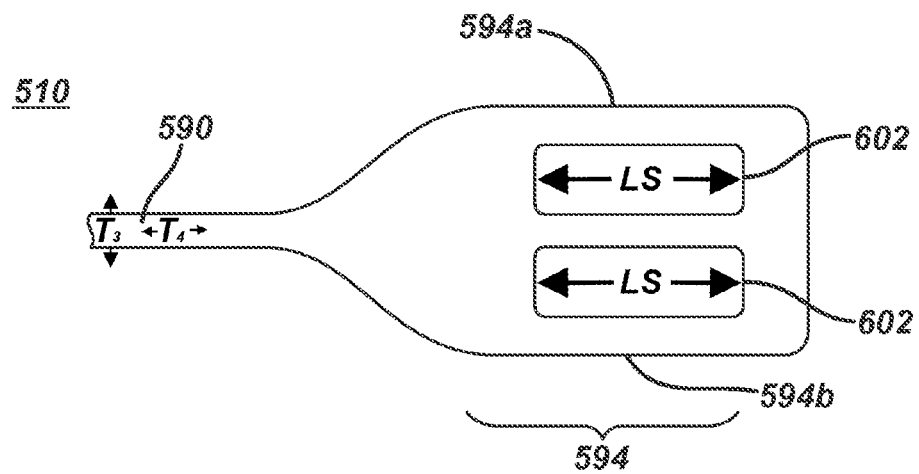
FIG. 56 is a schematic side view of an ultrasound core transducer structure.

In a fourth construction of the second expression, shown in FIGS. 54-56, at least one transducer 602 is affixed to the transduction portion 594 of waveguide 590 and configured to create a transverse mode of vibration. In a first variation of the fourth construction, shown in FIG. 54, a transducer 602 is affixed to an exposed side of the transduction portion 594, and configured to operate in a transverse resonant mode "$T_1$" perpendicular to the plane of the waveguide 590. No transducer is affixed to the opposite exposed side of the transduction portion 594. A proximal portion of the transduction portion 594 is fixed against vibration, e.g., by a handpiece mount M, at a longitudinal distance, d, from the center of mass of the transducer 602. Operation of the transducer 602 creates an intermediate or stack anti-node 533 at the center of mass of the transducer 602, and a transverse mode of vibration "$T_2$" out of the plane of the waveguide 590. Variation of the longitudinal distance d will vary the frequency of the resonant mode of vibration, i.e., the wavelength of the standing wave. In a modification of the first construction, a large end mass 640 is affixed to the first resonator or proximal end portion 592 to create a virtual node 534 due to the resistance of the large rest mass to displacement. Varying the longitudinal separation of the centers of mass of the transducer 602 and the end mass 640 will vary the frequency of the resonant mode of vibration.

In a second variation of the fourth construction, shown in FIG. 55, a first transducer 602 is affixed to an exposed side of the transduction portion 594, and a second transducer 602 is affixed to an opposite exposed side of the transduction portion 594. The centers of mass of the first and second transducers 602 are separated by a longitudinal distance, d, and configured to operate in a transverse resonant mode "$T_1$" perpendicular to the plane of the waveguide 590, with the first transducer 602 180 degrees out of phase with the second transducer 602. Operation of the transducers creates a transverse mode of vibration "$T_2$" out of the plane of the waveguide 590, as well as a node between the first and second transducers at d/2. Variation of the longitudinal distance d will vary the frequency of the resonant mode of vibration, i.e., the wavelength of the standing wave, as well as the amplitude of the mode of vibration.

In a third variation of the fourth construction, shown in FIG. 56, a first transducer 602 is affixed to the transduction portion 594 adjacent to one edge 594a of the transduction portion, and a second transducer 602 is affixed to the transduction portion 594 adjacent to the opposite edge 594b of the transduction portion, with the first and second transducers being separated by the central longitudinal axis of the waveguide 590. The first and second transducers 602 are configured to operate in a longitudinally-oriented shear mode "LS" where the first transducer 602 is 180 degrees out of phase with the second transducer 602. Operation of the transducers creates a primary transverse mode of vibration "$T_3$" within the plane of the waveguide 590, and a secondary longitudinal mode of vibration "$T_4$."

In implementations of the second expression, the transducer 602 may be configured as a multi-element piezoelectric, electrostrictive, or, in some instances, magnetostrictive transducer stack. A multi-element transducer stack, in general, increases the power and amplitude of the modes of vibration created within the waveguide. A magnetostrictive transducer is preferably configured as a multi-element transducer stack in order to reduce eddy current losses during magnetic excitation. It is to be understood that references to an ultrasound transducer 602, with respect to the fifth embodiment in particular and to combinations with other embodiments or known devices generally, are intended to include both a transducer configured as a single element transducer and a transducer configured as a multi-element transducer stack.

Figure 57A:
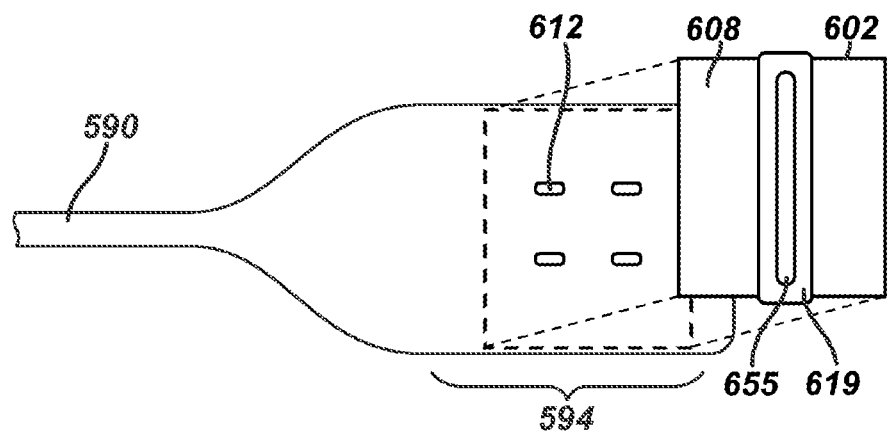
FIG. 57A is a side view of an ultrasound core configured for surface mounting of a transducer 602 on a transduction portion 594.
Figure 57B:
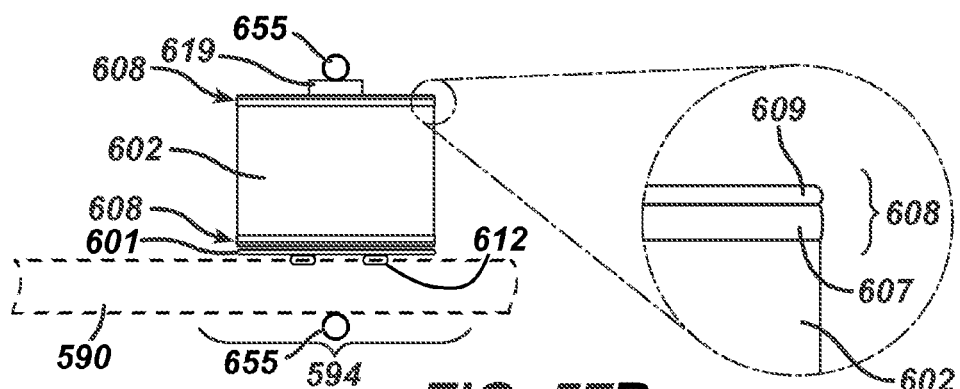
FIG. 57B is an edge view, with detail inset, of an ultrasound transducer electrode structure and transduction portion electrical contact 612. Transduction portion 594 of waveguide 590 is shown in phantom lines for sake of clarity.

In a fifth construction of the second expression, shown in FIGS. 57A and 57B, the transduction portion 594 is configured to have at least one electrical contact 612 disposed on an exposed side of the transduction portion 594, and the transducer 602 is configured to have an electrode portion 608 for surface mount electrical connection to the electrical contact 612, with the electrode portion 608 electrically joined to the electrical contact 612 by a solder or braze 601. The electrical contact 612 and transduction portion 594 may be configured as previously described, however in this construction the electrical contact may be disposed adjacent to or even under the transducer 602, which, rather than being directly bonded to the transduction portion 594, is indirectly bonded to the transduction portion through at least the electrode portion 608. The transducer 602 may also be bonded to the transduction portion 594 with an epoxy or other adhesive for mechanical stability. The electrode portion 608 may have a similar construction to that of the electrical contact 612, with, for example, a nickel pad 607 and a gold top coat 609. As shown in the figures, an opposing electrode portion 608 may be formed upon the opposite side of the transducer 602, and an electrical source such as a wire or shim 619 may be soldered or brazed to the exposed side of the transducer 602 and opposing electrode portion 608. In a variation of this construction, an acoustically isolating mount 655, e.g., an o-ring or elastomeric stand-off mount, abuts the side of transducer structure and may be used instead of soldering to clamp a shim 619 against the opposing electrode portion 608, or in addition to soldering for the more limited purpose of mounting the ultrasonic core within a housing 650 (not shown in these figures).

Figure 58A:
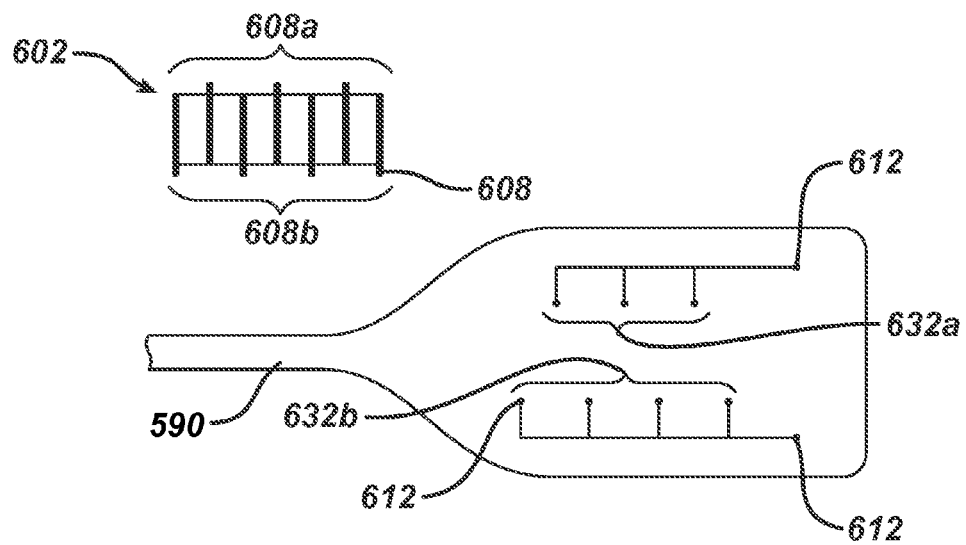
FIG. 58A is a schematic side view of an ultrasound transducer and waveguide configured for surface mount assembly.
Figure 58B:
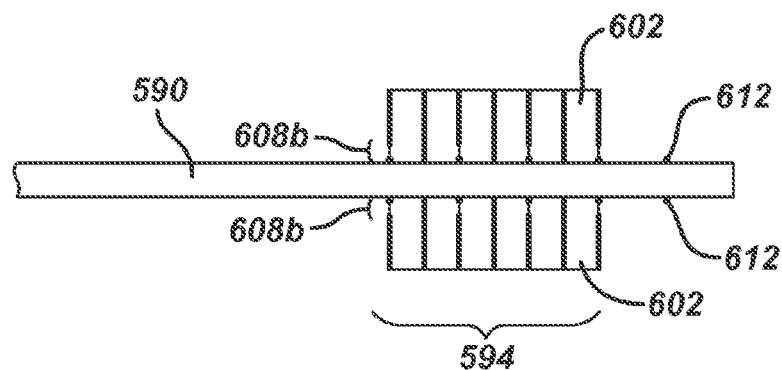
FIG. 58B is a schematic edge view of a waveguide with a surface mounted ultrasound transducer.

In a second variation of the fifth construction, shown in FIGS. 58A and 58B, the transduction portion 594 is configured to have first 632a and second 632b generally linear arrays of electrical contacts 612 disposed on an exposed side of the transduction portion 594. The first array 632a is electrically connected to a furst remote electrical contact 612 which is electrically connectable to an electric source, and the second array 632b is electrically connected to a second remote electrical contact 612 which is electrically connectable to ground. The electrical connections may be the embedded paths discussed above, or may be surface traces of a conductive material overlaying an oxygen rich surface layer, e.g., silicon dioxide ($SiO_2$). Such surface traces may be formed by screen printing techniques using materials such as DuPont 7723, a low-temperature firing silver ink suitable for printing on glass. The transducer 602 is configured as a multi-element transducer stack having first 608a and second 608b generally linear arrays of electrode portions 608 projecting from stack electrodes disposed between every element of the stack, with the first 608a and second 608b arrays being alternatingly connected to successive stack electrodes through the stack. The first 608a and second 608b arrays of the transducer 608 are configured for surface mount electrical connection to the first 632a and second 632b arrays of electrical contacts 612, respectively, with the individual electrode portions 608a and 608b electrically joined to corresponding individual electrical contacts 612 by a braze 601. In an exemplary configuration shown in FIGS. 58A and 58B, the transducer stack is longitudinally oriented, and may operate in a longitudinal extension mode ($d_{33}$) to generate a longitudinal standing wave in the waveguide 590.

Figure 59A:
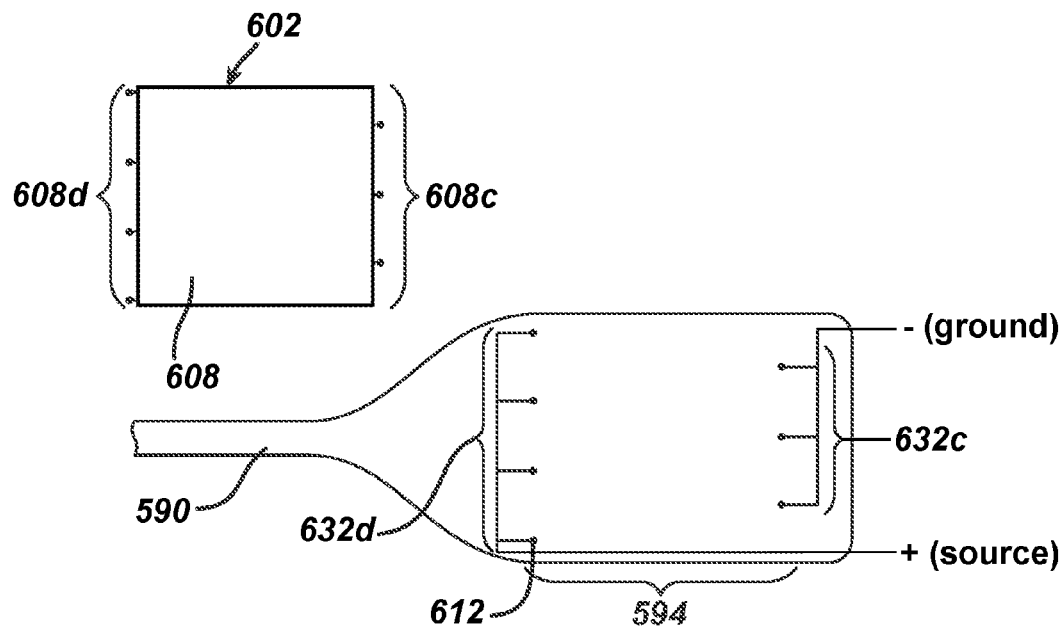
FIG. 59A is a schematic side view of an ultrasound transducer and waveguide configured for surface mount assembly.
Figure 59B:
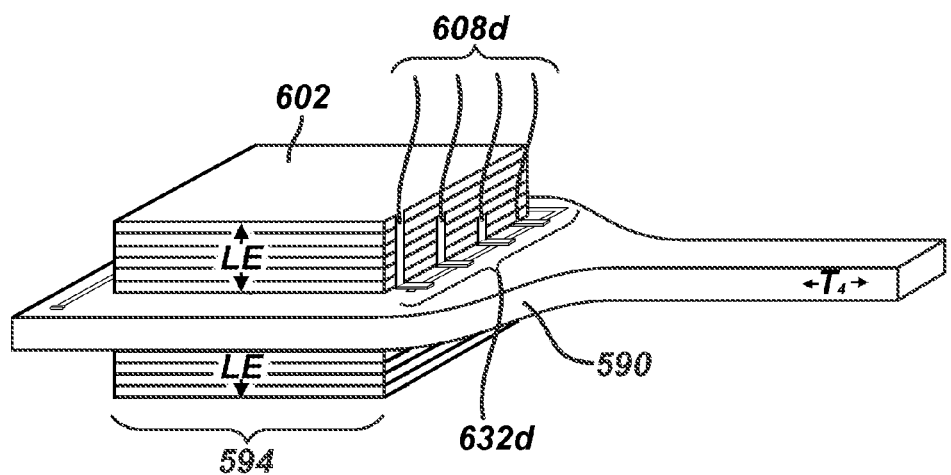
FIG. 59B is a perspective view of the an ultrasound transducer and waveguide of FIG. 59A.
Figure 60:
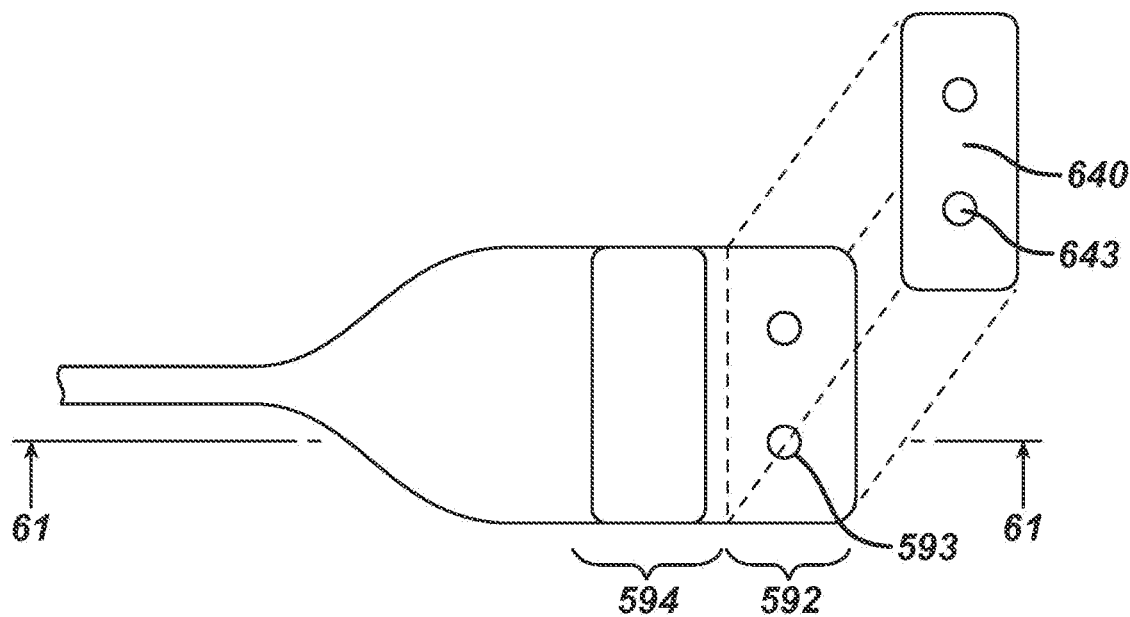
FIG. 60 is an exploded side view of a first resonator of a waveguide.

In other variations of the fifth construction, illustrated in FIGS. 59A and 59B, the transduction portion 594 may be configured to have a first plurality of source electrical contacts 632c and a second plurality of ground electrical contacts 632d. Both pluralities 632c and 632d may be disposed on an exposed side of the transduction portion 594, with the first plurality 632c being electrically connectable to an electric source and the second plurality 632d being electrically connectable to an electric ground. The transducer 602 is again configured as a multi-element transducer stack having a first plurality of source electrical contacts 608c, electrically connected to the elements of the stack to supply power, and a second plurality of ground contacts 608d, electrically connected to the elements of the stack to provide ground. The first 608c and second 608d pluralities of contacts of the transducer stack may project from the transducer stack, may be disposed upon the ends and/or edges of the transducer stack, or a combination of foregoing, and provide terminal legs or pads for bonding to the first plurality 632c and second plurality 632d of electrical contacts 632c of the transduction portion 594, respectively. For example, as illustrated in FIG. 59B, the first plurality 608c (not visible in the view) and second plurality 608d of contacts may be metallic strips projecting from the main body of each electrode 608 and along the ends of the transducer stack 602. Each strip may form a terminal pad for bonding to a corresponding one for the first plurality 632*c* (not visible in the view) and second plurality 632*d* of electrical contacts, which may take the form of electrical contacts 612 or other forms of surface mount pad. Those portions of the strips not constituting the terminal pad may be affixed to the transducer stack by a non-conductive adhesive, formed on or deformed against the transducer stack over an insulating coating, coated with an insulating coating and subsequently deformed against the transducer stack, etc. In the exemplary configuration shown in FIGS. 59A and 59B, the transducer stack is laterally oriented out of the plane of the waveguide 590, and may operate in a longitudinal extension mode ($d_{33}$, with respect to the electrode arrangement) in order to 'squeeze' the transduction portion 594 and generate a longitudinal move of vibration "$T_4$" in the waveguide 590.

Figure 61:
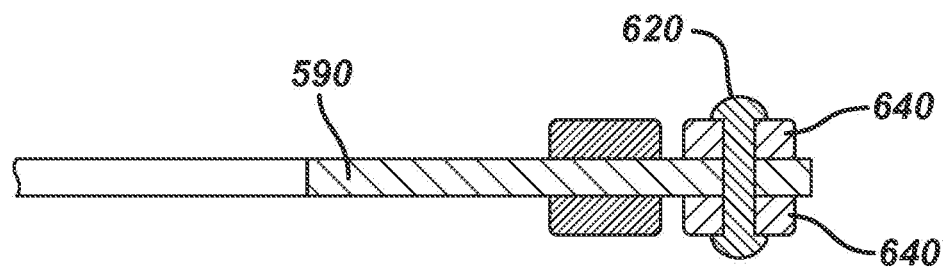
FIG. 61 is a cross-sectional edge view of the waveguide of FIG. 60, including a compressive fastener.

In a third expression of the fifth embodiment, shown in FIGS. 60-66, an end mass 640 is affixed to the first resonator 592 of the waveguide 590. In a first construction of the third expression, shown in FIGS. 60 and 61, the first resonator 592 includes at least one aperture 593 and the end mass 640 includes at least one corresponding aperture 643. The corresponding apertures 593 and 643 are axially aligned and receive a compressive fastener 620, such as a bolt or rivet. As illustrated in FIG. 61, multiple end masses 640 may be affixed to the first resonator 592 by the same compressive fastener 620.

Figure 62:
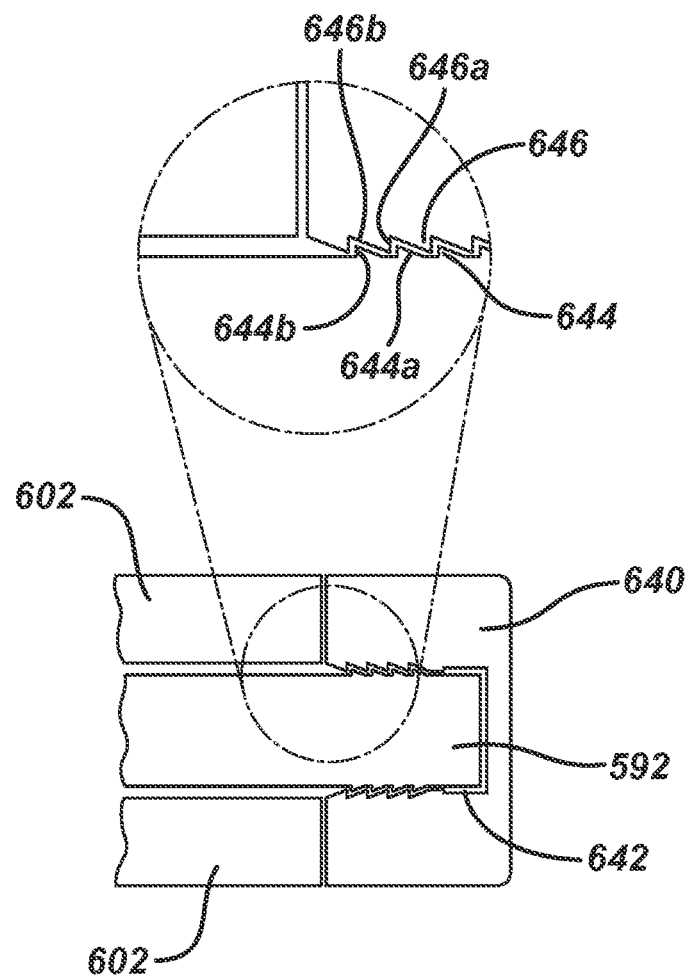
FIG. 62 is an edge view of a first resonator, with inset detail of a toothed connection.

In a second construction of the third expression, shown in FIG. 62, the sides of the first resonator 592 include teeth 644 with substantially inclined proximal surfaces 644*a* and substantially perpendicular distal surfaces 644*b*. The end mass 640 includes a channel 642 configured to receive the first resonator 592 and teeth 646 with substantially vertical proximal surfaces 646*a* and substantially inclined distal surfaces 646*b* corresponding to inclined proximal surfaces 644*a*. Teeth 644 and 646 essentially irreversibly and interlockingly mesh when channel 642 receives first resonator 592. The second construction may be used to compress the transducers 602 as the transducers are formed, or to place pre-formed transducers under compression after they have been affixed to the transduction portion 594 of the waveguide 590.

Figure 63:
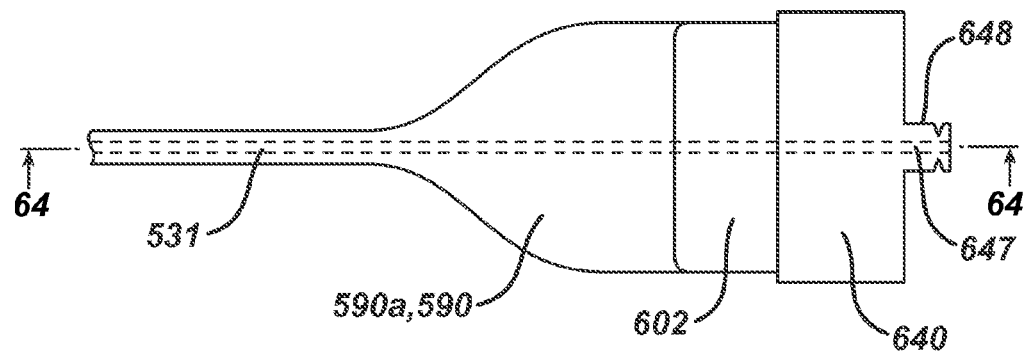
FIG. 63 is a schematic side view of a first resonator and abutting end mass, with interconnecting lumen shown in phantom lines for context
Figure 64:
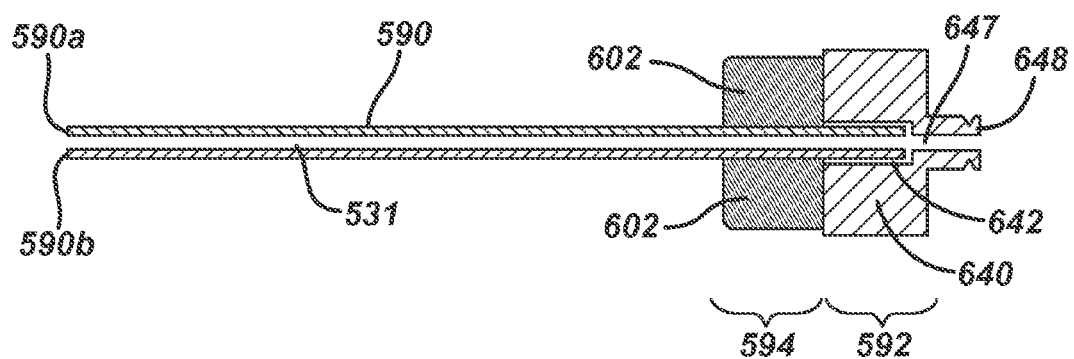
FIG. 64 is a cross-sectional edge view of the first resonator, end mass, and interconnecting lumen structure of FIG. 63.

In a third construction of the third expression, shown in FIGS. 63 and 64, the end mass includes a channel 642 configured to receive the first resonator 592, and is indirectly bonded to the first resonator 592 by an adhesive or braze 601. In variations of the first through third constructions, the first resonator 592 is a laminated structure having a lumen 531, for example, the top structure shown in FIG. 34, and the end mass has a correspondingly positioned lumen 647. The lumen 647 may communicate with a fitting 648, e.g., a luer fitting, on the proximal end of the end mass 640 to permit fluids or other matter to be introduced and/or withdrawn through the lumens 647 and 531.

In some implementations of the constructions of the third expression, the distal end of the end mass 640 may abut a transducer 602. Structures such as the aperture 593 of the first resonator 592 may be configured to require the end mass 640 to longitudinally compress the transducer 602. Structures such as the teeth 644 and 646 of the first resonator 592 and end mass 640 may mechanically lock the end mass 640 into longitudinal compression with the transducer 602. Finally, first resonator 592 and channel 642 of end mass 640 may be dimensioned such that end mass 640 may be bonded to first resonator while end mass is longitudinally compressing the transducer 602. Once the adhesive has cured or the braze has cooled, the ultrasound transducer 602 remains residually compressed by the established bond between the first resonator 592 and the end mass 640.

Figure 65:
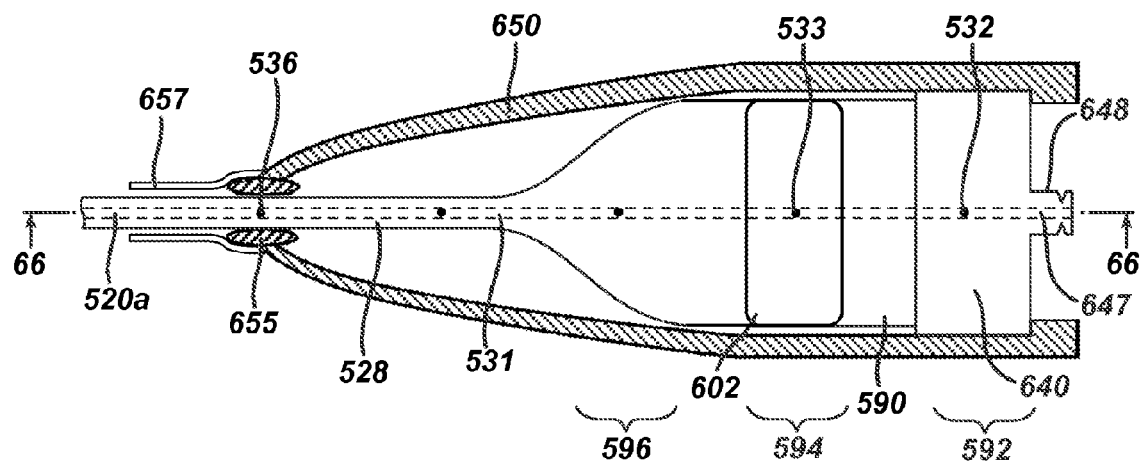
FIG. 65 is a schematic side view of an instrument employing a proximally spaced-apart and fixed end mass, with interconnecting lumen shown in phantom lines for context.
Figure 66:
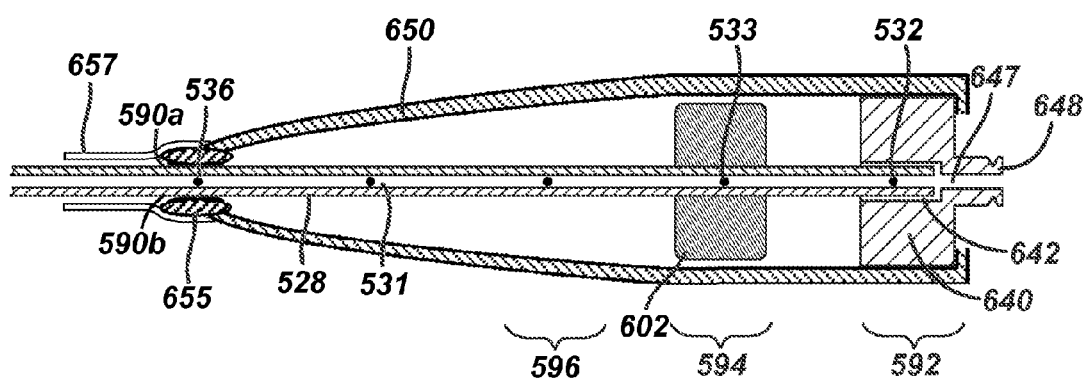
FIG. 66 is a cross-sectional edge view of the instrument of FIG. 65.

In other implementations of constructions of the third expression, shown in FIGS. 65 and 66, the end mass 640 may be proximally spaced apart from the transducer 602. In particular, end mass 640 may be spaced apart from the transducer 602 and sized and/or fixed into place so as to function as a virtual node in the designed, or principal, mode of vibration of the ultrasonic core. End mass 640 is preferably manufactured from a high density material, such as 316 stainless steel, titanium, or aluminum and, optionally, fixed within and with respect to an instrument housing 650 so as to enhance its function as a virtual node. In such implementations, the end mass 640 creates a virtual node 534 proximate the first resonator 592 of the waveguide 590, one or more transducers 602 are disposed at an intermediate or stack anti-node 533 in the transduction portion 594 of the waveguide, and an acoustically isolating mount 655, e.g., an o-ring, is disposed at a distal node 536 of the waveguide 590. The distal node 536 may disposed proximate the distal end of the second resonator 596 or may be disposed within a connecting portion of the end effector 620*a*, such as an ultrasonically active shaft portion 528, which is shown as a monolithically coupled portion of the waveguide. The relative spacing between the virtual node 534, intermediate anti-node 533, and distal node 536 establish a primary frequency (or wavelength) for the mode of vibration, but those of skill in the art will appreciate that the transducer(s) 602 may be operated at harmonics of this primary frequency in order to achieve a desired balance between the length of the instrument housing 650 and the frequency of the resonant mode of vibration transmitted to the end effector 620*a*.

As further illustrated in FIGS. 65 and 66, in an exemplary instrument for shear-thinning a dermal filler and/or deep tissue dissection, the instrument housing 650 may include a sheath 657 projecting over the end effector 520*a* to protect patient tissue at an insertion entry point. As shown, the sheath 657 may be a rigid, generally annular, and concentrically mounted sheath projecting over ultrasonically active portions of the end effector 520*a* proximal of its distal-most end. However, those of skill in the art will recognize that the sheath 657 could instead be longitudinally flexible, creased sheath, such as the one shown in FIG. 25, so as to function similarly to the sheaths of the fourth embodiment. In such constructions, the sheath may be removably mounted to the distal end of the instrument housing 650 so as to be disposable or so as to allow differing extents of the distal-most end of the end effector 520*a* to be exposed. Alternately, the sheath 657 could instead be configured similarly to the sheath 446 of the fourth embodiment, with a proximally adjoining sheath segment, or the instrument housing 650 itself, providing a spring-biased mechanism configured to normally bias the sheath 657 distally from the adjoining sheath segment or housing. The sheath 657 may then compress to expose proximal portions of the end effector upon abutting against tougher patient tissues, such as muscle fascia or cartilage, while protecting overlying subcutaneous fat or dermal layers alongside the insertion track. The lumens 531 and 647, as first introduced above, may be used to introduce dermal fillers, irrigation fluids, and the like, and/or to provide suction in the operating field during a procedure.

Other Exemplary Configurations and Applications

Figure 67:
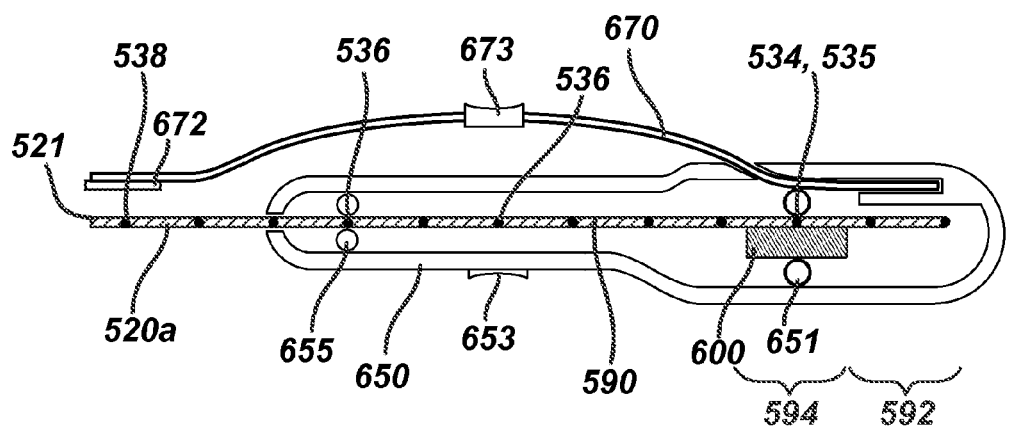
FIG. 67 is a schematic edge view of an exemplary instrument including the ultrasonic core of the fifth embodiment.
Figure 68:
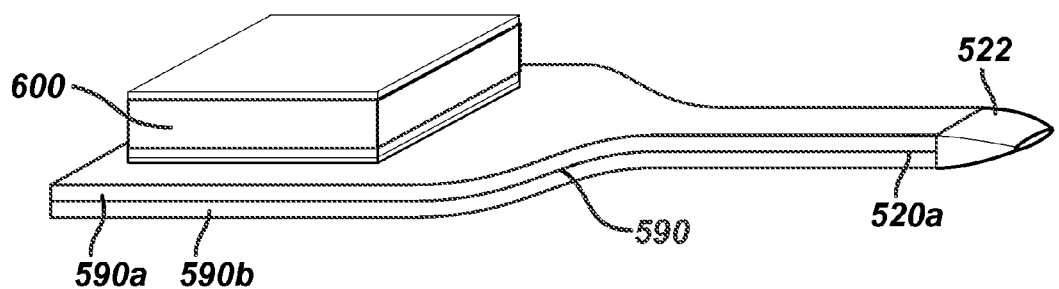
FIG. 68 is a perspective view of an exemplary ultrasonic core for an ultrasonic surgical instrument including a composite distal tip.
Figure 69A:
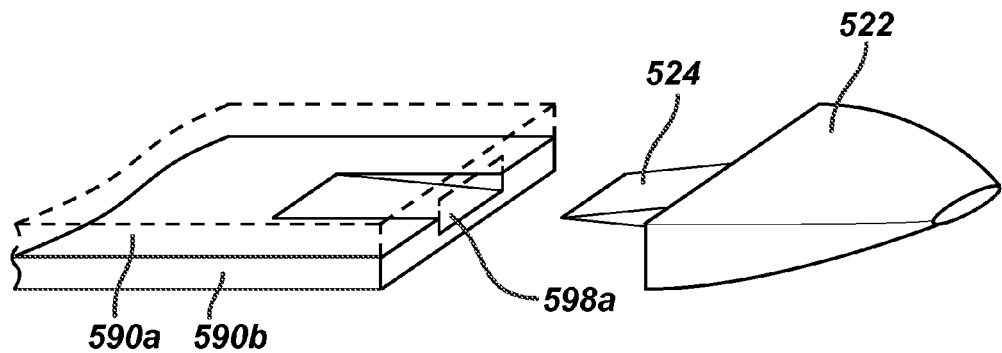
FIG. 69A is an exploded perspective view of one construction of the composite distal tip of FIG. 68. The exterior of the top layer of the end effector/waveguide is shown in phantom lines for sake of clarity.
Figure 69B:
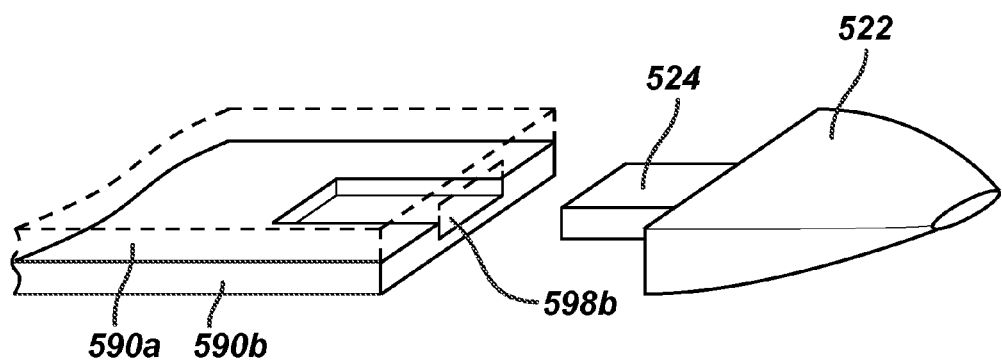
FIG. 69B is an exploded perspective view of another construction of the composite distal tip of FIG. 68. The exterior of the top layer of the end effector/waveguide is shown in phantom lines for sake of clarity.
Figure 69C:
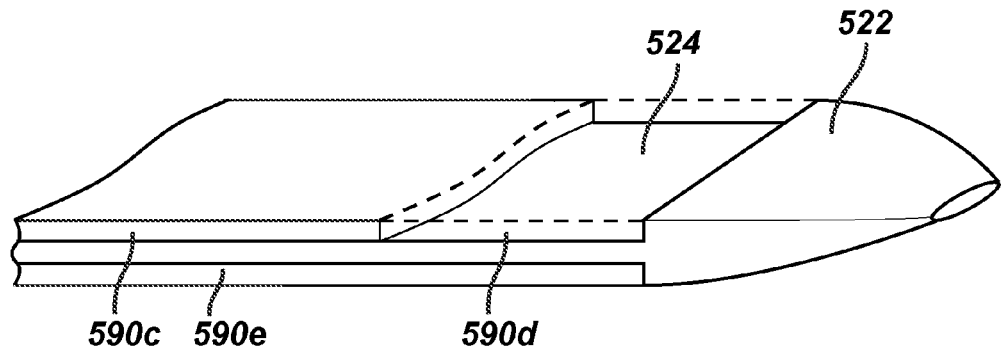
FIG. 69C is a perspective view of yet another construction of the composite distal tip of FIG. 68. A portion of the top layer of the end effector/waveguide is shown in phantom lines for sake of clarity.

FIG. 67 illustrates an exemplary ultrasonic surgical instrument 700 functioning as an ultrasonic hemostatic forceps. The instrument 700 includes a longitudinally elongated, generally planar waveguide 590, constructed from a single crystal or polycrystalline material, and a transducer structure 600 affixed to the transduction portion 594 the waveguide at a node 534, i.e., a stack node 535. The distal end of the waveguide 590 may include an end effector 520a configured to provide a generally blunt side surface 521 for the coaptation of patient tissue, with the distal end and blunt side surface being positioned at a distal-most anti-node 538. At least the transduction portion 594 of the waveguide 590 and the transducer structure 600 are mounted within an instrument housing 650. The mounting may include a first acoustically isolating mount 651, e.g., an o-ring, disposed about the waveguide 590 at a proximal-most node, e.g., node 534, and a second acoustically isolating mount 655 disposed about the waveguide at distal node 536. As illustrated, the transducer structure 600 is disposed at the proximal-most node 534 and the acoustically isolating mount 651 is also disposed about that transducer structure, however those of skill in the art will recognize that acoustically isolating mount 651 need not necessarily be disposed about the transducer structure 600, but may instead be disposed about the first resonator 592 of the waveguide 590, with the transducer structure 600 affixed to the transduction portion 594 at more distally located stack node.

The instrument 700 further includes a longitudinally elongated and flexible tine 670 projecting from the instrument housing 650 and extending alongside the waveguide 590. The flexible tine 670 is preferably a generally arcuate member configured to distally converge towards the waveguide 590, but it will be appreciated that the tine may be a linearly segmented member, a generally straight member substantially spaced apart from the waveguide 590 at the member's proximal end (so as not to proximally diverge away from the waveguide 590 before distally converging toward the waveguide), an arcuate member substantially spaced apart from the waveguide 590 at the member's proximal end (so as not to proximally diverge away from the waveguide 590 before distally converging toward the waveguide), etc. The flexible time 670 has a tissue pad 672 opposing the blunt side surface 521 of the end effector 520a, and may include an integrally formed or affixed finger pad 673 disposed proximate an intermediate node 535. The housing may further include an integrally formed or affixed finger pad 653 disposed proximate the node 535. Thus, manipulation of the instrument housing 650 and tine 670, or fingerpads 653, 673 where present, may draw together and compress the blunt side surface 521 against the tissue pad 672, permitting the ultrasonic coaptation of patient tissue. Advantageously, the simplified construction, reduced size, and reduced expense allowed by constructions using, e.g., a silicon waveguide 590, permit the forceps surgical instrument 700 to be disposable without requiring mounting upon larger ultrasonic instruments, which may prove unwieldy in ultrasonic microsurgery, and without requiring the cleaning and sterilization of complicated end effector attachment mechanisms.

FIGS. 68 and 69A-C illustrate an exemplary ultrasonic core 800 for an ultrasonic surgical instrument including an end effector 520a configured to function as an ultrasonic tissue ablator. The core 800 includes a longitudinally elongated, generally planar waveguide 590, constructed from a single crystal or polycrystalline material, and a transducer structure 600 affixed to the waveguide. The distal end of the waveguide 590 includes or is configured to provide an end effector 520a having a composite distal tip 522 which is constructed from a dissimilar metallic, glassy, polycrystalline, or crystalline material. The dissimilar material may be selected to provide enhanced durability, ductility, or toughness (as determined by ASTM E1820) in comparison to the waveguide material, and improve resistance to crack propagation in comparison to the base material. For example, for a silicon waveguide 590, the distal tip 522 may be principally comprised of a metal, such as titanium, aluminum, or known surgical alloys, which are relatively ductile in comparison to the bulk material of the waveguide 590. For further example, the distal tip 522 may be principally comprised of a glassy material such as amorphous silicon or a polycrystalline material such as polycrystalline silicon (also called polysilicon). In comparison to single crystal silicon, such materials have substantially enhanced toughness and crack resistance. For yet further example, the distal tip may be principally comprised of a polycrystalline or single crystal sapphire, which is comparatively tougher (in the sense of its ability to absorb energy and plastically deform without fracturing) than the silicon or germanium waveguide materials discussed in the fifth embodiment.

At least the end effector 520a, and preferably the waveguide 590, is a laminated structure including a plurality of planar layers, e.g., 590a, 590b, etc., of the material. The distal tip 522 includes a neck or tang 524 which projects proximally of the distal tip for embedment within the end effector 520a or end effector portion of the waveguide 590. As shown in FIG. 68A, the neck or tang 524 may be tapered its proximal end and secured within a complementary socket 598a configured to receive it. Such a socket may be formed by etching two adjoining layers of base material, e.g., 590a and 590b, to define a proximally tapering blind channel, or other internal void, at each layer's distal-most end, and the neck or tang 524 may be secured to the adjoining layers as described below. Alternatively, as shown in FIG. 68B, the neck or tang 524 may generally planar with generally perpendicular, proximal abutment wall that is secured to end a complementary socket 598b configured to receive it. Such a socket may be formed by etching two adjoining layers of base material, e.g., 590a and 590b, to define a longitudinal blind channel, or other internal void, at their distal-most ends, or by etching or otherwise cutting a socket void in an intermediate layer 590d and laminating adjoining layers 590c and 590e over it, and the neck or tang 524 may be secured to at least one layer (e.g., 590d, or 590a and 590b) as described below. In a variation these constructions, shown in FIG. 68C, the neck or tang 524 may be a full width tang, and constitute the entire distal portion of an intermediate layer 590d in a composite end effector 520a or end effector portion of the waveguide 590. The connection may be formed by foreshortening or removing a distal end of the intermediate layer 590d, and laminating adjacent layers, e.g., a first adjacent layer 590c and a second adjacent layer 590e, to opposite sides of the intermediate layer 509d and tang 524. In such constructions, the neck or tang 524 may be secured via brazing (using materials such as those disclosed in Table 1), via an adhesive layer (such as a urethane acrylate, cyanoacrylate, or epoxy), or via direct bonding, such as that resulting from various silicate silicon-to-sapphire bonding processes known in the semiconductor manufacturing arts. Where brazing is used, the material is preferably a tungsten or gold eutectic braze so as to provide a strong but low impedance acoustic joint between the materials.

Figure 70:
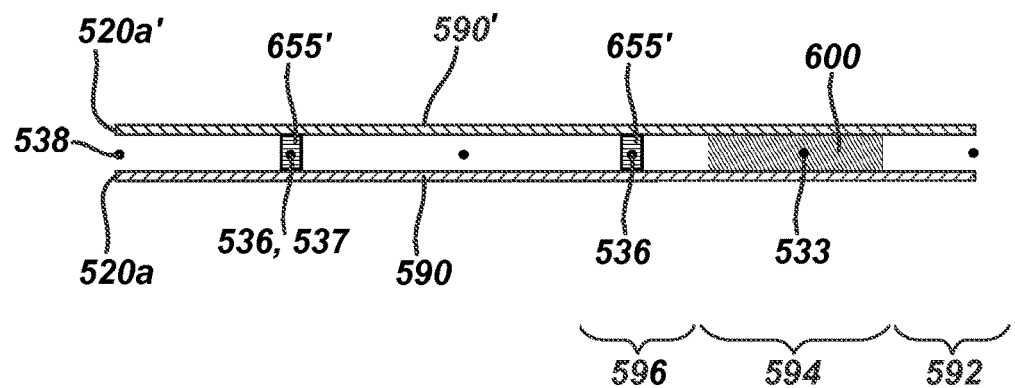
FIG. 70 is a cross sectional side view of an exemplary ultrasonic core for an ultrasonic surgical instrument.

FIG. 70 illustrates another exemplary ultrasonic core 900 for an ultrasonic surgical instrument 900. The core 900 includes a longitudinally elongated, generally planar waveguide 590, constructed from a single crystal or polycrystalline material, and a transducer structure 600 affixed to the waveguide. However, the core 900 also further includes an additional longitudinally elongated, generally planar waveguide 590', constructed from the same material, affixed to an opposite side of the transducer structure 600 to form a mutually opposing pair of spaced apart waveguides 590, 590'. The waveguides 590, 590' each include an end effector 520a, 520a' projecting beyond a spacer 655' disposed between the waveguides at a distal node 536 to form mutually opposing tines in a coherent interference end effector. The distal node is preferably a distal-most node 537, with the distal ends of the end effectors 520a, 520a' being disposed at a distal-most anti-node 538. Additional spacers 655' may be also disposed at other distal nodes 536 in order to maintain adequate separation of the waveguides 590, 590'.

The transducer structure is configured to operate in a transverse resonant mode "$T_1$" perpendicular to the planes of the waveguides 590, 590'. As a result, contraction of the transducer material will pull transduction portion 594 of each waveguide toward the other, and expansion of the transducer material will push the transduction portion of each waveguide away from each other. This transverse ultrasonic vibration of the waveguides 590, 590' will be replicated, neglecting the effects of ultrasonic gain produced in a distal resonator 596 or the like, in the projecting ends of the end effectors 520a, 520a' at a distal-most anti-node 538. Since the two waveguides 590, 590a' are driven at the same resonant frequency by the transducer structure 600, the transverse ultrasonic vibration will be coherent and, considering one mutually opposing tine with respect to the other, 180° out-of-phase so as to cause constructive interference at least in the space between the mutually opposing tines. This constructive interference enhances tissue friction and heating between the mutually opposing tines, allowing for the use of smaller, less powerful transducer structures and also enhancing the frictional heating of tissue surrounding the mutually opposing tines.

Transducer-to-Waveguide Coupling

Implementations of the fifth embodiment may be substantially smaller, more compact, less mechanically complex, and less expensive due to the transducer-on-planar-waveguide construction, polycrystalline or single crystal material base, alternate means of affixing and electrically connecting transducer structures, and other features discussed above. However, these constructions tend to have narrow phase margins and tend to be subject to rapid shifts in system modal frequency when applied to loads such as patient tissues. As a result, the relative positioning and dimensions of the transducer structure relative to the longitudinally elongated, generally planar waveguide have been found to have a substantial effect upon the ability of such devices to drive power into patient tissues, dermal fillers, acoustic coupling fluids, and the like without generating excessive latent or waste heat or causing the system modal frequency to shift (both in terms of frequency and rapidity of frequency shift) in a manner which cannot reasonably be tracked by a ultrasound generator powering the ultrasonic core.

Figure 71:
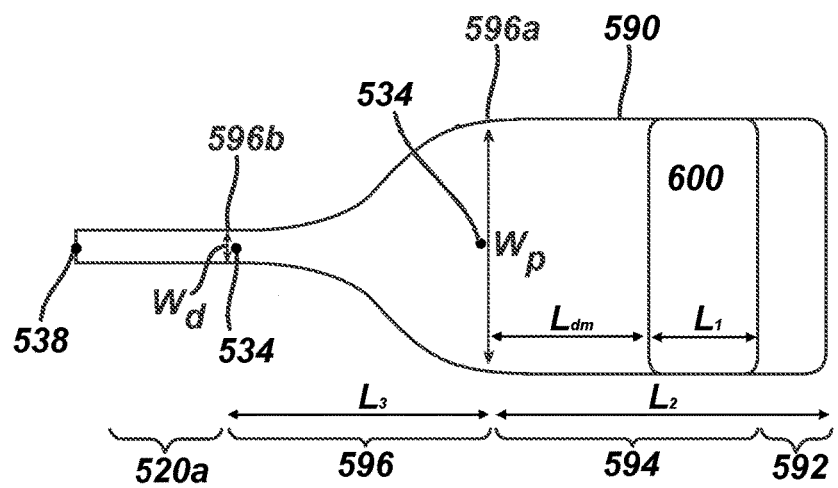
FIG. 71 is a schematic side view of an ultrasonic core construction.

In a fourth expression of the fifth embodiment, an ultrasonic core such as that illustrated in FIG. 71, the transducer structure 600 affixed to the transduction portion 594 has a first length, $L_1$, and the transduction portion 594, or the combination of the first or proximal resonator 592 and transduction portion 594 where the former is included, has a second longitudinal length, $L_2$. The second or distal resonator 596, has a proximal end 596a, generally distinguished by a change in geometry near a node 534 (most typically, the start of reduction in transverse extent, e.g., width w, where w decreases from $w_p$), and a distal end 596b, generally distinguished by a cessation in the change in geometry near more distal node 534 (most typically, the start of a section of constant transverse extent, e.g., width w, where w remains equal to $w_d$), and a length, $L_3$, between proximal end 596a and distal end 596b. Accordingly, transducer structure 600 may be separated from proximal end 596a of the distal resonator 596 by a distal margin indicated by $L_{dm}$. As indicated in FIG. 71, the transduction portion 594 and any first or proximal resonator typically have a first lateral extent, a distal end or end effector portion of the waveguide typically has a second, narrower lateral extent, with the second or distal resonator 596 transitioning from the first lateral extent (i.e., $w_p$) to the second lateral extent (i.e., $w_d$) in one of the manners described a first expression of the fifth embodiment above. In a preferred exemplary construction of the illustrated device, the length $L_2$ is 40 mm, the length $L_3$ is 20 mm, the first lateral extent (corresponding to $w_p$) is 10 mm, and the second lateral extent (corresponding to $w_d$) is 2.5 mm. In the preferred construction and illustration the waveguide 590, including a distal end effector portion 520a having a distal-most anti-node 538, has an overall length of 70 mm; however, those of skill in the art will appreciate that length of the waveguide 590 distal from the distal resonator may be varied, e.g., by adding half-wavelength lengths to the distal end effector portion 520a, without substantially varying the design rules and relative dimensions discussed below. A DOE model was constructed for the preferred construction with a transitional catenary shaped distal resonator 596, where the width of the distal resonator 596 from proximal end 596a to distal end 596b is describable by:

$$w(l) = w_d(\cosh(\alpha(L_3 - l)))^2, \alpha = \frac{1}{L_3}\cosh^{-1}\left(\sqrt{\frac{w_p}{w_d}}\right) \quad (1)$$

and l ranges from 0 at the proximal end 596a to $L_3$ at the distal end 596b. This DOE model was subsequently used to test design rules discussed in the constructions presented below.

Figure 72:
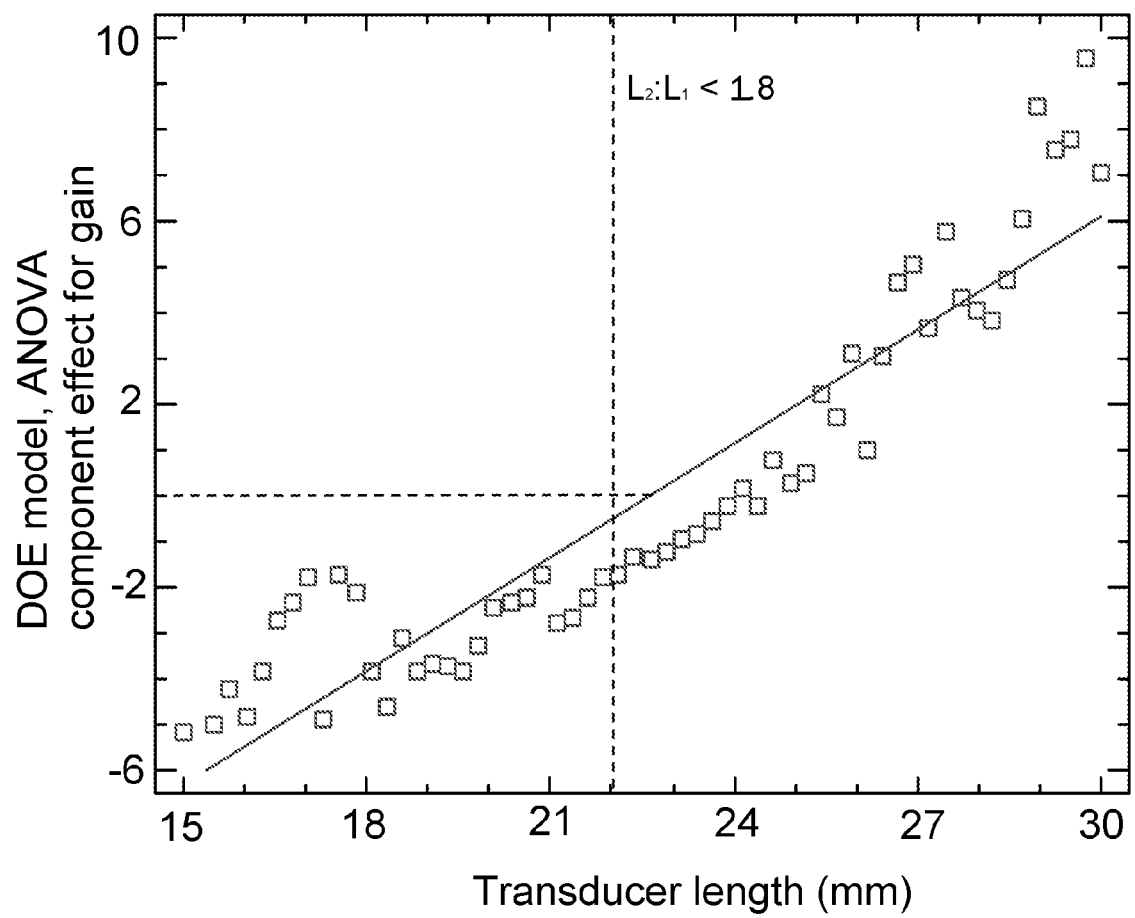
FIGS. 72 and 73 are plots from ANOVA analyses of a DOE model of an exemplary ultrasonic core, illustrating the component effect of transducer length upon gain and acoustic impedance, respectively, of the modeled construction.
Figure 73:
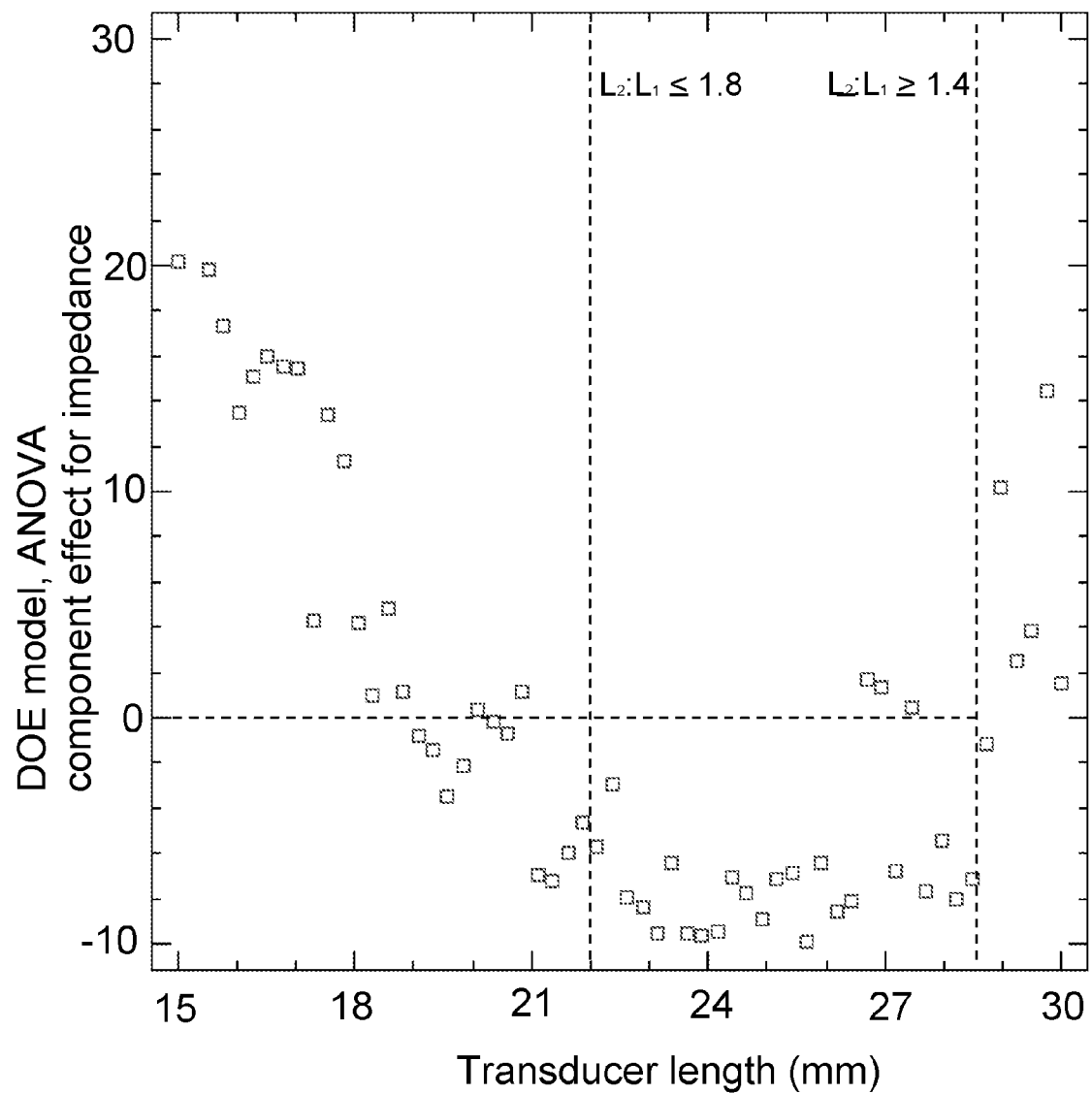

In a first construction of the fourth expression, the ratio of the length of the transduction portion 594 and any proximal resonator 592 to the length of the transducer structure 600 should be less than or equal to 1.8:1, i.e., the transducer structure 600 should be at least half as long as the length of waveguide 790 proximally from the distal resonator 596. As shown in FIG. 72, the ANOVA component effect of the length of transducer 602 upon the acoustic gain of the waveguide 590 is negative (so as to decrease or suppress acoustic amplitude) for ratios greater than 1.8:1, i.e., for transducers 602 with lengths less than 22 mm in the preferred construction, but becomes increasingly positive for ratios less than 1.8:1. As indicated in FIG. 73, such a ratio also serves to minimize the acoustic impedance of the connection between the transducer 602 and the waveguide 590, but only for ratios greater than or equal to 1.4:1. Thus, it is particularly preferred that the ratio of the length of the transduction portion 594, and any proximal resonator 592, to the length of the transducer structure 600 is both less than or equal to 1.8:1 and greater than or equal to 1.4:1.

In a second and related construction of the fourth expression, the difference between an modal frequency of the ultrasonic core, i.e., the system modal frequency, $f_{sys}$, of the transducer structure, waveguide 590, and any distal end effector 520a, and an intrinsic modal frequency of the transducer structure 600 itself, i.e., the intrinsic transducer modal frequency, $f_{trans}$, should be no less than 15 percent and no greater than 32 percent of the total system modal frequency, i.e:

$$0.15 \leq \frac{f_{sys} - f_{trans}}{f_{sys}} \leq 0.32 \quad (2)$$

Figure 74:
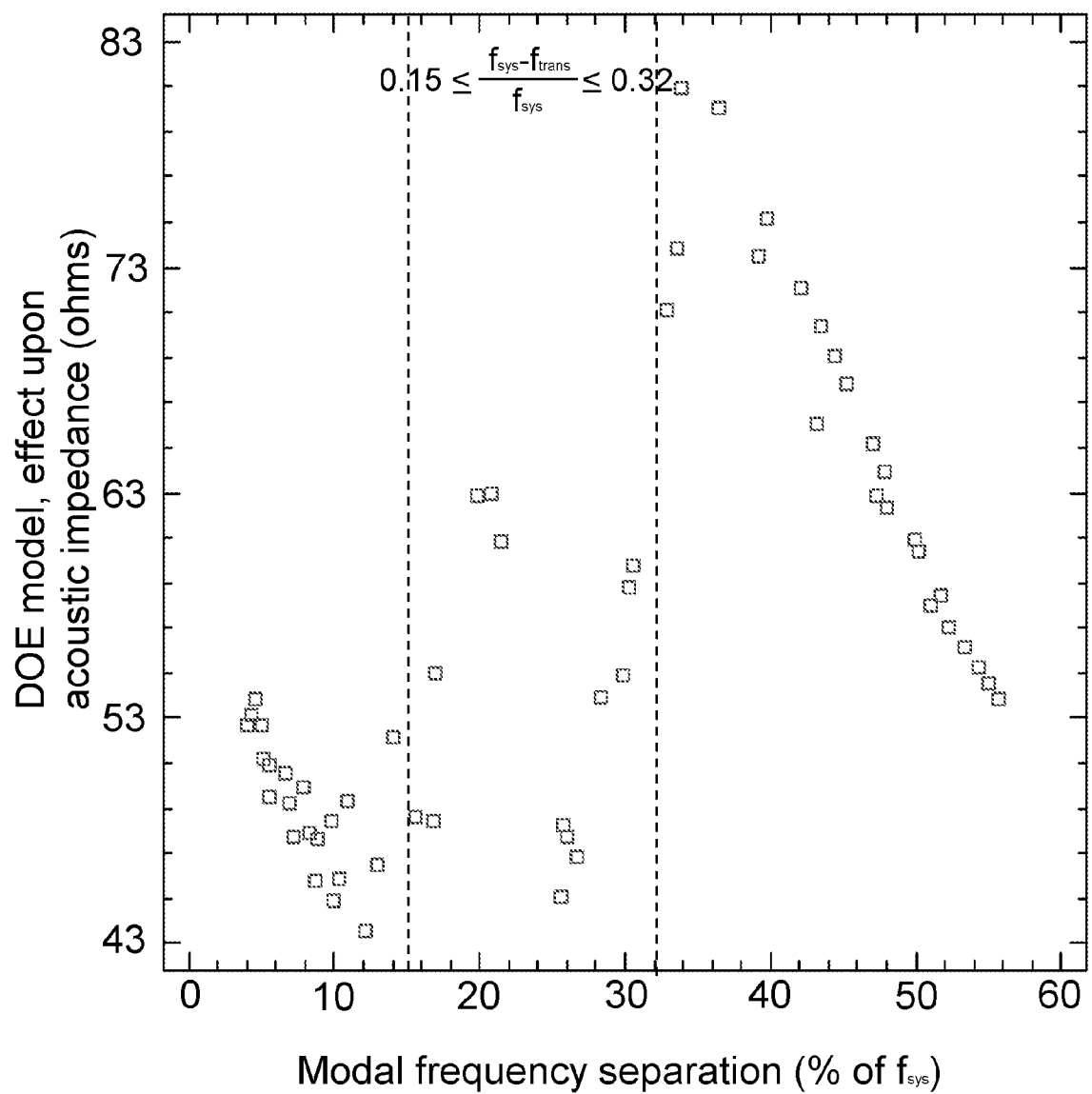
FIGS. 74 and 75 are plots from parametric analyses of the DOE model, illustrating the effect of modal frequency separation upon acoustic impedance and phase peak, respectively, in the modeled construction.

As indicated in FIGS. 73 and 74, such a difference serves to maximize the phase peak of the ultrasonic core while minimizing the acoustic impedance of the connection between the transducer structure 600 and the waveguide 590.

In a third and related construction of the fourth expression, the distal margin between a distal end of the transducer structure 600 and proximal end 592a the distal resonator 592 should be no less than 14 percent and no more than 34 percent of the length of the transduction portion 594 and any proximal resonator 592, i.e.:

$$0.14 \leq \frac{L_{dm}}{L_2} \leq 0.34 \quad (3)$$

Figure 75:
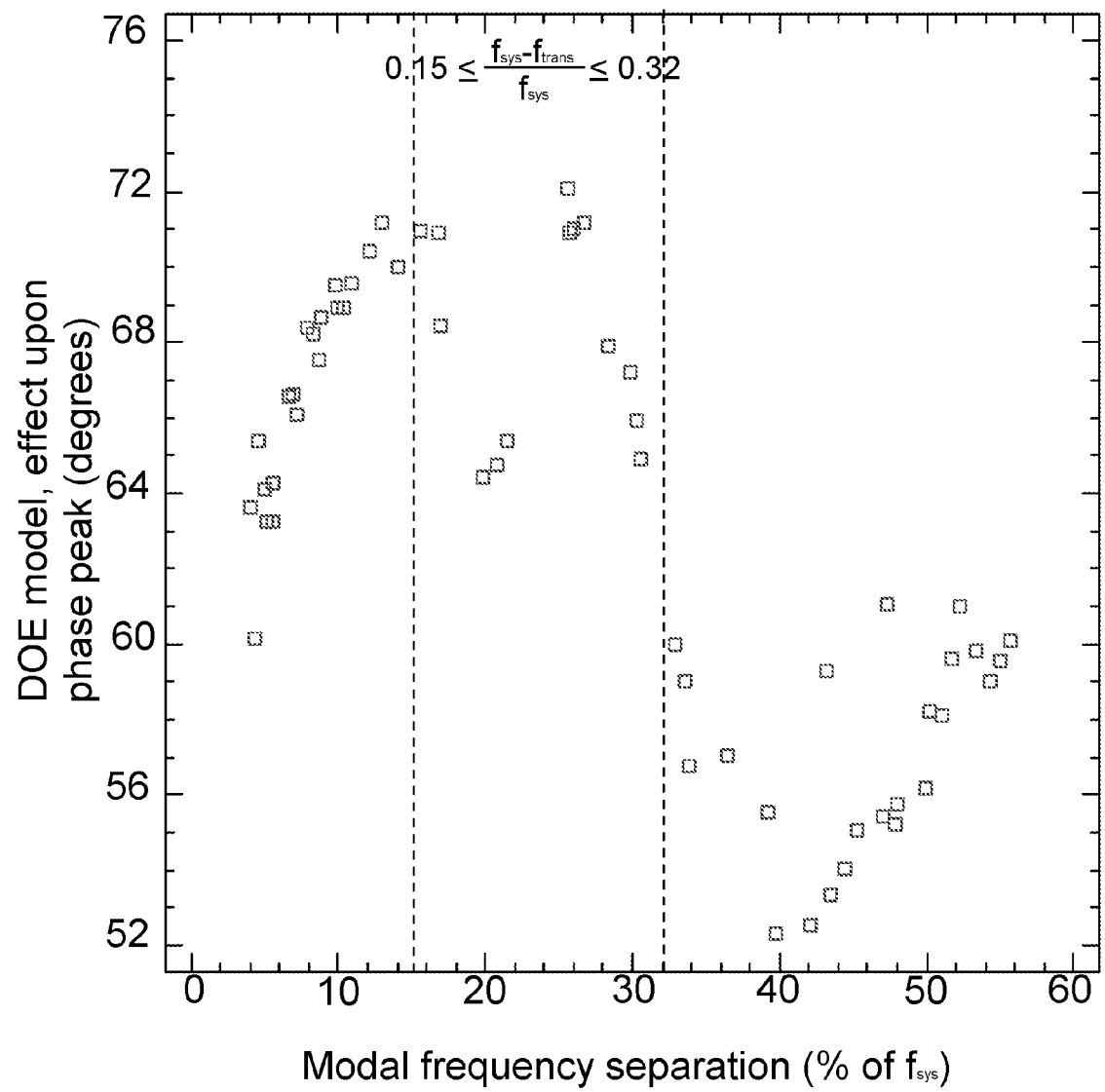
Figure 76:
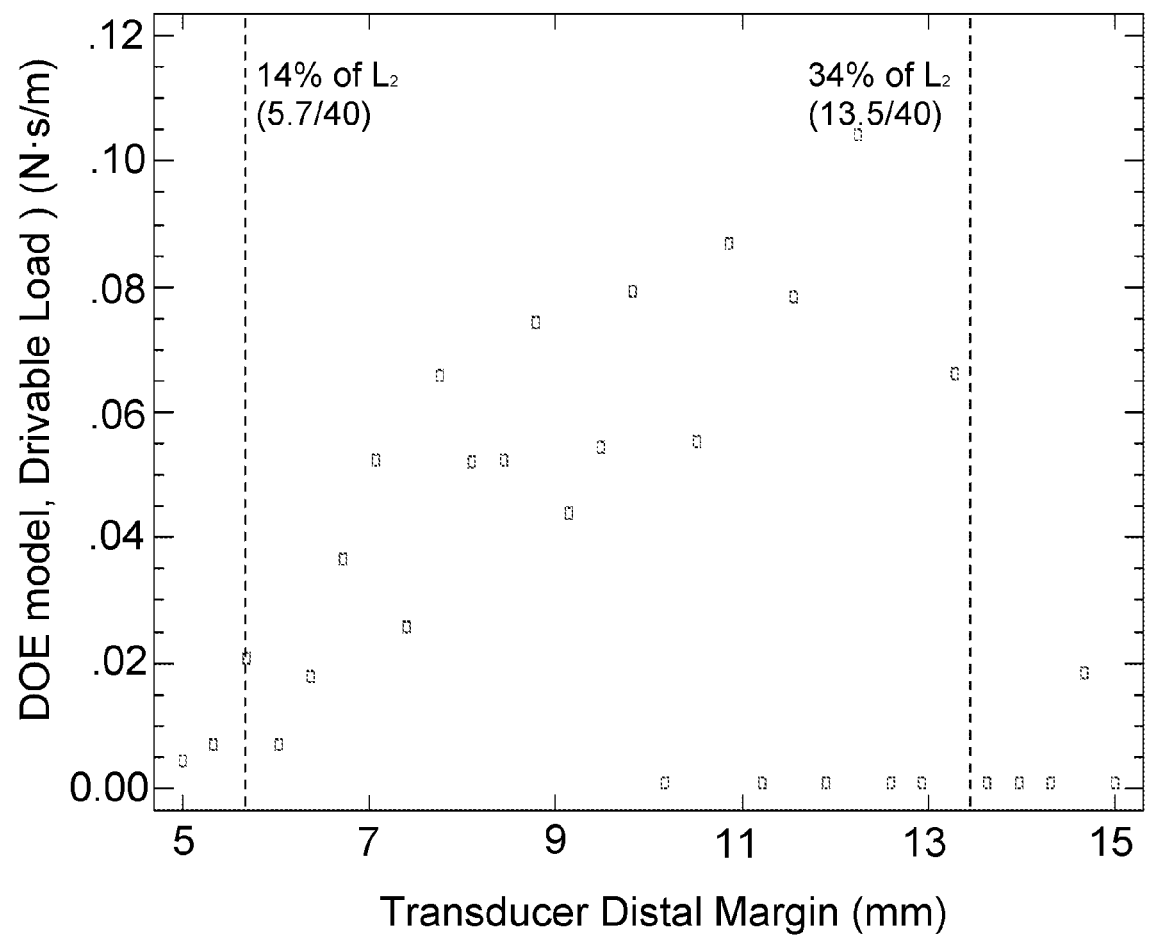
FIG. 76 is a plot from a parametric analyses of the DOE model, illustrating the effect of distal margin between a distal end of a transducer and a proximal end of the distal resonator upon the drive power of a component end effector.

As indicated in FIG. 75, this margin affects the drivable load and may be altered by altering either the length of the transducer structure 600 or the positioning of the transducer structure on the transduction portion 594 of the waveguide 590.

The reader will appreciate that the design rules discussed in the first through third constructions of the fourth expression are to some extent related to each other, such that other constructions may employ subcombinations or a complete combination of these considerations. In a first variation of the preferred exemplary construction introduced above, the transducer structure 600 has a length, $L_1$, of 30 mm and is centered 15 mm from the proximal end of the waveguide, such that there is essentially no proximal resonator, the ratio of the length of the transduction portion 594 to the length of the transducer structure 600 is 1.33:1, the modal frequency separation is about 23%, and the distal margin is 10 mm, or 25%, of the length of the transduction portion 594 ($L_2$). In a second variation of the preferred exemplary construction, the transducer structure has a length, $L_1$, of 27 mm and is centered 20 mm from the proximal end of the waveguide, such that the ratio of the length of the transduction portion 594 to the length of the transducer structure 600 is about 1.5:1, the modal frequency separation is about 23%, and the distal margin is 6.5 mm, or about 16%, of the length of the transduction portion 594 combined with the proximal resonator 592 (combined, $L_2$). With regard to system modal frequency and intrinsic transducer modal frequency, the waveguide 590 was modeled as planar silicon structure which was 1 mm thick and the transducer structure 600 was modeled as a rectangular, PZT-8 transducer which was 10 mm wide and 2 mm thick, yielding a system modal frequency $f_{sys} \approx 82.5$ kHz and an intrinsic transducer modal frequency $f_{trans} \approx 63.8$ kHz for the first variation, and a system modal frequency $f_{sys} \approx 74.8$ kHz and an intrinsic transducer modal frequency $f_{trans} \approx 57.7$ kHz for the second variation. Each variation of the exemplary construction exhibits good acoustic gain and ability to deliver power into a load, as well as minimal acoustical impedance at the connection between transducer structure 600 and waveguide 590.

While the present invention has been illustrated by description of several embodiments, it is not the intention of the applicant to restrict or limit the spirit and scope of the appended claims to such detail. Numerous variations, changes, and substitutions will occur to those skilled in the art without departing from the scope of the invention. Moreover, the structure of each element associated with the present invention can be alternatively described as a means for providing the function performed by the element. Accordingly, it is intended that the invention be limited only by the spirit and scope of the appended claims.

What is claimed is:

1. An ultrasonic core for an ultrasonic surgical apparatus, the core comprising:
    a longitudinally elongated, generally planar waveguide constructed from a single crystal or polycrystalline material, the waveguide including a transduction portion and a distal resonator, the transduction portion and the distal resonator having the same thickness; and
    a transducer structure affixed to the transduction portion of the waveguide;
    wherein the distal resonator is configured to vary the magnitude of a mode of ultrasonic vibration created in the transduction portion and includes a proximal end having first transverse extent, a distal end having a second, lesser transverse extent, and a body generally narrowing between the first and second transverse extents; and
    wherein the edges of the body of the distal resonator are asymmetric with respect to the central longitudinal axis of the wave guide.

2. The ultrasonic core of claim 1, wherein a first edge of the body of the distal resonator is a sinusoidally curved edge, and a second, opposite edge of the body of the distal resonator is a convexly curved edge.

3. The ultrasonic core of claim 1, wherein the transducer structure includes a transducer constructed from a piezoelectric or electrostrictive ceramic, and the transducer is directly bonded to a side of the transduction portion.

4. The ultrasonic core of claim 1, wherein the transducer structure has a first longitudinal length, the transduction portion and any proximal resonator have a second longitudinal length, and a distal margin between a distal end of the transducer structure and a proximal end of the distal resonator is no less than 14 percent and no greater than 34 percent of the second length.

5. An ultrasonic core for an ultrasonic surgical apparatus, the core comprising:
    a longitudinal elongated, generally planar waveguide constructed from a single crystal or polycrystalline material, the waveguide including a transduction portion and a distal resonator, the transduction portion and the distal resonator having the same thickness; and
    a transducer structure affixed to the transduction portion of the waveguide;
    wherein the transducer structure includes a transducer indirectly bonded to a carrier, and the carrier is indirectly bonded to the transduction portion by a surface mount electrical contact;
    wherein the transducer is indirectly bonded to the carrier by a discontinuous pattern of a first bonding material, and further indirectly bonded to the carrier by a second bonding material, wherein at least the second bonding material is a conductive bonding material serving as a driving electrode for the transducer structure; and wherein the transducer is dimensioned to have a greater longitudinal extent than the longitudinal extent of the carrier.

6. The ultrasonic core of claim 5, wherein the carrier is underfilled with a non-conductive adhesive.

7. The ultrasonic core of claim 5, wherein the carrier includes a plurality of through-holes, and the second bonding material is at least partially disposed within the through-holes so as to serve as an electrical connection to the transduction portion.

8. An ultrasonic core for an ultrasonic surgical apparatus, the core comprising:
a longitudinally elongated, generally planar waveguide constructed from a single crystal of polycrystalline material, the waveguide including a transduction portion and a distal resonator, the transduction portion and the distal resonator having the same thickness; and
a transducer structure affixed to the transduction portion of the waveguide; and
an encased coil surrounding the transducer structure and the transduction portion, wherein the transducer structure includes a transducer constructed from a magnetostrictive material.

9. The ultrasonic core of claim 8, wherein the transducer structure is a laminated structure formed from multiple layers of magnetostrictive material, includes an aperture configured to receive a proximal end of the transduction portion of the waveguide, and is indirectly bonded to the proximal end of the transduction portion of the waveguide.

10. The ultrasonic core of claim 9, wherein the aperture is formed parallel to the multiple layers of magnetostrictive material.

11. The ultrasonic core of claim 9, wherein the aperture is formed perpendicular to the multiple layers of magnetostrictive material.

12. An ultrasonic core for an ultrasonic surgical apparatus, the core comprising:
a longitudinally elongated, generally planar waveguide constructed from a single crystal or polycrystalline material, the waveguide including a transduction portion and a distal resonator; and
a transducer structure affixed to the transduction portion of the waveguide,
wherein the transduction portion includes at least one surface mount electrical contact, and the transducer structure is joined to the at least one surface mount electrical contact by a braze.

13. The ultrasonic core of claim 12, wherein the transducer structure is affixed to the transduction portion at least in part by an adhesive.

14. The ultrasonic core of claim 13, wherein the at least one surface mount electrical contact is disposed under the transducer structure.

15. The ultrasonic core of claim 12, wherein the transducer structure includes an opposing electrode formed upon a side of the transducer opposite the transduction portion, and an acoustically isolating mount abutting the side of the transducer structure.

16. The ultrasonic core of claim 12, wherein the transduction portion includes first and second pluralities of surface mount electrical contacts disposed on the exposed side of the transduction portion, with the first plurality electrically connectable to a remote electrical source, and the second plurality electrically connectable to a remote electrical ground.

17. The ultrasonic core of claim 12, wherein the transducer is configured as a multi-element transducer stack having first and second pluralities of electrode portions projecting from stack electrodes disposed between every element of the stack, with the first and second pluralities of electrode portions being alternatingly connected to successive stack electrodes through the stack, the first plurality of electrode portions being surface mounted to the first plurality of surface mount electrical contacts, and the second plurality of electrode portions being surface mounted to the second plurality of surface mount electrical contacts.

18. The ultrasonic core of claim 17, wherein the transducer stack is longitudinally oriented, and operates in a longitudinal extension mode.

19. The ultrasonic core of claim 17, wherein the transducer stack is laterally oriented out of the plane of the waveguide, and operates in a longitudinal extension mode.

20. The ultrasonic core of claim 12, wherein the transducer structure has a first longitudinal length, the transduction portion and any proximal resonator have a second longitudinal length, and the ratio of the second length to the first length is less than or equal to 1.8:1.

21. The ultrasonic core of claim 20, wherein the transducer structure has a first longitudinal length, the transduction portion and any proximal resonator have a second longitudinal length, and the ratio of the second length to the first length is greater than 1.4:1.

22. The ultrasonic core of claim 12, wherein the ultrasonic core has a system modal frequency and the transducer structure itself has an intrinsic transducer modal frequency, and wherein the difference between the system modal frequency and the intrinsic transducer modal frequency is no less than 15 percent and no greater than 32 percent of the system modal frequency.

23. An ultrasonic core for an ultrasonic surgical apparatus, the core comprising:
a longitudinally elongated, generally planar waveguide constructed from a single crystal or polycrystalline material, the waveguide including a transduction portion and a distal resonator; and
a transducer structure affixed to the transduction portion of the waveguide,
wherein the longitudinally elongated, generally planar waveguide includes a proximal resonator, disposed proximally from the transduction portion, and an end mass is affixed to the proximal resonator.

24. The ultrasonic core of claim 23, wherein the end mass is proximally spaced apart from the transducer structure and sized so as to function as a virtual node in a principal mode of vibration of the ultrasonic core.

25. The ultrasonic core of claim 23, further comprising an instrument housing, wherein the end mass is proximally spaced apart from the transducer structure and fixed within and with respect to the instrument housing so as to function as a virtual node in a principal mode of vibration of the ultrasonic core.

26. The ultrasonic core of claim 25, further comprising an acoustically isolating mount interconnecting the waveguide and the instrument housing, wherein the transducer structure is disposed at an intermediate antinode and the acoustically isolating mount is disposed at a distal node.

27. The ultrasonic core of claim 26, wherein the waveguide includes a distal end effector, and wherein the instrument housing includes a sheath projecting distally over the end effector.

28. The ultrasonic core of claim 27, wherein the waveguide is a laminated structure including a plurality of planar layers of the single crystal or polycrystalline material, and wherein at least two adjoining layers of the plurality of planar layers define an internal lumen.

29. The ultrasonic core of claim 27, wherein the end mass includes an end mass lumen, correspondingly positioned and in fluid communication with the internal lumen, and a fitting permitting matter to be exchanged through the end mass and internal lumens.

30. An ultrasonic core for an ultrasonic surgical apparatus, the core comprising:
a longitudinally elongated, generally planar waveguide constructed from a single crystal or polycrystalline material, the waveguide including a transduction portion and a distal resonator, the transduction portion and the distal resonator having the same thickness;
a transducer structure affixed to the transduction portion of the waveguide; and
an instrument housing surrounding at least the transduction portion and transducer structure, wherein the waveguide includes an end effector configured to provide a blunt side surface disposed at a distal-most anti-node, and wherein the housing includes a flexible tine extending along the waveguide, the flexible tine having a tissue pad opposing the blunt side surface.

31. The ultrasonic core of claim 30, wherein the housing includes a first acoustically isolating mount, disposed about the waveguide at a proximal node, and a second acoustically isolating mount, disposed about the waveguide at a distal node.

32. The ultrasonic core of claim 30, wherein the flexible tine includes a finger pad disposed proximate an intermediate node.

33. The ultrasonic core of claim 30, wherein the housing includes a finger pad disposed proximate the intermediate node.

34. An ultrasonic core for an ultrasonic surgical apparatus, the core comprising:
a longitudinally elongated, generally planar waveguide constructed from a single crystal or polycrystalline material, the waveguide including a transduction portion and a distal resonator, the transduction portion and the distal resonator having the same thickness; and
a transducer structure affixed to the transduction portion of the waveguide;
wherein the waveguide includes an end effector having a distal tip constructed from a second, dissimilar material, the second, dissimilar material being selected from a group consisting of a metallic, glassy, polycrystalline, or crystalline material having a greater toughness than the single crystal or polycrystalline material, wherein the waveguide is a laminated structure including a plurality of planar layers of the single crystal or polycrystalline material, and wherein the distal tip includes a tang projecting proximally into the end effector.

35. The ultrasonic core of claim 34, wherein the tang is tapered toward its proximal end, and the end effector includes a complementary socket configured to conformingly receive the tang.

36. The ultrasonic core of claim 34, wherein the tang is generally planar with a generally perpendicular, proximal abutment wall, and the end effector includes a complementary socket configured to conformingly receive and abut the tang.

37. The ultrasonic core of claim 34, wherein the tang is a full width tang, and the plurality of layers includes at least a first adjacent layer, laminated to a first side of the tang, and a second adjacent layer, laminated to a second, opposite side of the tang.

38. An ultrasonic core for an ultrasonic surgical apparatus, the core comprising:
a longitudinally elongated, generally planar waveguide constructed from a single crystal or polycrystalline material, the waveguide including a transduction portion and a distal resonator, the transduction portion and the distal resonator having the same thickness;
a transducer structure affixed to the transduction portion of the waveguide; and
an additional longitudinally elongated, generally planar waveguide constructed from the single crystal or polycrystalline material and affixed to an opposite side of the transducer structure to form a mutually opposing pair of spaced apart waveguides, wherein the waveguides each include an end effector projecting beyond a spacer disposed between the waveguides at a distal node.

39. The ultrasonic core of claim 38, wherein the spacer is disposed at a distal-most node, and the distal ends of the end effectors of the waveguides are disposed at a distal-most antinode.

40. The ultrasonic core of claim 39, wherein the transducer structure is configured to operate in a transverse resonant mode perpendicular to the planes of the waveguides.

* * * * *

UNITED STATES PATENT AND TRADEMARK OFFICE
CERTIFICATE OF CORRECTION

| | | |
|---|---|---|
| PATENT NO. | : 9,737,735 B2 | Page 1 of 1 |
| APPLICATION NO. | : 13/745385 | |
| DATED | : August 22, 2017 | |
| INVENTOR(S) | : Timothy G. Dietz et al. | |

It is certified that error appears in the above-identified patent and that said Letters Patent is hereby corrected as shown below:

Claim 5, Column 42, Line 55 reads:
"a longitudinal elongated, generally planar waveguide"
Should read:
-- a longitudinally elongated, generally planar waveguide --

Signed and Sealed this
Tenth Day of October, 2017

Joseph Matal
*Performing the Functions and Duties of the*
*Under Secretary of Commerce for Intellectual Property and*
*Director of the United States Patent and Trademark Office*